US012012603B2

(12) United States Patent
Hittinger et al.

(10) Patent No.: US 12,012,603 B2
(45) Date of Patent: Jun. 18, 2024

(54) YEAST STRAINS WITH SELECTED OR ALTERED MITOTYPES AND METHODS OF MAKING AND USING THE SAME

(71) Applicant: Wisconsin Alumni Research Foundation, Madison, WI (US)

(72) Inventors: Chris Todd Hittinger, Madison, WI (US); David Peris Navarro, Valencia (ES); EmilyClare Patricia Baker, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/533,928

(22) Filed: Aug. 7, 2019

(65) Prior Publication Data

US 2020/0048645 A1 Feb. 13, 2020

Related U.S. Application Data

(60) Provisional application No. 62/715,498, filed on Aug. 7, 2018.

(51) Int. Cl.
  *C12N 15/81* (2006.01)
  *C12N 1/14* (2006.01)
  *C12N 1/18* (2006.01)
  *C12R 1/645* (2006.01)

(52) U.S. Cl.
  CPC .............. *C12N 15/81* (2013.01); *C12N 1/145* (2021.05); *C12N 1/18* (2013.01); *C12R 2001/645* (2021.05)

(58) Field of Classification Search
  CPC .................................................... C12N 15/81
  See application file for complete search history.

(56) References Cited

U.S. PATENT DOCUMENTS

| 7,396,664 | B2 | 7/2008 | Daly | |
| 2014/0302577 | A1* | 10/2014 | Thorsness | C12Y 114/99001 435/161 |
| 2016/0046952 | A1 | 2/2016 | Hittinger | |
| 2018/0127784 | A1 | 5/2018 | Alexander | |
| 2018/0155732 | A1 | 6/2018 | Hittinger | |
| 2019/0315815 | A1 | 10/2019 | Hittinger | |

OTHER PUBLICATIONS

Magalhães et. al. Improved cider fermentation performance and quality with newly generated *Saccharomyces cerevisiae* x *Saccharomyces eubayanus* hybrids. 2017. J Ind Microbiol Biotechnol 44:1203-1213 (Year: 2017).*
Salvado et. al. 2011. Temperature Adaptation Markedly Determines Evolution within the Genus *Saccharomyces*. Applied and Environmental Microbiology, p. 2292-2302 (Year: 2011).*
Hebly et. al. *S. cerevisiae* x *S. eubayanus* interspecific hybrid, the best of both worlds and beyond. 2015 FEMS Yeast Research, vol. 15, Issue 3, p. 1-14 (Year: 2015).*
Lee et. al. Incompatibility of Nuclear and Mitochondrial Genomes Causes Hybrid Sterility between Two Yeast Species Cell 135, 1065-1073, Dec. 12, 2008 (Year: 2008).*
Wolters et al. Mitochondrial Recombination Reveals Mito-Mito Epistasis in Yeast Genetics, vol. 209, 307-319 May 2018 (Year: 2018).*
Peris D, et al. 2017. Mitochondrial introgression suggests extensive ancestral hybridization events among *Saccharomyces* species. Mol. Phylogenet. Evol. 108:49-60.
Peris D, et al. 2018. On the origins and industrial applications of *Saccharomyces cerevisiae* x *Saccharomyces kudriavzevii* hybrids. Yeast 35:51-69.
Peris D, et al. Complex Ancestries of Lager-Brewing Hybrids Were Shaped by Standing Variation in the Wild Yeast *Saccharomyces eubayanus*. PLOS Genet. 2016;12(7):e1006155. pmid:27385107.
Peris D, et al. Population structure and reticulate evolution of *Saccharomyces eubayanus* and its lager-brewing hybrids. Mol Ecol. 2014;23(8):2031-45. pmid:24612382.
Pichaud N, et al. 2013. Mitochondrial haplotype divergences affect specific temperature sensitivity of mitochondrial respiration. J. Bioenerg. Biomembr. 45:25-35.
Salvado Z, et al. 2011. Temperature adaptation markedly determines evolution within the genus *Saccharomyces*. Appl. Environ. Microbiol. 77:2292-2302.
Spirek M, et al. 2014. Post-zygotic sterility and cytonuclear compatibility limits in *S. cerevisiae* xenomitochondrial cybrids. Front. Genet. 5:454.
Sylvester K, et al. 2015. Temperature and host preferences drive the diversification of *Saccharomyces* and other yeasts: a survey and the discovery of eight new yeast species. FEMS Yeast Res. 15:fov002.
Thorsness PE, et al. 1993. Nuclear mutations in *Saccharomyces cerevisiae* that affect the escape of DNA from mitochondria to the nucleus. Genetics 134:21-28.
Walther A, et al. 2014. Genome Sequence of *Saccharomyces carlsbergensis*, the World's First Pure Culture Lager Yeast. G3 4:783-793.
Wolters JF, et al. 2018. Mitochondrial Recombination Reveals Mito-Mito Epistasis in Yeast. Genetics 209:307-319.
Yamagishi H, et al. 2010. Role of bottom-fermenting brewer's yeast KEX2 in high temperature resistance and poor proliferation at low temperatures. J. Gen. Appl. Microbiol. 56:297-312.

(Continued)

*Primary Examiner* — Celine X Qian
*Assistant Examiner* — Tiffany Nicole Grooms
(74) *Attorney, Agent, or Firm* — Quarles & Brady, LLP

(57) ABSTRACT

Herein we demonstrate that the mitochondrial genome influences temperature tolerance in *Saccharomyces* yeasts. The present invention provides methods for manipulating the mitotype of yeast, including methods to produce synthetic yeast hybrids with a selected mitotype and methods to exchange the native mitochondrial DNA (mtDNA) present in polyploid yeast with mtDNA from a desired source. *Saccharomyces cerevisiae*×*Saccharomyces eubayanus* hybrids with selected mitotypes are also provided. The yeast and methods of the present invention may be utilized in a variety of applications, including in fermentation to produce beer and wine.

7 Claims, 19 Drawing Sheets

Specification includes a Sequence Listing.

(56) References Cited

OTHER PUBLICATIONS

Zweifel SG, et al. 1991. A nuclear mutation reversing a biased transmission of yeast mitochondrial DNA. Genetics 128:241-249.
Alexander W. G., et al., 2016 Efficient engineering of marker-free synthetic allotetraploids of *Saccharomyces*. Fungal Genet. Biol. 89: 10-17.
Alexander WG, et al. 2014. High-efficiency genome editing and allele replacement in prototrophic and wild strains of *Saccharomyces*. Genetics 198:859-866.
Baker E, et al. The Genome Sequence of *Saccharomyces eubayanus* and the Domestication of Lager-Brewing Yeasts. Mol Biol Evol. 2015;32(11):2818-31. pmid:26269586.
Baris TZ, et al. 2016. Gene by environmental interactions affecting oxidative phosphorylation and thermal sensitivity. Am. J. Physiol. Integr. Comp. Physiol. 311:R157-R165.
Berger KH, et al. 2000. Mitochondrial DNA inheritance in *Saccharomyces cerevisiae*. Trends Microbiol. 8:508-513.
Bing J, et al. Evidence for a Far East Asian origin of lager beer yeast. Curr Biol. 2014;24(10):R380-1. pmid:24845661.
Bokulich NA, et al. 2013. The microbiology of malting and brewing. Microbiol. Mol. Biol. Rev. 77:157-172.
Brachmann CB, et al. 1998. Designer deletion strains derived from *Saccharomyces cerevisiae* S288C: a useful set of strains and plasmids for PCR-mediated gene disruption and other applications. Yeast 14:115-132.
Camus MF, et al. 2017. Experimental Support That Natural Selection Has Shaped the Latitudinal Distribution of Mitochondrial Haplotypes in Australian *Drosophila melanogaster*. Mol. Biol. Evol. 34:2600-2612.
Conde J, et al. 1976. A mutant of *Saccharomyces cerevisiae* defective for nuclear fusion. Proc. Natl. Acad. Sci. U. S. A. 73:3651-3655.
Costanzo MC, et al. 1993. Suppression of a defect in the 5' untranslated leader of mitochondrial COX3 mRNA by a mutation affecting an mRNA-specific translational activator protein. Mol. Cell. Biol. 13:4806-4813.
Dashko S, et al. 2014. Why, when, and how did yeast evolve alcoholic fermentation? FEMS Yeast Res. 14:826-832.
Dujon B. 2006. Yeasts illustrate the molecular mechanisms of eukaryotic genome evolution. Trends Genet. 22:375-387.
Dunn B, et al. 2008. Reconstruction of the genome origins and evolution of the hybrid lager yeast *Saccharomyces pastorianus*. Genome Res. 18:1610-1623.
Fox TD, et al. 1991. Analysis and manipulation of yeast mitochondrial genes. Methods Enzymol. 194:149-165.
Gibson B. R., et al., 2013 Comparative physiology and fermentation performance of Saaz and Frohberg lager yeast strains and the parental species *Saccharomyces eubayanus*. Yeast 30: 255-266.
Gibson B., et al., 2015 *Saccharomyces pastorianus*: genomic insights inspiring innovation for industry. Yeast 32: 17-27.
Goncalves M, et al. 2016. Distinct Domestication Trajectories in Top-Fermenting Beer Yeasts and Wine Yeasts. Curr. Biol. 26:2750-2761.
Goncalves P, et al. 2011. Evidence for divergent evolution of growth temperature preference in sympatric *Saccharomyces* species. PLOS One 6:e20739.
Hebly M, et al. *S. cerevisiae* x *S. eubayanus* interspecific hybrid, the best of both worlds and beyond. FEMS Yeast Res. 2015;15(3):fov005. pmid:25743788.
Hittinger C. T., et al., 2018 Diverse yeasts for diverse fermented beverages and foods. Curr. Opin. Biotechnol. 49: 199-206.
Hittinger CT, et al. 2007. Gene duplication and the adaptive evolution of a classic genetic switch. Nature 449:677-681.
Hittinger CT. 2013. *Saccharomyces* diversity and evolution: a budding model genus. Trends Genet. 29:309-317.
Hsu Y-Y, et al. 2017. Environmental Factors Can Influence Mitochondrial Inheritance in the *Saccharomyces* Yeast Hybrids. PLoS One 12:e0169953.
International Searching Authority. International Search Report and Written Opinion for application PCT/US2019/045386. Mailed on Dec. 6, 2019.
Kellis M, et al. 2003. Sequencing and comparison of yeast species to identify genes and regulatory elements. Nature 423:241-254.
Krogerus K, et al. Inheritance of brewing-relevant phenotypes in constructed *Saccharomyces cerevisiae* x *Saccharomyces eubayanus* hybrids. Microb Cell Fact. 2017;16(1):66. pmid:28431563.
Krogerus K, et al. New lager yeast strains generated by interspecific hybridization. J Ind Microbiol Biotechnol. 2015;42(5):769-78. pmid:25682107.
Krogerus K, et al. Novel brewing yeast hybrids: creation and application. Appl Microbiol Biotechnol. 2017;101(1):65-78. pmid:27885413.
Krogerus K, et al. Ploidy influences the functional attributes of de novo lager yeast hybrids. Appl Microbiol Biotechnol. 2016;100(16):7203-22. pmid:27183995.
Langdon, Q. K., et al. "sppIDer: a species identification tool to investigate hybrid genomes with high-throughput sequencing." Molecular biology and evolution 35.11 (2018): 2835-2849.
Leducq J-B, et al. 2017. Mitochondrial Recombination and Introgression during Speciation by Hybridization. Mol. Biol. Evol. 34:1947-1959.
Li, X. C., et al. "Mitochondria-encoded genes contribute to the evolution of heat and cold tolerance among *Saccharomyces* species." BioRxiv (2018): 390500.
Li, X. C., et al. 2017. Cis-Regulatory Divergence in Gene Expression between Two Thermally Divergent Yeast Species. Genome Biol. Evol. 9:1120-1129.
Libkind D, et al. Microbe domestication and the identification of the wild genetic stock of lager-brewing yeast. Proc Natl Acad Sci U S A. 2011;108(35):14539-44. pmid:21873232.
Liti G, et al. 2006. Sequence diversity, reproductive isolation and species concepts in *Saccharomyces*. Genetics 174:839-850.
Magalhaes, F., et al. "Improved cider fermentation performance and quality with newly generated *Saccharomyces cerevisiae* x *Saccharomyces eubayanus* hybrids." Journal of industrial microbiology & biotechnology 44.8 (2017):1203-1213.
Marinoni G, et al. 1999. Horizontal Transfer of Genetic Material among *Saccharomyces* Yeasts Horizontal Transfer of Genetic Material among *Saccharomyces* Yeasts. 181:6488-6496.
McCullough MJ, et al. 1998. Intergenic transcribed spacer PCR ribotyping for differentiation of *Saccharomyces* species and interspecific hybrids. J. Clin. Microbiol. 36:1035-1038.
Melo-Ferreira J, et al. 2014. The Elusive Nature of Adaptive Mitochondrial DNA Evolution of an Arctic Lineage Prone to Frequent Introgression. Genome Biol. Evol. 6:886-896.
Merico A, et al. 2007. Fermentative lifestyle in yeasts belonging to the *Saccharomyces* complex. FEBS J. 274:976-989.
Mertens S, et al. A large set of newly created interspecific *Saccharomyces* hybrids increases aromatic diversity in lager beers. Appl Environ Microbiol. 2015;81(23):8202-14. pmid:26407881.
Nakao Y, et al. Genome sequence of the lager brewing yeast, an interspecies hybrid. DNA Res. 2009;16: 115-129. pmid:19261625.
Naseeb S, et al. 2017. *Saccharomyces jurei* sp. nov., isolation and genetic identification of a novel yeast species from Quercus robur. Int. J. Syst. Evol. Microbiol. 67:2046-2052.
Nikulin J, et al. Alternative *Saccharomyces* interspecies hybrid combinations and their potential for low-temperature wort fermentation. Yeast. 2018;35: 113-127. pmid:28755430.
Okuno M, et al. Next-generation sequencing analysis of lager brewing yeast strains reveals the evolutionary history of interspecies hybridization. DNA Res. 2016;23(1):67-80. pmid:26732986.
Paget CM, et al. 2014. Environmental systems biology of cold-tolerant phenotype in *Saccharomyces* species adapted to grow at different temperatures. Mol. Ecol. 23:5241-5257.
Paliwal S, et al. 2014. Mitochondrial-nuclear epistasis contributes to phenotypic variation and coadaptation in natural isolates of *Saccharomyces cerevisiae*. Genetics 198:1251-1265.
Peris D, et al. 2012. Comparative genomics among *Saccharomyces cerevisiae* x *Saccharomyces kudriavzevii* natural hybrid strains isolated from wine and beer reveals different origins. BMC Genomics 13:407.

(56) References Cited

OTHER PUBLICATIONS

Peris D, et al. 2012. The molecular characterization of new types of *Saccharomyces cerevisiae*×*S. kudriavzevii* hybrid yeasts unveils a high genetic diversity. Yeast 29:81-91.

* cited by examiner

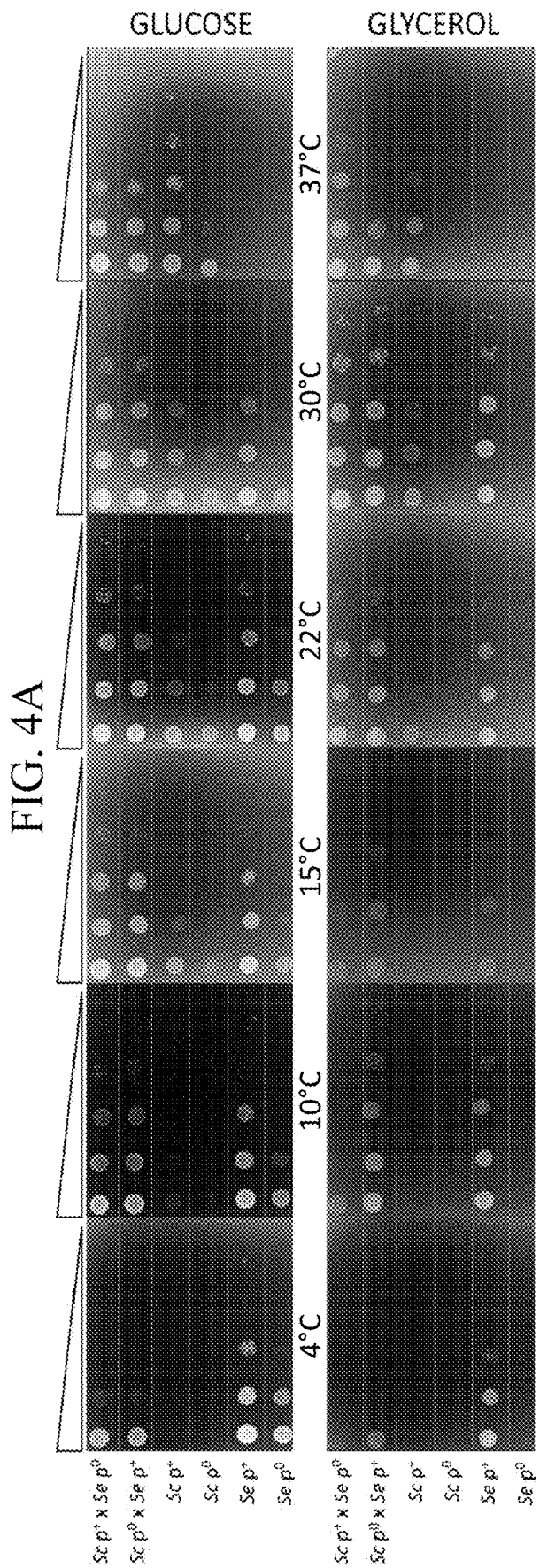

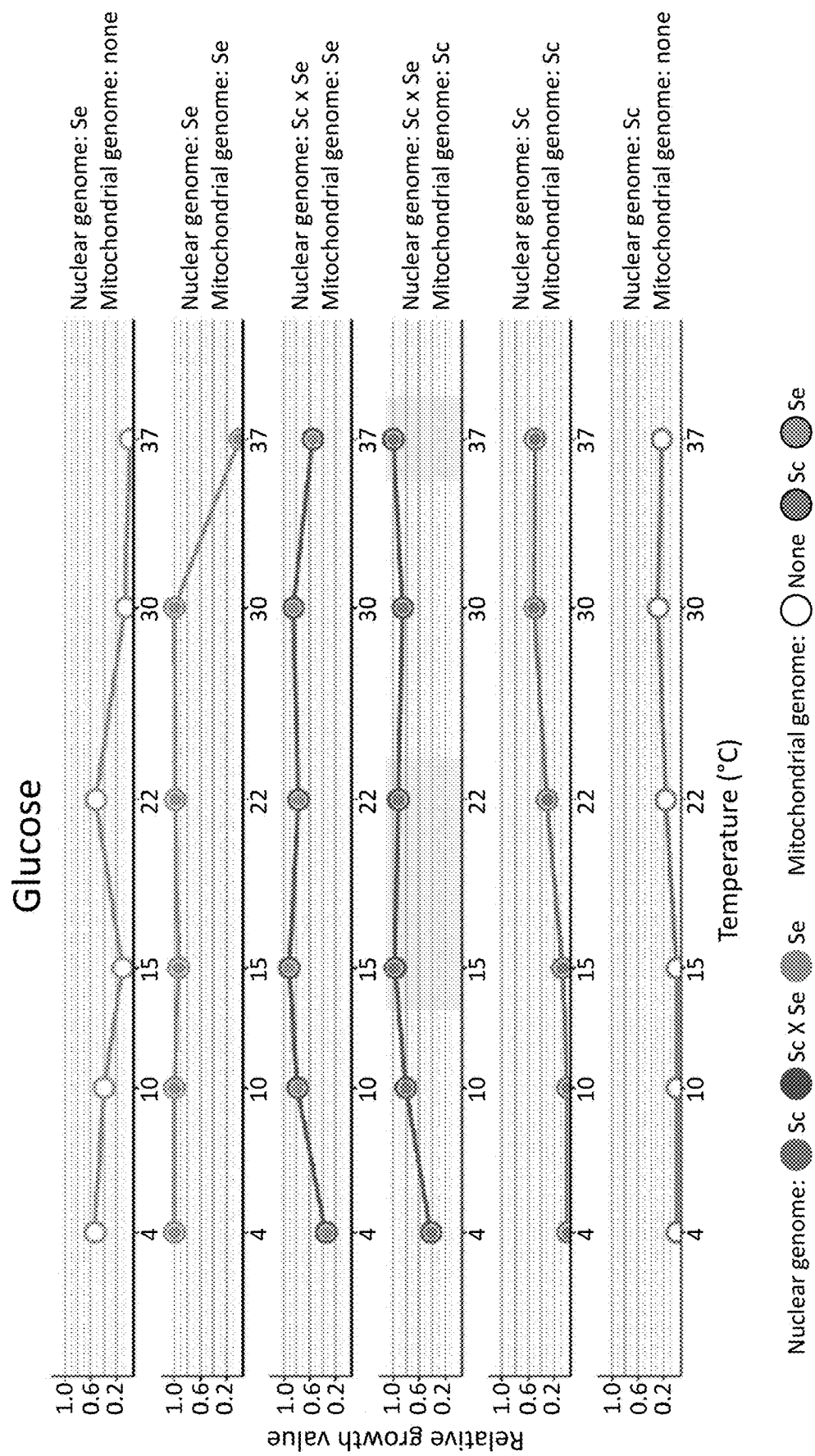

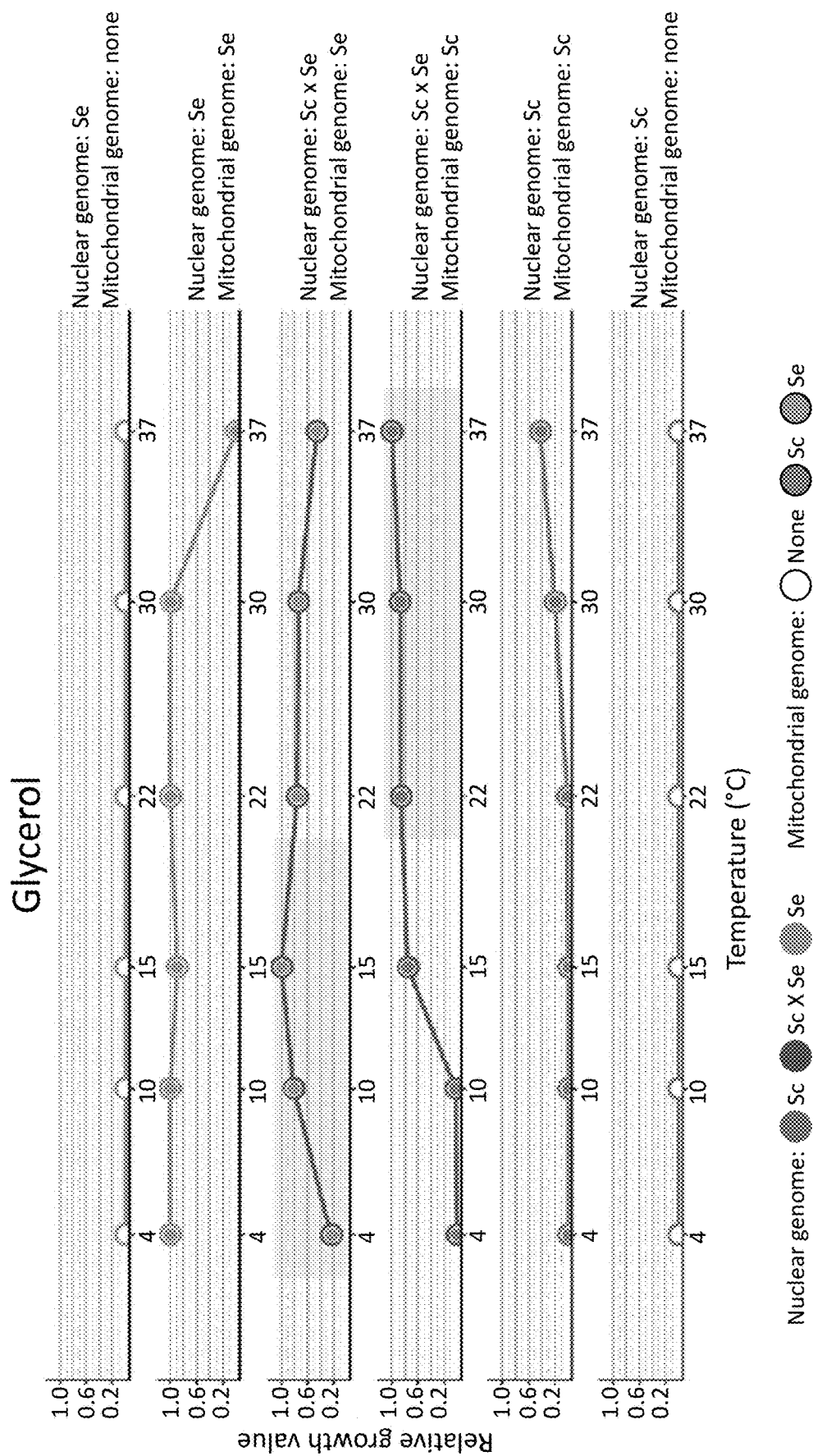

US 12,012,603 B2

YEAST STRAINS WITH SELECTED OR ALTERED MITOTYPES AND METHODS OF MAKING AND USING THE SAME

CROSS-REFERENCE TO RELATED APPLICATIONS

This patent application claims the benefit of priority of United States Provisional Patent Application No. 62/715,498, filed Aug. 7, 2018, which is incorporated herein by reference in its entirety.

STATEMENT REGARDING FEDERALLY SPONSORED RESEARCH

This invention was made with government support under 16-CRHF-0-6055 and 17-CRHF-0-6055 awarded by the USDA/NIFA, under 1253634 awarded by the National Science Foundation, and under DE-FC02-07ER64494 and DE-SC0018409 awarded by the US Department of Energy. The government has certain rights in the invention.

SEQUENCE LISTING

This application is being filed electronically and includes an electronically submitted Sequence Listing in .txt format. The .txt file contains a sequence listing entitled "2019-08-01_960296-02452_SEQ_Listing.txt" created on Aug. 1, 2019 and is 10,439 bytes in size. The Sequence Listing contained in this .txt file is part of the specification and is hereby incorporated by reference herein in its entirety.

INTRODUCTION

Thermal tolerance is an important property in industrial yeast strains that influences the ability of these strains to produce important fermentation products such as beverages, biochemicals, and biofuels. For example, in the beer industry, more than 90% of the beer market consists of lagers, which are brewed with industrial hybrids of *Saccharomyces cerevisiae*×*Saccharomyces eubayanus*. *S. cerevisiae* has been extensively used in fermentation for thousands of years, including in ale production, but pure strains of *S. eubayanus* were not discovered until 2011. Since then, it has become clear that aggressive fermentation of the sugars present in wort are mainly conferred by *S. cerevisiae* genes, whereas the hallmark cold tolerance of lager strains are mainly conferred by *S. eubayanus* genes, with both traits being co-dominant in hybrids. Although brewing strains with colder thermal profiles may be desirable to minimize the production of off-flavors, it often is desirable to conduct fermentations at higher temperatures so as to reduce fermentation times and infrastructure investments. Other than conventional breeding and selection, the inventors are not aware of any other ways to directly manipulate the thermal tolerance of industrial or synthetic yeast strains, such as lager-brewing hybrids. There is thus a need in the art for new methods of altering the thermal tolerance in yeast strains.

SUMMARY

In one aspect of the present invention, methods of making a hybrid yeast strain having a selected mitotype are provided. The methods may include treating a first yeast strain with a mitochondrial genome elimination agent to produce a first mitochondrial genome-null yeast strain, and mating the first mitochondrial genome-null yeast strain with a second yeast strain comprising mitochondrial DNA (mtDNA) to produce the yeast strain having the selected mitotype.

In another aspect, the present invention relates to methods of making a yeast strain with an altered mitotype. The methods may include treating a first polyploid yeast strain with a mitochondrial genome elimination agent to produce a first mitochondrial genome-null yeast strain, and mating the first mitochondrial genome-null yeast strain with a second karyogamy-deficient yeast strain comprising mitochondrial DNA (mtDNA) to produce the yeast strain having the altered mitotype. In some embodiments of these methods, the mtDNA is supplied by a third, donor yeast strain.

In a further aspect of the present invention, yeast strains are provided. The yeast strains may include any yeast strain made by one of the methods disclosed herein.

In another aspect, the present invention relates to *Saccharomyces cerevisiae*×*Saccharomyces eubayanus* hybrids comprising mitochondrial DNA (mtDNA) from *Saccharomyces cerevisiae*. Optionally, the *Saccharomyces cerevisiae*×*Saccharomyces eubayanus* hybrids may be derived from a lager-brewing strain and include at least 50%, 55%, 60%, 65%, 70%, 75%, 80%, 85%, 90%, 95%, 96%, 97%, 98%, 99%, or 100% of their mitochondria or mtDNA from *Saccharomyces cerevisiae*.

In another aspect, the present invention relates to synthetic *Saccharomyces cerevisiae*×*Saccharomyces eubayanus* hybrids comprising mitochondrial DNA (mtDNA) from *Saccharomyces eubayanus*. Optionally, the *Saccharomyces cerevisiae*×*Saccharomyces eubayanus* hybrids may be derived from a lager-brewing strain. The hybrids may include at least 50%, 55%, 60%, 65%, 70%, 75%, 80%, 85%, 90%, 95%, 96%, 97%, 98%, 99%, or 100% of their mitochondria or mtDNA from *Saccharomyces eubayanus*. Alternatively, the hybrids may include at least 50%, 55%, 60%, 65%, 70%, 75%, 80%, 85%, 90%, 95%, 96%, 97%, 98%, 99%, or 100% of its mitochondria or mtDNA from *Saccharomyces cerevisiae*.

In another aspect, the present invention relates to new *Saccharomyces cerevisiae* strains having *Saccharomyces eubayanus* mitotypes. The *Saccharomyces cerevisiae* strains may include genomic DNA and mitochondrial DNA (mtDNA), wherein at least 50%, 55%, 60%, 65%, 70%, 75%, 80%, 85%, 90%, 95%, 96%, 97%, 98%, 99%, or 100% of the genomic DNA is from *Saccharomyces cerevisiae* and wherein at least 50%, 55%, 60%, 65%, 70%, 75%, 80%, 85%, 90%, 95%, 96%, 97%, 98%, 99%, or 100% of the mtDNA is from *Saccharomyces eubayanus*.

In another aspect, the present invention relates to new *Saccharomyces eubayanus* strains having *Saccharomyces cerevisiae* mitotypes. The *Saccharomyces eubayanus* strains may include genomic DNA and mitochondrial DNA (mtDNA), wherein at least 50%, 55%, 60%, 65%, 70%, 75%, 80%, 85%, 90%, 95%, 96%, 97%, 98%, 99%, or 100% of the genomic DNA is from *Saccharomyces eubayanus* and wherein at least 50%, 55%, 60%, 65%, 70%, 75%, 80%, 85%, 90%, 95%, 96%, 97%, 98%, 99%, or 100% of the mtDNA is from *Saccharomyces cerevisiae*.

In a still further aspect, the present invention relates to methods for making a fermentation product. The methods may include culturing any one of the yeast strains described herein, any one of the *Saccharomyces cerevisiae*×*Saccharomyces eubayanus* hybrids disclosed herein, any one of the synthetic *Saccharomyces cerevisiae*×*Saccharomyces eubayanus* hybrids disclosed herein, any one the *Saccharomyces cerevisiae* strains disclosed herein, or any one of the Saccharomyces eubayanus strains disclosed herein with a fermentable substrate and at a temperature to produce the fermentation product.

BRIEF DESCRIPTION OF THE DRAWINGS

FIGS. 1A and 1B) Relative growth of parent strains carrying their native mtDNA on glucose and glycerol, respectively. FIGS. 1C and 1D) Relative growth of S. cerevisiae×S. eubayanus hybrids carrying different parental mtDNA on glucose and glycerol, respectively. Error bars represent standard error. Differences in relative growth between hybrids carrying different parental mtDNA with p-values of <0.05 were considered statistically significant and are represented by an asterisk. Parents were not tested for significant differences.

FIG. 2A) Outline of crosses and strain engineering to produce lager cybrids. Yeast cells represent the nuclear genome, large inner circles represent mtDNA, and small inner circles represent the HyPr plasmid. Lower case "a" and "α" indicates mating type. FIGS. 2B and 2C) Growth of a lager strain with native (S. eubayanus) mtDNA and lager cybrids with S. cerevisiae mtDNA. Error bars represent standard error and asterisks indicate statistically significant differences in growth between the cybrid and lager with native mtDNA (p-value <0.05). FIG. 2B) Growth on glucose FIG. 2C) Growth on glycerol.

FIGS. 4A-4C. Sc×Se growth assay. Growth assay for S. cerevisiae (laboratory strain)×S. eubayanus (type strain) hybrids and parental strains. FIG. 4A) Representative spot assay plates grown at various temperatures on plates containing glucose or glycerol as the sole carbon source. The following strains were tested: S. cerevisiae (Sc) $\rho^+$ parent, Sc $\rho^0$ parent, S. eubayanus (Se) $\rho^+$ parent, Se $\rho^0$ parent, Sc $\rho^+$×Se $\rho^0$ hybrid, and Sc $\rho^0$×Se $\rho^+$ hybrid. FIGS. 4B and 4C) Relative growth of tested strains across all temperatures, combining all replicates. Outer circles and lines represent nuclear genotype, while inner circles represent mtDNA. Shaded regions represent temperatures where a hybrid of one mitotype had significantly greater relative growth than the hybrid with the alternative mitotype. FIG. 4B) Relative growth of tested strains on glucose. FIG. 4C) Relative growth of tested strains on glycerol.

FIG. 5A) Representative spot assay plates grown at various temperatures on plates containing glucose or glycerol as the sole carbon source. The following strains were tested: S. cerevisiae-ale (ScAle) $\rho^+$ parent, ScAle $\rho^0$ parent, S. eubayanus (Se) $\rho^+$ parent, Se $\rho^0$ parent, ScAle $\rho^+$×Se $\rho^0$ hybrid, and ScAle $\rho^0$×Se $\rho^+$ hybrid. FIGS. 5B and 5C) Relative growth of tested strains across all temperatures, combining all replicates. Outer circles and lines represent nuclear genotype, while inner circles represent mtDNA. Shaded regions represent temperatures where a hybrid of one mitotype had significantly greater relative growth than the hybrid with the alternative mitotype. FIG. 5B) Relative growth of tested strains on glucose. FIG. 5C) Relative growth of tested strains on glycerol.

FIG. 6A) Representative spot assay plates grown at various temperatures on plates containing glucose or glycerol as the sole carbon source. The following strains were tested: S. cerevisiae (Sc) $\rho^+$ parent, Sc $\rho^0$ parent, S. eubayanus—North Carolina (SeNC) $\rho^+$ parent, SeNC $\rho^0$ parent, Sc $\rho^+$×SeNC $\rho^0$ hybrid, and Sc $\rho^0$×SeNC $\rho^+$ hybrid. FIGS. 6B and 6C) Relative growth of tested strains across all temperatures, combining all replicates. Outer circles and lines represent nuclear genotype, while inner circles represent mtDNA. Shaded regions represent temperatures where a hybrid of one mitotype had significantly greater relative growth than the hybrid with the alternative mitotype. FIG. 6B) Relative growth of tested strains on glucose. FIG. 6C) Relative growth of tested strains on glycerol.

FIG. 7A) Representative spot assay plates grown at various temperatures on plates containing glucose or glycerol as the sole carbon source. The following strains were tested: S. cerevisiae-ale (ScAle) $\rho^+$ parent, ScAle $\rho^0$ parent, S. eubayanus—North Carolina (SeNC) $\rho^+$ parent, SeNC $\rho^0$ parent, ScAle $\rho^+$×SeNC $\rho^0$ hybrid, and ScAle $\rho^0$×SeNC $\rho^+$ hybrid. FIGS. 7B and 7C) Relative growth of tested strains across all temperatures, combining all replicates. Outer circles and lines represent nuclear genotype, while inner circles represent mtDNA. Shaded regions represent temperatures where a hybrid of one mitotype had significantly greater relative growth than the hybrid with the alternative mitotype. FIG. 7B) Relative growth of tested strains on glucose. FIG. 7C) Relative growth of tested strains on glycerol.

FIG. 8A) Representative spot assay plates grown at various temperatures on plates containing glucose or glycerol as the sole carbon source. The following strains were tested: lager $\rho^+$ parent, lager $\rho^0$ parent, S. cerevisiae (laboratory strain) (Sc) $\rho^+$ parent, S. cerevisiae-ale (ScAle) $\rho^+$ parent, lager $\rho^{Sc}$ cybrid, and lager $\rho^{ScAle}$ cybrid. FIGS. 8B and 8C) Relative growth of tested strains across all temperatures combining all replicates. Error bars represent standard error and asterisks indicate statistically significant differences in growth between the cybrid and lager with native mtDNA (p<0.05). FIG. 8B) Relative growth of tested strains, excluding lager $\rho^0$, on glucose. FIG. 8C) Relative growth of tested strains, excluding lager $\rho^0$, on glycerol.

DETAILED DESCRIPTION

Figure 1A:
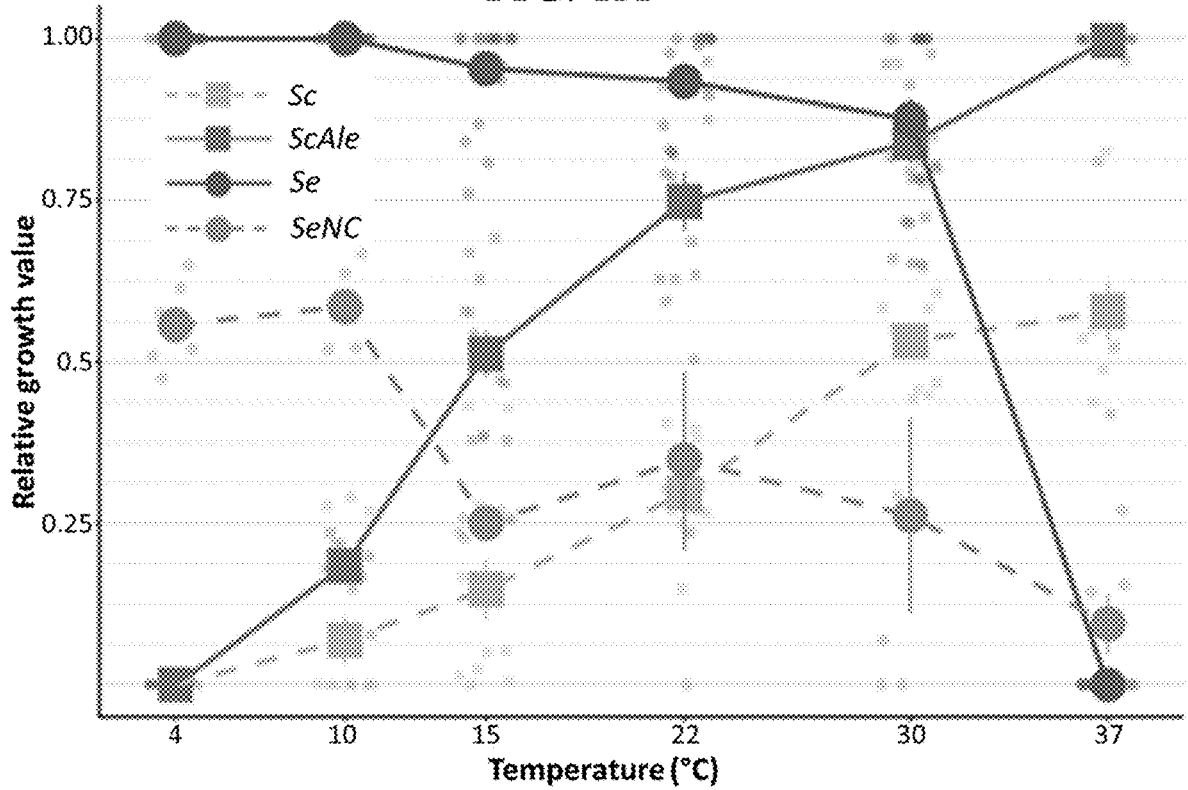
FIGS. 1A-1D. Relative growth of S. cerevisiae, S. eubayanus, and their hybrids. Graphs of relative growth scores of strains, combined from all tests.

When two yeast cells mate, the mitochondrial genome (mtDNA) of both parents is initially present in the zygote. However, within a few cell divisions, a single mtDNA haplotype, or "mitotype" is fixed (Berger and Yaffe 2000), often in a non-random manner (Zweifel and Fangman 1991; Marinoni et al. 1999; Hsu and Chou 2017). In the present application, the inventors demonstrate that the thermal tolerance of yeast is dictated by mitotype and provide methods for controlling or selecting the mitotype. Thus, the ability to control the inheritance of mtDNA allows one to adapt yeast for growth at various temperatures. This ability is a powerful tool for the generation of novel yeast with utility in numerous applications.

The present invention provides new yeast strains with selected mitotypes and new methods for altering or selecting the mitotype of yeast. The inventors have shown that the thermal tolerance of *S. cerevisiae* strains, *S. eubayanus* strains, and hybrids of these species can be controlled by manipulating the parental source of the mtDNA. Specifically, in the non-limiting Examples, the inventors demonstrate that *S. cerevisiae*×*S. eubayanus* strains with *S. cerevisiae* mtDNA perform better at warmer temperatures, while *S. cerevisiae*×*S. eubayanus* strains with *S. eubayanus* mtDNA perform better at colder temperatures. The inventors further show that the thermal profiles of existing industrial lager strains can be manipulated analogously by depleting and replacing the mitochondria of the strains through, for example, cytoduction using a strain of *S. cerevisiae* that can transfer mtDNA to another strain without completing karyogamy. Lager yeast strains with elevated thermal tolerance may be attractive to the lager-brewing industry because they are expected to reduce fermentation times and infrastructure investments. Reduced fermentation times are attractive across all production scales, whereas infrastructure investments are a major obstacle to lager brewing among microbreweries that generally favor ale brewing partly for this reason.

Methods of Making Hybrid Yeast Strains with Selected Mitotypes

In one aspect of the present invention, methods of making a yeast strain having a selected mitotype are provided. The methods include treating a first yeast strain with a mitochondrial genome elimination agent to produce a first mitochondrial genome-null yeast strain, and mating the first mitochondrial genome-null yeast strain with a second yeast strain comprising mitochondrial DNA to produce the yeast strain having the selected mitotype.

As used herein, the description "comprising mitochondrial DNA" implies that the yeast contain untreated, replication competent mitochondria comprising intact mitochondrial genomes.

As used herein, "mating" refers to the process of fusing together at least one yeast cell from a first yeast strain with at least one yeast cell from a second yeast strain. Mating may or may not entail karyogamy, or the fusing together of the nuclei in the two parental yeast cells. However, in this particular set of methods, mating produces a "hybrid" yeast strain, which comprises nuclear DNA contributed from both parental strains, as opposed to a cybrid. A "cybrid" is a cell in which the original mitochondrial are substituted with their counterparts from another strain or species using a method such as cytoduction (described below). Thus, a cybrid comprises the nuclear DNA of a single parent yeast cell and the mitochondria of a second donor yeast cell.

Haploid yeast strains with the appropriate mating types may mate naturally. Thus, in preferred embodiments of these methods, two haploid yeast strains are mated to produce a new hybrid yeast strain with the selected mitotype.

As used herein, "mitotype" refers to the parental yeast strain from which the mitochondrial DNA in a yeast strain originated. For example, if a *Saccharomyces cerevisiae* yeast strain having mitochondria (and mtDNA) is mated with *Saccharomyces eubayanus* that lacks mtDNA, the resulting hybrid yeast strain will have a *Saccharomyces cerevisiae* "mitotype" (i.e., mtDNA originated from the *Saccharomyces cerevisiae* parent).

As used herein, "treating" refers to contacting, for example, a yeast strain, with a particular substance or substances. Contacting encompasses administration to a cell directly or adding an agent to a culture comprising the yeast. As used herein, a "mitochondrial genome elimination agent" refers to an agent that disrupts yeast mitochondrial DNA, allowing the mitochondrial genome of a yeast strain to be removed. To control the inheritance of mtDNA during yeast mating, the present inventors generated "mitochondrial genome-null yeast strains" ($\rho^0$) (mtDNA completely absent) to mate with strains having mitochondria ($\rho^+$) so that mtDNA from only the $\rho^+$ parent would be present in offspring. See, e.g., FIG. 3. In the non-limiting Examples, mitochondrial genome-null yeast strains ($\rho^0$) were generated by treating $\rho^+$ parent strains with ethidium bromide to generate respiration-deficient strains. Respiration-deficient strains were screened for by the absence of growth on glycerol, and the complete removal of mtDNA was confirmed by DAPI staining. Suitable "mitochondrial genome elimination agents" in accordance with the present invention may include, without limitation, ethidium bromide or antifolate cocktails that include methotrexate and sulfanilamide RRR.

The first yeast strain and the second yeast strain of the present method may be the same or different yeast species (defined below). In some embodiments, the first yeast strain may be the same yeast species as the second yeast strain but be a different strain of that yeast species. In certain embodiments, the methods are used to create synthetic "lager hybrids" of *Saccharomyces cerevisiae*×*Saccharomyces eubayanus* with selected mitotypes. In one preferred embodiment, the first yeast strain is *Saccharomyces cerevisiae* and the second yeast strain is *Saccharomyces eubayanus*. In a second preferred embodiment, the first yeast strain is *Saccharomyces eubayanus* and the second yeast strain is *Saccharomyces cerevisiae*.

Methods of Making Polyploid Cybrids

In another aspect, the present invention provides methods of making a polyploid cybrid yeast strain with an altered mitotype. These methods involve treating a first polyploid yeast strain with a mitochondrial genome elimination agent to produce a first mitochondrial genome-null "acceptor" yeast strain, and mating the acceptor yeast strain with a second "shuttle" yeast strain comprising mitochondrial DNA (mtDNA). The shuttle yeast strain must be a karyogamy-deficient yeast strain, such that the resulting yeast strain with an altered mitotype is a "cybrid" comprising nuclear DNA of the acceptor yeast strain and the mtDNA delivered in the cytoplasm of the shuttle yeast strain.

A "karyogamy-deficient yeast strain" refers to a yeast strain that may not perform karyogamy or the fusing together of the nuclei in the two parental yeast cells. The "karyogamy-deficient yeast strain" may include mutations in genes required for karyogamy including, without limitation, a kar1-1 mutation. In the present invention, mating the first acceptor yeast strain to a second karyogamy-deficient yeast strain allows for mixing of cytoplasm between the mated cells, while preventing fusion between the nuclear genomes, ultimately leading to progeny with mixed cytoplasm, but only one nuclear background. In this way, the mitochondria from the shuttle strain may be transferred into the mitochondrial genome-null acceptor yeast strain by mating the yeast and selecting for functional mtDNA (by growth on glycerol, a non-fermentable carbon source) and nuclear background of the acceptor yeast strain. This transfer of mitochondria from one cell to another is referred to as "cytoduction".

In certain embodiments, the karyogamy-deficient shuttle strain may deliver its native mitochondria (or mitochondrial DNA) to the acceptor strain. In other embodiments, the shuttle strain may deliver mitochondria from a "donor" yeast strain. The donor mitochondria may be introduced into the shuttle yeast strain by mating the donor yeast strain with the shuttle strain (see, e.g., FIG. 2A). In this way, the mitochondria from the donor strain may be transferred into the shuttle strain, forming a cybrid with the desired mitotype by cytoduction. Including this optional, additional step before the shuttle strain is mated with the acceptor yeast strain allows the mitochondria of any suitable yeast strain to ultimately be transferred to the acceptor yeast strain. Thus, using this two-step cytoduction method, any yeast cell with a desirable genome (i.e., the acceptor yeast strain) may be altered to have any desirable mitotype (either that of the shuttle or the donor strain). For instance, in the Examples, the applicants demonstrate that by replacing the mitochondria of an acceptor yeast strain of *Saccharomyces eubayanus* origin (a lager strain) with the mitochondria of a *Saccharomyces cerevisiae* donor strain via a karyogamy-deficient *Saccharomyces cerevisiae* shuttle strain, a cybrid lager yeast strain with elevated thermal tolerance may be produced.

Importantly, the acceptor yeast strains of the present invention may be any polyploid yeast strain. As used herein, "polyploid" refers to cells with multiple sets of chromosomes. Thus, a polyploid yeast strain has a genome that is of diploid or higher ploidy (i.e., diploid (2N), triploid (3N), tetraploid (4N), pentaploid (5N), hexaploid (6N), heptaploid (7N), octaploid (8N), nonaploid (9N), decaploid (10N), 11N, 12N, 13N, 14N, 15N, 16N, or more). Preferably, the acceptor yeast strain are allopolyploid. As used herein, "allopolyploid" refers to hybrid cells with two or more sets of chromosomes derived from two different species. This definition includes allodiploids, allotriploids, allotetraploids, allopentaploids, allohexaploids, and allopolyploids with a higher number of haploid sets.

The inventors envision that these methods can be used to alter industrial lager strains, such as *Saccharomyces pastorianus* and *Saccharomyces carlsbergensis*, to adapt them for fermentation at various temperatures. Because these strains have complex allopolyploid genomes, it is challenging to work with them using traditional genetic methods. Mating does not usually occur in polyploid yeasts because they contain both MATa and MATα at their mating type locus. Thus, to mate polyploid strains for cytoduction, the MAT locus must first be homozygosed. In certain embodiments, this is accomplished using the the HyPr method, which is detailed in U.S. Patent Publication 2018/0127784, the contents of which is incorporated herein in its entirety. For instance, in the Examples, the MAT locus of lager genome-null acceptor strains was homozygosed using a HyPr (Hybrid Production) plasmid (pHCT2). Briefly, a "HyPr plasmid" may include a polynucleotide comprising a promoter operably connected to an HO polynucleotide encoding a yeast Ho protein, a selectable marker cassette, and a yeast origin of replication.

The terms "promoter," "promoter region," or "promoter sequence" refer generally to transcriptional regulatory regions of a gene, which may be found at the 5' or 3' side of a gene such as the HO polynucleotide, or within the coding region of the gene (i.e., HO polynucleotide). Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

In some embodiments, the promoters within the polynucleotides of the present invention may be operably connected to the HO polynucleotide. As used herein, a promoter is "operably connected to" or "operably linked to" when it is placed into a functional relationship with a second polynucleotide sequence. For instance, a promoter is operably connected to an HO polynucleotide if the promoter is connected to the HO polynucleotide such that it may effect transcription of the HO polynucleotide coding sequence. In various embodiments, the HO polynucleotides may be operably linked to at least 1, at least 2, at least 3, at least 4, at least 5, or at least 10 promoters.

Promoters useful in the practice of the present invention include, but are not limited to, constitutive, inducible, temporally-regulated, and chemically regulated promoters. Preferably, the promoters are inducible. Suitable inducible promoters for expression in yeast include, without limitation, galactose inducible promoters (i.e., GAL1) and doxycycline-inducible promoters. Those of skill in the art are familiar with a wide variety of additional promoters for use in various yeast species.

The HyPr plasmid may include an HO polynucleotide encoding a yeast Ho protein. Yeast Ho proteins are site-specific endonucleases that produce a double-strand break in the MAT locus. The double-strand break is followed by a unidirectional gene conversion event that replaces the information at the MAT locus by information copied from either of the two homologous loci (HMR and HML) or from another copy of the MAT locus. Alternatively, the cut chromosome may by lost, leading to a mating type change. Yeast Ho proteins may be any of the Ho proteins found in any yeast species including, without limitation, those yeast species closely related to *Candida glabrata* and *Naumovozyma castellii*. Suitably, the protein sequence of an exemplary yeast Ho protein from *Saccharomyces cerevisiae* is indicated in SEQ ID NO: 14. In some embodiments, the yeast Ho protein comprises SEQ ID NO: 11 or a mutant, variant, derivative, or fragment thereof.

As used herein, a "protein," "polypeptide," or "peptide" may be used interchangeably to refer to a polymer of amino acids. A "protein" as contemplated herein typically comprises a polymer of naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine).

A yeast Ho protein may include "mutant" proteins, variants, and derivatives thereof. As used herein the term "wild-type" is a term of the art understood by skilled persons and means the typical form of an organism, strain, gene, or characteristic as it occurs in nature as distinguished from mutant or variant forms. As used herein, a "variant," "mutant," or "derivative" refers to a polypeptide molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a yeast Ho protein mutant or variant protein may have one or more insertions, deletions, or substitution of at least one amino acid residue relative to the yeast Ho "wild-type" protein. The protein sequences of a "wild-type" yeast Ho protein from *Saccharomyces cerevisiae* is presented as SEQ ID NO: 14. This sequence may be used as a reference sequence.

A yeast Ho protein may be a full-length protein or may be fragments of the full-length protein. As used herein, a "fragment" is a portion of an amino acid sequence, which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference protein, respectively. In some embodiments, a fragment may comprise at least 5, 10, 15, 20, 25, 30, 40, 50, 60, 70, 80, 90, 100, 150, 250, or 500 contiguous amino acid residues of a reference protein. Fragments may be preferentially selected from certain regions of a molecule. The term "at least a fragment" encompasses the full-length polypeptide. A fragment may include an N-terminal truncation, a C-terminal truncation, or both truncations relative to the full-length yeast Ho protein. Preferably, a fragment of a yeast Ho protein includes amino acid residues required for recognition and cleavage of the MAT locus site.

A "deletion" in a yeast Ho protein refers to a change in the amino acid sequence resulting in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide).

"Insertions" and "additions" in a yeast Ho protein refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A variant of a yeast Ho protein may have N-terminal insertions, C-terminal insertions, internal insertions, or any combination of N-terminal insertions, C-terminal insertions, and internal insertions.

Regarding proteins, the phrases "percent identity," "% identity," and "% sequence identity" refer to the percentage of residue matches between at least two amino acid sequences aligned using a standardized algorithm. Methods of amino acid sequence alignment are well known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases. As described herein, variants, mutants, or fragments (e.g., a yeast Ho protein variant, mutant, or fragment thereof) may have 99%, 98%, 97%, 96%, 95%, 94%, 93%, 92%, 91%, 90%, 80%, 70%, 60%, or 50% amino acid sequence identity relative to a reference molecule (e.g., relative to a full-length yeast Ho protein (SEQ ID NO: 14)).

Protein sequence identity may be measured over the length of an entire defined protein sequence, for example, as defined by a particular SEQ ID number, or may be measured over a shorter length, for example, over the length of a fragment taken from a larger, defined protein sequence, for instance, a fragment of at least 15, at least 20, at least 30, at least 40, at least 50, at least 70, or at least 150 contiguous residues. Such lengths are exemplary only, and it is understood that any fragment length supported by the sequences shown herein, in the tables, figures or Sequence Listing, may be used to describe a length over which percentage identity may be measured.

The amino acid sequences of the yeast Ho protein variants, mutants, or derivatives as contemplated herein may include conservative amino acid substitutions relative to a reference amino acid sequence. For example, a variant, mutant, or derivative polypeptide may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The HO polynucleotides encoding the yeast Ho proteins, fragments, variants, mutants, or derivatives thereof may be any polynucleotide encoding the appropriate yeast Ho protein amino acid sequence. Those of skill in the art also understand the degeneracy of the genetic code and that a variety of polynucleotides can encode the same polypeptide. In some embodiments, the polynucleotides may be codon-optimized for expression in a particular yeast cell. While particular nucleotide sequences, which are found in *Saccharomyces cerevisiae* (i.e., SEQ ID NO: 15), are disclosed, herein any nucleotide sequences may be used which encode a desired form of the yeast Ho proteins described herein. Thus, non-naturally occurring sequences may be used. These may be desirable, for example, to enhance expression in a particular yeast species. Computer programs for generating degenerate coding sequences are available and can be used for this purpose as well as other means.

The HyPr plasmid may also include a selectable marker cassette. The selectable marker cassette may confer resistance to nourseothricin (natMX4) or hygromycin (hphMX). Other selectable markers conferring resistance to other antibiotics, such as kanMX, amdS, TK, Sh ble or ble, which confer resistance to G418, fluoroacetamide, antifolates, Zeocin or phleomycin, respectively, could also be used. Those of skill in the art will appreciate that additional combinations of selectable markers can be used as well. Other forms of selectable markers may be used such as markers that provide a growth advantage or colorimetric selection other than antibiotic resistance. The selectable marker cassettes include a polynucleotide encoding the selectable marker operably connected to a promoter capable of inducing transcription of the selectable marker.

The HyPr plasmid may also include a yeast origin of replication to allow replication of the polynucleotides in a particular yeast species. Suitably, the yeast origin of replication is functional across many yeast species including, without limitation, all *Saccharomyces* species. Exemplary yeast origin of replications may include, without limitation, KARS101 from *Kluyveromyces lactis* and *S. cerevisiae* CEN and ARS sequences to improve stability in multiple yeast species.

The "yeast strains" used in any method of the present invention (i.e., first yeast strain, second yeast strain, acceptor yeast strain, karyogamy-deficient shuttle yeast strain, donor yeast strain) may be from the family Saccharomycetaceae. In some embodiments, the yeast strains are from the genus *Saccharomyces*. Suitable *Saccharomyces* species may include, without limitation, *Saccharomyces cerevisiae*, *Saccharomyces eubayanus*, *Saccharomyces paradoxus*, *Saccharomyces mikatae*, *Saccharomyces jurei*, *Saccharomyces arboricola*, *Saccharomyces bayanus*, *Saccharomyces pastorianus*, *Saccharomyces carlsbergensis*, *Saccharomyces kudriavzevii*, and *Saccharomyces uvarum*. Suitable *Saccharomyces* species may also include any taxonomic synonyms of these species or any newly discovered species to be members of the genus *Saccharomyces*. Suitable yeast strains may include those that are cold adapted, such as *Saccharomyces bayanus*, *Saccharomyces kudriavzevii*, *Saccharomyces pastorianus*, *Saccharomyces carlsbergensis*, *Saccharomyces uvarum*, and *Saccharomyces eubayanus*. Suitable yeast strains may also include yeast hybrids including, without limitation, *Saccharomyces cerevisiae*×*Saccharomyces eubayanus* hybrids. Throughout the present application, the nomenclature Species 1×Species 2 will be used to refer to interspecies hybrids (as suggested by Nguyen and Boekhout, 2017). In certain preferred embodiments, the yeast strain is a *Saccharomyces cerevisiae*×*Saccharomyces eubayanus* hybrid, including those commonly used in the beer industry, including *Saccharomyces bayanus*, *Saccharomyces pastorianus*, and *Saccharomyces carlsbergensis*).

A "yeast species," as used herein, may refer to a substantially pure yeast species or to a yeast strain that is a mixed yeast species. A substantially pure yeast species may contain greater than 95%, 96%, 97%, 98%, 99%, or 99.9% chromosomal content from a single yeast species. For example, strains of *Saccharomyces cerevisiae* that contain greater than 95%, 96%, 97%, 98%, 99%, or 99.9% *Saccharomyces cerevisiae* chromosomal content may be considered a substantially pure yeast species and would be considered to be a *Saccharomyces cerevisiae* species. A mixed yeast species may contain substantial chromosomal content from 2 or more different yeast species. For example, a particular yeast strain may have 90% chromosomal content from *Saccharomyces uvarum* and 5% chromosomal content from *Saccharomyces cerevisiae* and 5% chromosomal content from *Saccharomyces eubayanus*. In the case of mixed species, and in accordance with the present invention, the yeast species of a yeast cell from a mixed yeast species is determined by which species contributes the majority of the chromosomal content in the cell. Thus, in the preceding mixed species example, the exemplary yeast strain would be considered a *Saccharomyces uvarum* species.

As used herein, a "different yeast species" refers to yeast species that are not the same as determined in view of the "yeast species" definitions provided herein. For example, if the first yeast species was a yeast strain having 90% chromosomal content from *Saccharomyces uvarum* and 5% chromosomal content from *Saccharomyces cerevisiae* and 5% chromosomal content from *Saccharomyces eubayanus* and the second yeast species was a substantially pure *Saccharomyces uvarum* strain, the first yeast species and the second yeast species would be considered the same—*Saccharomyces uvarum*. Examples of embodiments where the first yeast species and the second yeast species would be considered different might include the first yeast species being *Saccharomyces cerevisiae* and the second yeast species being *Saccharomyces eubayanus*. In some embodiments, the first yeast strain is *Saccharomyces cerevisiae* and the second yeast strain is *Saccharomyces eubayanus*. In some embodiments, the first yeast strain is *Saccharomyces eubayanus* and the second yeast strain is *Saccharomyces cerevisiae*.

Compositions ("Yeast Strains")

In a further aspect of the present invention, yeast strains are provided. The yeast strains may include any yeast strains made by one of the methods disclosed herein.

In another aspect, the present invention relates to *Saccharomyces cerevisiae*×*Saccharomyces eubayanus* hybrids comprising mitochondrial DNA (mtDNA) from *Saccharomyces cerevisiae*. Lager style beers are fermented at low temperatures, and it has been known for some time that lager yeasts inherited the ability to ferment at these low temperatures from their *S. eubayanus* parent. Lager hybrids also inherited their mtDNA from the *S. eubayanus* parent. The present inventors, however, have been able to alter the mitotype of lager hybrid strains from a *Saccharomyces eubayanus* mitotype to a *Saccharomyces cerevisiae* mitotype. Such lager hybrid strains have superior growth over lager hybrid strains with *S. eubayanus* mtDNA when grown at high temperatures. See, e.g. Examples.

The *Saccharomyces cerevisiae*×*Saccharomyces eubayanus* hybrids including mitochondria or mitochondrial DNA (mtDNA) from *Saccharomyces cerevisiae* may include at least 50%, 55%, 60%, 65%, 70%, 75%, 80%, 85%, 90%, 95%, 96%, 97%, 98%, 99%, or 100% of its mitochondria or mtDNA from *Saccharomyces cerevisiae*. Suitably, the *Saccharomyces cerevisiae*×*Saccharomyces eubayanus* hybrid may include all of its mitochondria or mitochondria DNA (mtDNA) from *Saccharomyces cerevisiae*.

The present invention also encompasses synthetic *Saccharomyces cerevisiae*×*Saccharomyces eubayanus* hybrids with mitochondrial DNA (mtDNA) from *Saccharomyces eubayanus*. As used herein, "synthetic" refers to hybrids that may be produced using laboratory methods as opposed to those hybrids found in nature. The present inventors envision that the methods disclosed herein may also be used to generate new synthetic *Saccharomyces cerevisiae*×*Saccharomyces eubayanus* hybrids having new *Saccharomyces eubayanus* mitotypes that may be expected to produce lager beers at new optimal temperatures or lower temperatures.

The synthetic *Saccharomyces cerevisiae*×*Saccharomyces eubayanus* hybrids including mitochondria or mitochondrial DNA (mtDNA) from *Saccharomyces eubayanus* may include at least 50%, 55%, 60%, 65%, 70%, 75%, 80%, 85%, 90%, 95%, 96%, 97%, 98%, 99%, or 100% of its mitochondria or mtDNA from *Saccharomyces eubayanus*. Suitably, the synthetic *Saccharomyces cerevisiae*×*Saccharomyces eubayanus* hybrid may include all of its mitochondria or mitochondria DNA (mtDNA) from *Saccharomyces eubayanus*.

In some embodiments, the "*Saccharomyces cerevisiae*×*Saccharomyces eubayanus*" or "synthetic *Saccharomyces cerevisiae*×*Saccharomyces eubayanus*" hybrid is or may be derived from a lager-brewing strain. As used herein, a "lager-brewing strain" refers to a *Saccharomyces cerevisiae*×*Saccharomyces eubayanus* hybrid strains historically used in the production of lager style beers, such as *Saccharomyces pastorianus* and *Saccharomyces carlsbergensis*. The lager-brewing strains may have a *Saccharomyces eubayanus* mitotype. In another aspect, the present invention relates to new *Saccharomyces cerevisiae* strains having *Saccharomyces eubayanus* mitotypes. The *Saccharomyces cerevisiae* strains may include genomic DNA and mitochondrial DNA (mtDNA), wherein at least 50%, 55%, 60%, 65%, 70%, 75%, 80%, 85%, 90%, 95%, 96%, 97%, 98%, 99%, or 100% of the genomic DNA is from *Saccharomyces cerevi-*

*siae* and wherein at least 50%, 55%, 60%, 65%, 70%, 75%, 80%, 85%, 90%, 95%, 96%, 97%, 98%, 99%, or 100% of the mtDNA is from *Saccharomyces eubayanus*.

In another aspect, the present invention relates to new *Saccharomyces eubayanus* strains having *Saccharomyces cerevisiae* mitotypes. The *Saccharomyces eubayanus* strains may include genomic DNA and mitochondrial DNA (mtDNA), wherein at least 50%, 55%, 60%, 65%, 70%, 75%, 80%, 85%, 90%, 95%, 96%, 97%, 98%, 99%, or 100% of the genomic DNA is from *Saccharomyces eubayanus* and wherein at least 50%, 55%, 60%, 65%, 70%, 75%, 80%, 85%, 90%, 95%, 96%, 97%, 98%, 99%, or 100% of the mtDNA is from *Saccharomyces cerevisiae*.

Methods of Making a Fermentation Product

In a still further aspect, the present invention relates to methods for making a fermentation product. The methods may include the culturing any one of the yeast strains described herein (see "Compositions" section above), any one of the *Saccharomyces cerevisiae*×*Saccharomyces eubayanus* hybrids disclosed herein, any one of the synthetic *Saccharomyces cerevisiae*×*Saccharomyces eubayanus* hybrids disclosed herein, any one the *Saccharomyces cerevisiae* strains disclosed herein, or any one of the *Saccharomyces eubayanus* strains disclosed herein with a fermentable substrate and at a temperature to produce the fermentation product.

As used herein, "culturing" refers to mixing the yeast strains or *Saccharomyces cerevisiae*×*Saccharomyces eubayanus* hybrids into any medium including a fermentable substrate. The fermentable substrate may include a carbohydrate, wort, and/or malt extract.

The fermentation product may be a beer product, a wine product, an alcoholic beverage, a biochemical, or a biofuel. In some embodiments, the fermentation product is a lager beer.

The yeast strains or *Saccharomyces cerevisiae*×*Saccharomyces eubayanus* hybrid may be cultured at a temperature at, below, or above 36° F., 37° F., 38° F., 39° F., 40° F., 41° F., 42° F., 43° F., 44° F., 45° F., 46° F., 47° F., 48° F., 49° F., 50° F., 51° F., 52° F., 53° F., 54° F., 55° F., 56° F., 57° F., 58° F., 59° F., 60° F., 61° F., 62° F., 63° F., 64° F., 65° F., 66° F., 67° F., 68° F., 69° F., 70° F., 75° F., 80° F., 85° F., 90° F., 95° F., or 100° F. Suitably, the temperature may be between about 40° F. and about 50° F., about 50° F. and about 58° F., about 55° F. and about 60° F., about 56° F. and about 61° F., about 57° F. and about 62° F., about 58° F. and about 63° F., about 59° F. and about 64° F., about 60° F. and about 65° F., about 61° F. and about 66° F., about 62° F. and about 67° F., about 63° F. and about 68° F., about 64° F. and about 69° F., about 65° F. and about 70° F., about 66° F. and about 71° F., about 67° F. and about 72° F., about 68° F. and about 73° F., about 69° F. and about 74° F., about 70° F. and about 75° F., about 75° F. and about 80° F., about 80° F. and about 85° F., about 85° F. and about 90° F., about 90° F. and about 95° F., about 95° F. and about 100° F. or any range therein. In some embodiments, the temperature is between about 40° F. and about 100° F. or any range therein.

Suitably, in some embodiments, when the yeast strain or hybrid includes *Saccharomyces eubayanus* mitochondrial DNA (mtDNA), the yeast strain or hybrid is grown at temperatures below 60° F. or between about 40° F. and about 50° F., about 50° F. and about 58° F., about 55° F. and about 60° F., or any range therein.

Suitably, in some embodiments, when the yeast strain or hybrid includes *Saccharomyces cerevisiae* mitochondrial DNA (mtDNA), the yeast strain or hybrid is grown at temperatures above 60° F. or between about 60° F. and about 65° F., about 61° F. and about 66° F., about 62° F. and about 67° F., about 63° F. and about 68° F., about 64° F. and about 69° F., about 65° F. and about 70° F., about 66° F. and about 71° F., about 67° F. and about 72° F., about 68° F. and about 73° F., about 69° F. and about 74° F., about 70° F. and about 75° F., about 75° F. and about 80° F., about 80° F. and about 85° F., about 85° F. and about 90° F., about 90° F. and about 95° F., about 95° F. and about 100° F. or any range therein.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1—Impact of Mitochondria on Temperature Tolerance in Industrial and Synthetic Lager-Brewing Yeast Hybrids A growing body of observational and experimental data supports the role of mitochondria in thermal adaptation. In *Saccharomyces* yeasts, relatively little work has examined the role of mitochondrial DNA (mtDNA) in temperature tolerance, and most of this work has focused on tolerance to high temperatures. The yeasts of the genus *Saccharomyces* can be broadly divided between cryotolerant and thermotolerant species. The genetic and molecular basis of the ability to grow at low temperatures in cryotolerant *Saccharomyces* yeasts is still poorly understood and what role mtDNA may play has not been tested. The industrial yeast strains used in brewing lager-style beers were formed by hybridization between the thermotolerant species *Saccharomyces cerevisiae* and the cryotolerant species *Saccharomyces eubayanus* and inadvertently selected by brewers over numerous generations. Lager-style beers are fermented at low temperatures, and it has been known for some time that lager yeasts inherited the ability to ferment at these low temperatures from their *S. eubayanus* parent. Intriguingly, lager hybrids also inherited their mtDNA from the *S. eubayanus* parent. In the following study, we assayed the influence of parental mitotype on relative growth in synthetic *S. cerevisiae*×*S. eubayanus* hybrids across a wide range of temperatures. We also examined the impact of exchanging the native mtDNA present in an industrial lager-brewing hybrid with mtDNA from *S. cerevisiae*. In this way we demonstrated that mtDNA influences the growth of *Saccharomyces* hybrids, at both high and low temperatures, and showed a strong influence of mitotype in an industrial lager hybrid.

Suitable thermal tolerance is a critical component of how organisms adapt to their environment. Studies have begun to establish the link between variation in mitochondrial DNA (mtDNA) sequence (mitotypes), mitochondrial function, and temperature adaptation between populations, particularly in metazoans. The mitochondrial climatic adaptation hypothesis (Camus et al. 2017) posits that functional variation between mitotypes plays an important role in shaping adaptation of organisms to their thermal environment. Support for this hypothesis comes from both indirect and, increasingly, direct lines of evidence. Clines of mitotypes along temperature gradients or associations between mitotype and distinct thermal environments have been observed for numerous metazoan species (Cheviron and Brumfield 2009; DuBay and Witt 2014; Quintela et al. 2014; Silva et al. 2014; Baris et al. 2016), including *Drosophila* (Camus et al. 2017), salmon (Consuegra et al. 2015), shrews (Fontanillas et al. 2005), whales (Foote et al. 2011), and humans (Mishmar et al. 2003) among others. Experiments in invertebrates have demonstrated directly that different mitotypes can alter temperature tolerance (Willett 2011; Pichaud et al. 2013), and more recently, direct experimental evidence has emerged for the role of mitotype in thermal adaption in natural environments (Dingley et al. 2014; Camus et al. 2017).

Genetically dissecting mitochondrially-encoded traits in metazoans is difficult, due to their obligately sexual lifestyle and uniparental mitochondrial inheritance. In addition, mitochondrial candidate loci are difficult to identify, unless there are only a small number of nucleotide differences between mitotypes, and differences in non-coding regions are even more difficult to detect (Camus et al. 2017). Furthermore, the results of experiments with mitochondria in animals can be confounded by sex- and tissue-specific differences in mitochondrial function (Fontanillas et al. 2005; Wolff et al. 2016; Camus et al. 2017). For fine scale genetic dissection of traits linked to mtDNA, a more genetically tractable system is desirable.

Recent work has shown that mitotype can also play a role in thermotolerance in the model fungal yeast genus *Saccharomyces* (Paliwal et al. 2014; Špirek et al. 2014; Wolters et al. 2018). The *Saccharomyces* genus consists of eight known species (Liti et al. 2006; Hittinger 2013; Naseeb et al. 2017), which can be broadly divided between cryotolerant and thermotolerant species. Thermotolerant strains (maximum growth temperature ≥36° C.) form a clade that includes the standard model organism *Saccharomyces cerevisiae* (Gonçalves et al. 2011; Salvadó et al. 2011). To date, the genetics of temperature preference, particularly preference for cold temperatures, in *Saccharomyces* yeasts has been difficult to ascertain. Only three candidate loci have been identified as supporting cryotolerance in *Saccharomyces*, two in *S. cerevisiae* and one in a hybrid between the thermotolerant species *S. cerevisiae* and the distantly related cryotolerant species *S. eubayanus* (Yamagishi et al. 2010; Libkind et al. 2011; Gibson et al. 2013; Paget et al. 2014). Recent studies have found that both within and between species variation in mitotype can impact thermotolerance in *Saccharomyces*. Most work in this area has focused on the impact of intraspecies variation in mitotype within *S. cerevisiae* (Paliwal et al. 2014; Wolters et al. 2018) or on interspecies differences between *S. cerevisiae* and its thermotolerant sister species *S. paradoxus* (Leducq et al. 2017), though some work has also investigated more distant genetic relationships within *Saccharomyces* (Špirek et al. 2014). These studies have been largely concerned with mitochondrial function under heat-related stress (~37° C.). However, mitotype could influence temperature tolerance in *Saccharomyces* across a broad range of temperatures, not just at thermal extremes. Indeed, evidence from arctic species suggests that mitochondrial adaption specifically to cold conditions is common (Foote et al. 2011; Garvin et al. 2011; Melo-Ferreira et al. 2014). Furthermore, in a recent study of hybrids of *S. cerevisiae* and the cryotolerant species *Saccharomyces uvarum* when allele specific expression was measured at both 22° C. and 37° C., an unexpected abundance of mitochondrial genes were identified as having allele-specific differences in expression, not only at 37° C., but also at 22° C., where both *S. cerevisiae*, *S. uvarum*, and their hybrid grow robustly (Li and Fay 2017). These results suggest the importance of mitochondrial DNA, even at moderate temperatures.

Among the other cryotolerant species of the *Saccharomyces* genus are *Saccharomyces eubayanus*, *Saccharomyces arboricola*, and *Saccharomyces kudriavzevii*. Together, *S. uvarum* and its sister species *S. eubayanus* form the small "*Saccharomyces bayanus*" clade of *Saccharomyces* (Hittinger 2013), which diverged from *S. cerevisiae* roughly 20 million years ago (Kellis et al. 2003). This amount of divergence represents approximately the equivalent genetic divergence between humans and chickens (Dujon 2006). While the thermotolerant species *S. cerevisiae* is best known for its role in human-associated fermentations, most commercial brewing occurs using cryotolerant *S. cerevisiae*×*S. eubayanus* hybrids in the production of lager-style beers (Libkind et al. 2011). These lager-brewing hybrids are distinguished by the tendency of the yeast to drop to the bottom of fermentations (bottom fermenting), a distinct flavor profile, and robust fermentation at low temperatures (~7-15° C.) (Tenge 2009). In comparison, ale-brewing yeasts tend to float at the top of fermentations and are used to brew at relatively high temperatures (15-24° C.). Most ale strains have been found to consist of pure *S. cerevisiae* genetic material, though some brewing strains classified as ales and isolated from low-temperature regions of Europe, have been determined to be *S. cerevisiae*×*S. kudriavzevii* hybrids (Peris, Belloch, et al. 2012; Peris et al. 2018). Perhaps not surprisingly, the *S. cerevisiae* component of lager yeasts has been found to be most similar to other strains of *S. cerevisiae* used in beer brewing (Dunn and Sherlock 2008; Gonçalves et al. 2016). Among strains of *S. eubayanus* that have been characterized, strains belonging to the Holarctic lineage have been identified as being closely related to the population of *S. eubayanus* that gave rise to lager yeasts (Bing et al. 2014; Peris & Langdon et al. 2016).

With the discovery of the wild-stock of *S. eubayanus* (Libkind et al. 2011), there is substantial interest in developing novel lager-brewing hybrids (Hebly et al. 2015; Krogerus et al. 2015; Krogerus, Magalhies, et al. 2017; Hittinger et al. 2018) and, therefore, in understanding the genetics of brewing-relevant traits, such as temperature tolerance. Intriguingly, the two lineages of lager-brewing yeast and other industrial hybrids inherited their mtDNA from their cryotolerant parent, *S. eubayanus* (Nakao et al. 2009; Baker et al. 2015; Okuno et al. 2016; Peris et al. 2017), but the influence of mtDNA on cryotolerance in lager-brewing yeast is unknown. Here, to determine whether mtDNA plays a role in temperature tolerance in hybrids of *S. cerevisiae* and *S. eubayanus*, we tested relative growth of newly created synthetic hybrids inheriting different parental mitotypes. We also directly tested the influence of mtDNA in an industrial lager strain by replacing the *S. eubayanus* mitotype with mtDNA from *S. cerevisiae*.

The genetic tools available in *Saccharomyces* yeasts permitted us to manipulate the inheritance of mtDNA in identical nuclear backgrounds. We find that, when mtDNA from the thermotolerant parent, *S. cerevisiae*, is inherited, hybrids have superior growth over hybrids with *S. eubayanus* mtDNA when grown at high temperatures. Likewise, hybrids with mtDNA from the cryotolerant parent, *S. eubayanus*, have growth superior to hybrids with *S. cerevisiae* mtDNA at low temperatures. In this way, we show that mitotype directly influences the relative ability of otherwise identical strains to grow at different temperatures.

Results

*S. cerevisiae* and *S. eubayanus* Parent Strains are Thermotolerant and Cryotolerant, Respectively.

In order to establish relative differences in growth between *S. cerevisiae*, *S. eubayanus*, and their hybrids carrying different mitotypes, dilution series of each set of hybrids and parents were spotted onto plates containing either glucose or glycerol as the sole carbon source. As a non-fermentable carbon source, glycerol forces yeasts to utilize their mitochondria via respiration, rather than relying on alcoholic fermentation, their preferred metabolic process of *Saccharomyces* (Crabtree/Warburg Effect) (Dashko et al. 2014). On glucose, $\rho^0$ strains followed the same patterns of growth as their $\rho^+$ parent but grew less at all temperatures (FIGS. 4A-4C), reflecting the well-known "petite" phenotype of respiratorily deficient cells (Merico et al. 2007). $\rho^0$ strains were completely unable to grow on glycerol.

Figure 1B:
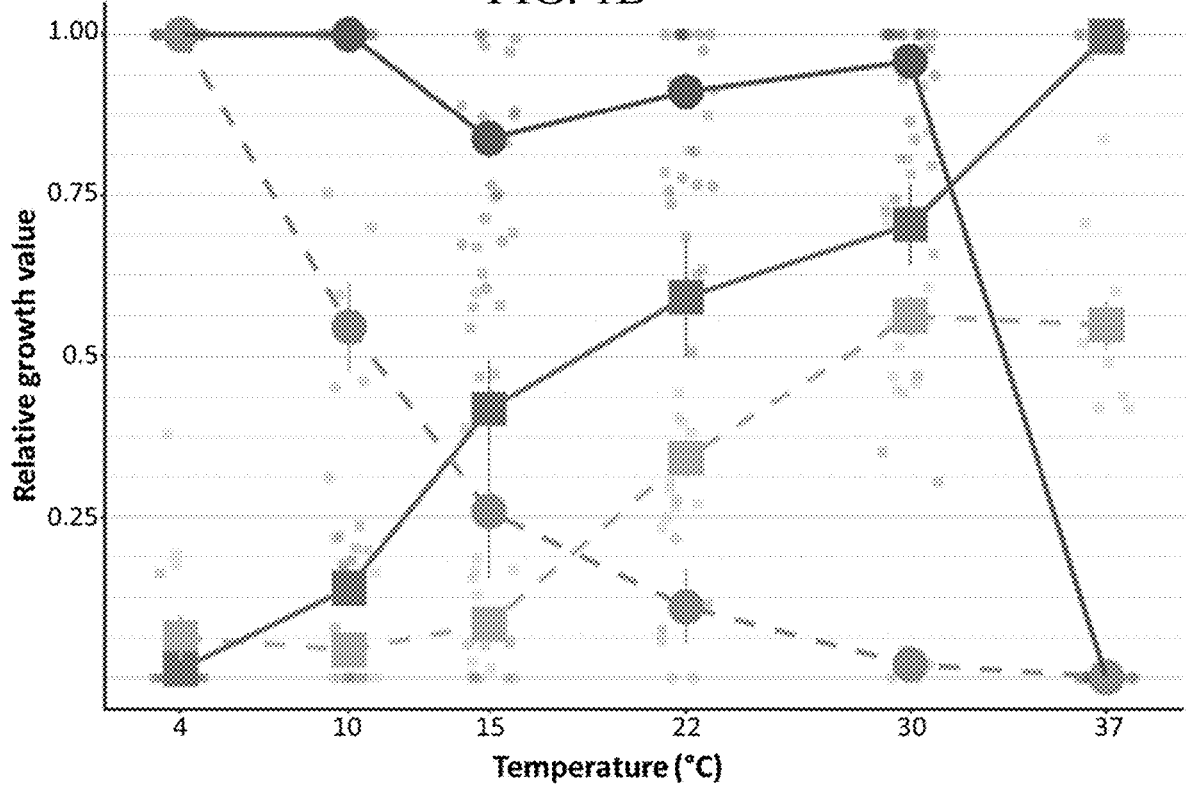

On both glucose and glycerol, the *S. eubayanus* and *S. cerevisiae* parents had opposite temperature responses (FIGS. 1A-1B). *S. eubayanus* strains grew at all temperatures, except 37° C., while *S. cerevisiae* strains began to decline in relative growth at 15° C. and were completely unable to grow at 4° C., a temperature at which the *S. eubayanus* strains still grew well (FIGS. 1A-1B and FIGS. 4A-4C, 5A-5C, 6A-6C, and 7A-7C). These results are consistent with the description of *S. eubayanus* as a cryotolerant species (Libkind et al. 2011), with a similar temperature range to its sister species, *S. uvarum*, and are also consistent with the well-known thermotolerant nature of *S. cerevisiae* strains (Gonçalves et al. 2011; Salvadó et al. 2011). Strain-specific differences were also apparent. Sc and SeNC both grew relatively weakly compared to the other parental strains (FIGS. 1A-1B). For Sc, poor growth was likely driven by the presence of multiple auxotrophies, but the reason for SeNC's poor performance is unknown.

Mitotype Influences Temperature Preference in Hybrids According to the Parental Temperature Profile.

Figure 1C:
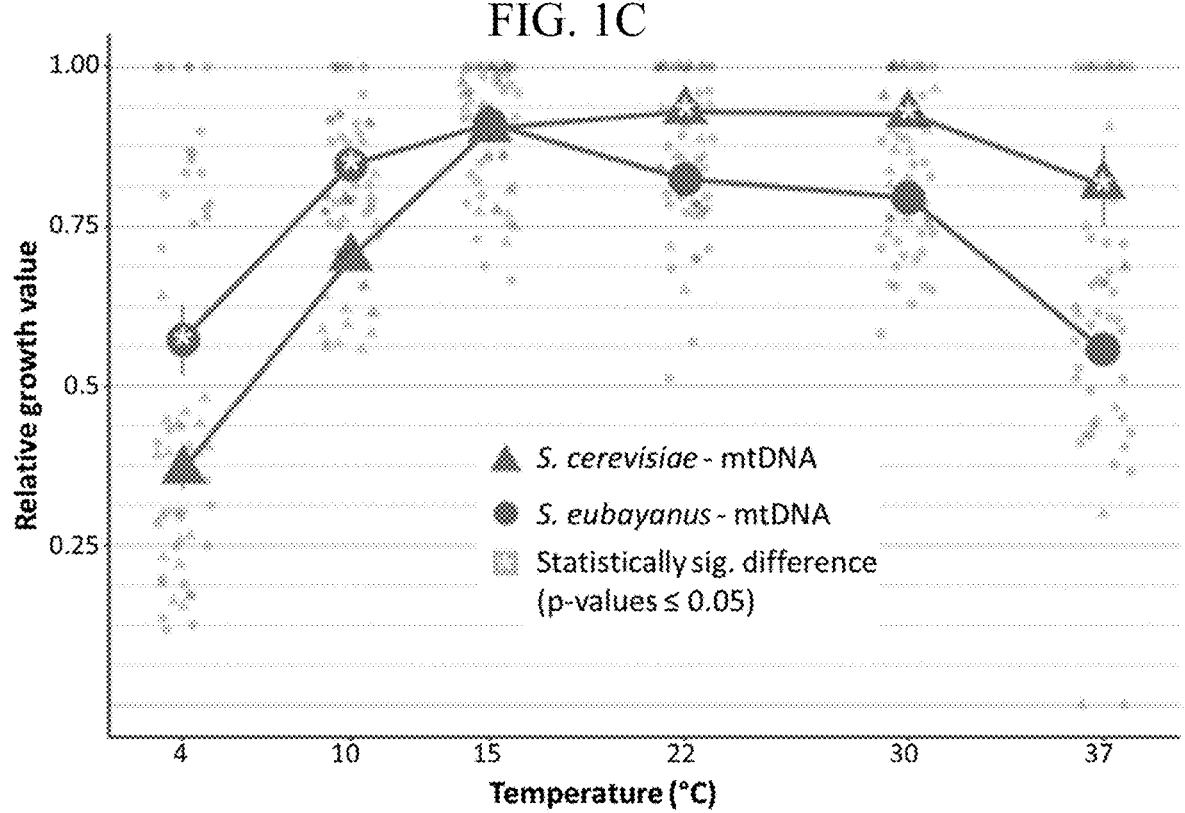

In general, heterosis was clear for hybrids grown on glucose across all temperatures tested (FIGS. 1C and 1D, FIGS. 4A-4C), as has been previously observed for synthetic *S. cerevisiae*×*S. eubayanus* hybrids (Hebly et al. 2015). While relative growth was typically high for hybrids of both mitotypes on glucose, subtle differences were apparent (FIG. 1C). Hybrids carrying *S. cerevisiae* mtDNA had significantly greater growth than hybrids carrying *S. eubayanus* mtDNA between 22 and 37° C., while at 4 and 10° C., it was hybrids with *S. eubayanus* mtDNA that had significantly greater growth. There was no significant difference in growth between hybrids grown at 15° C. on glucose. These same trends were also seen on glycerol but were exaggerated (FIG. 1D), with significant differences between mitotypes at all temperatures. On glycerol, relative growth was greater for *S. eubayanus* mitotype hybrids between 4 and 15° C., while relative growth was greater for hybrids with *S. cerevisiae* mtDNA between 22 and 37° C.

Figure 1D:
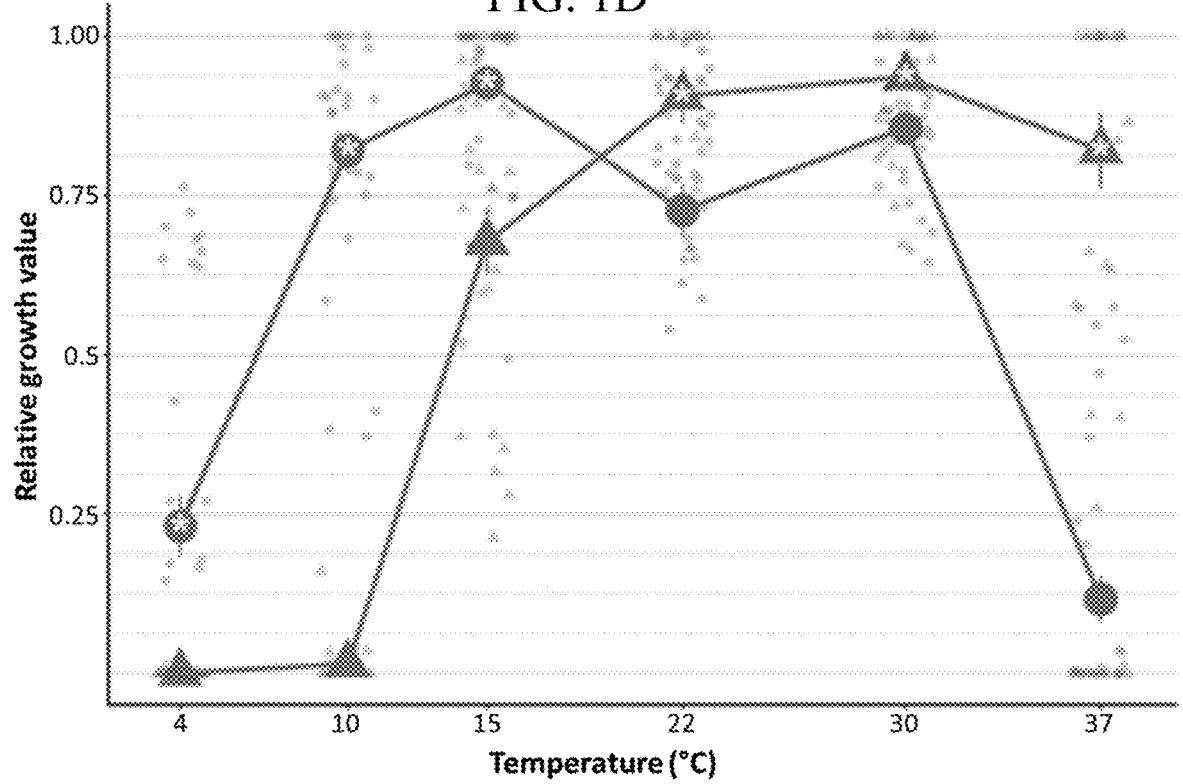
Figure 7A:
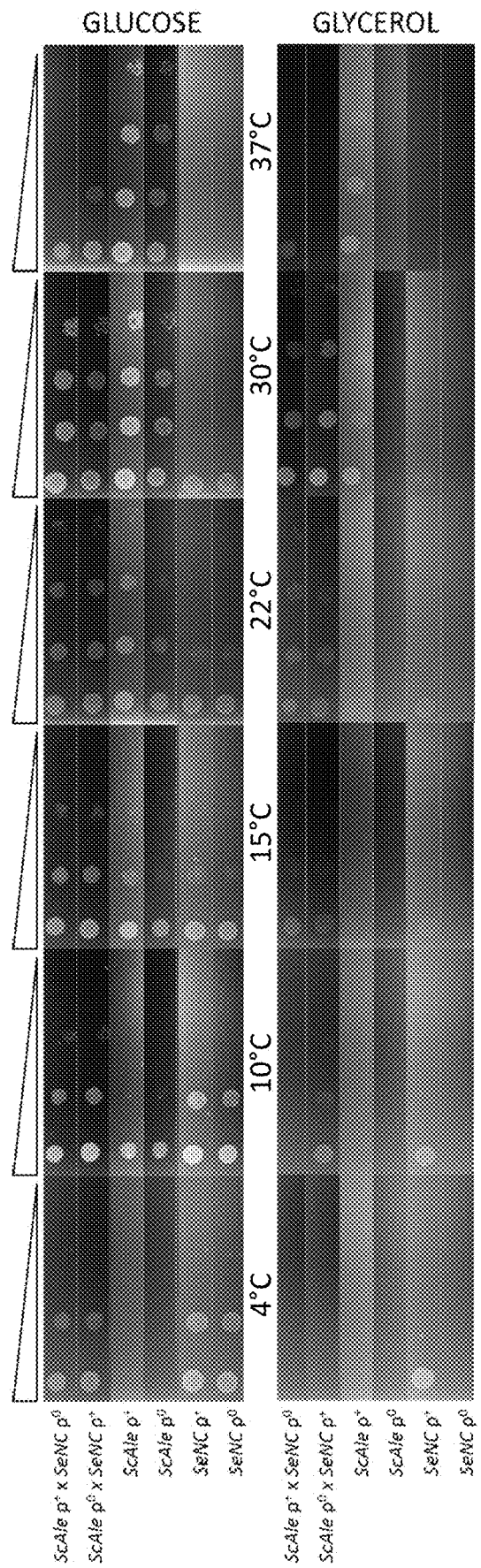
FIGS. 7A-7C. ScAle×SeNC. growth assay. Growth assay for S. cerevisiae-ale×S. eubayanus—North Carolina hybrids and parental strains.
Figure 7B:
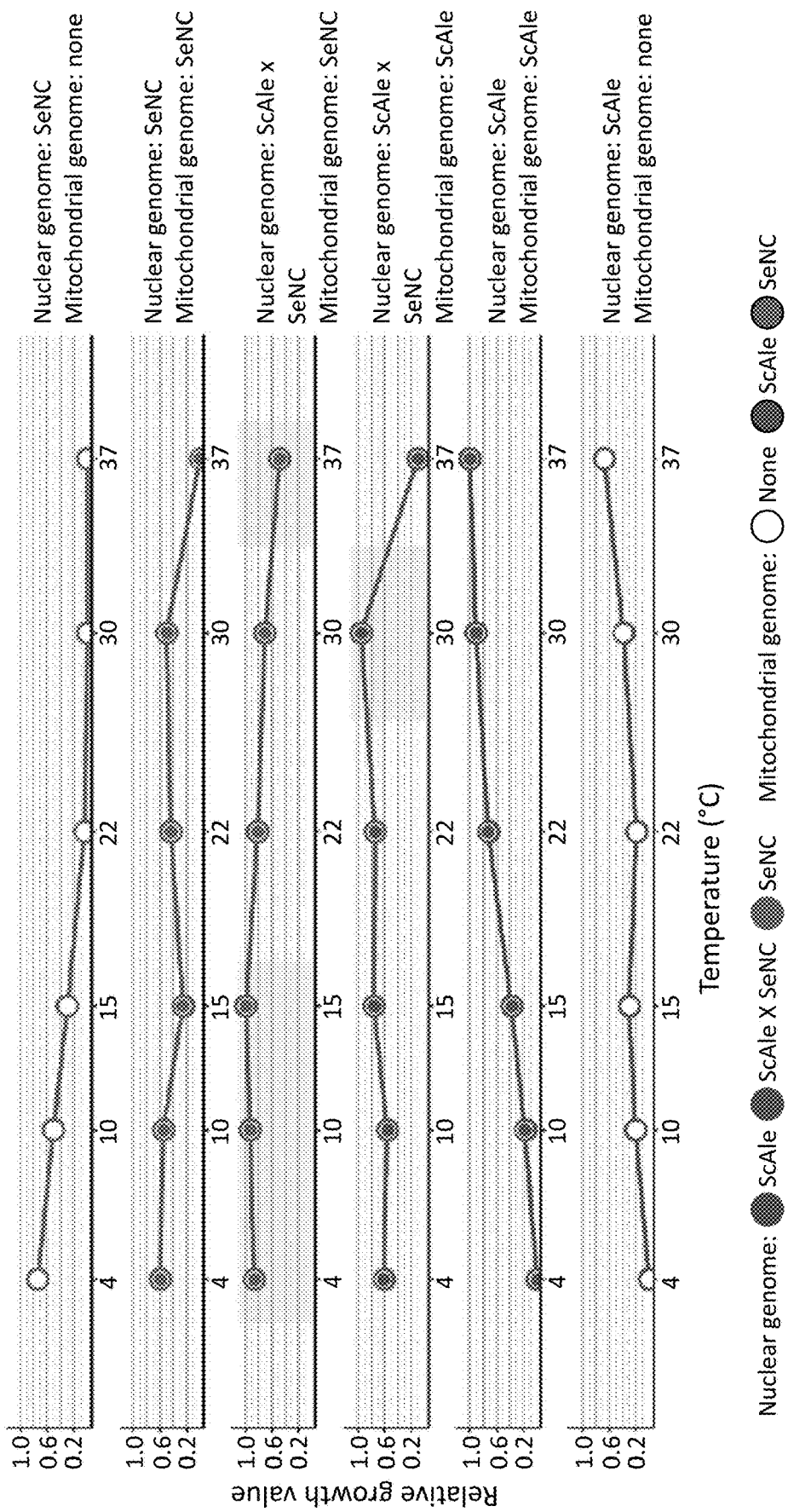
Figure 7C:
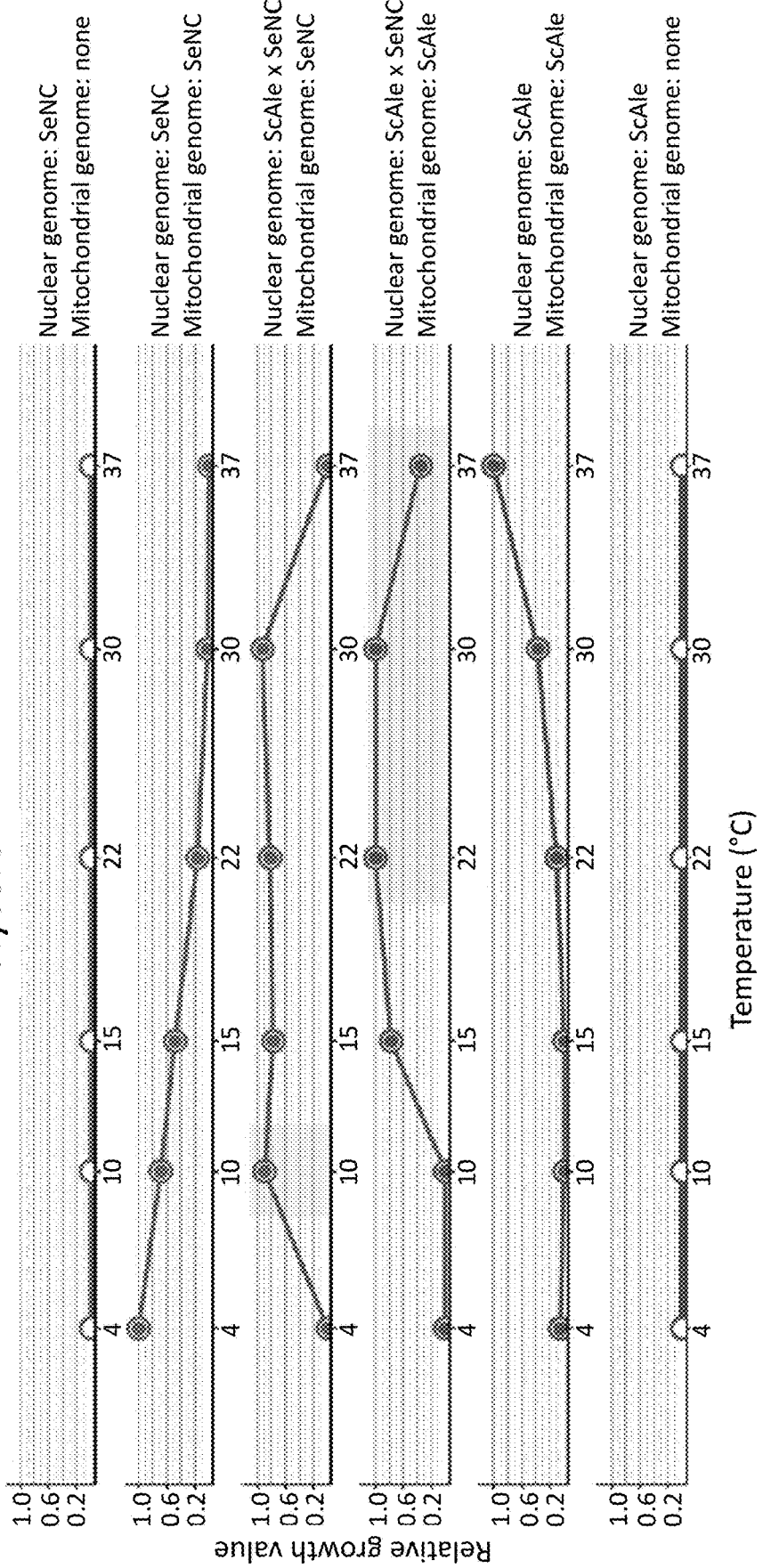

Relative growth patterns for hybrids of different mitotypes were consistent across individual crosses (FIGS. 1A-1B and FIGS. 4A-4C, 5A-5C, 6A-6C, and 7A-7C) and when the data were analyzed statistically in aggregate (FIGS. 1C and 1D). Hybrids carrying mtDNA inherited from the *S. eubayanus* parent, whether from the type strain or the North Carolinian strain, had relatively greater growth at low temperatures compared to hybrids carrying mtDNA inherited from either *S. cerevisiae* parent. Conversely, hybrids with *S. cerevisiae* mtDNA, regardless of whether the mtDNA was from the laboratory strain or the ale strain, had relatively more growth at high temperatures compared to hybrids with *S. eubayanus* mtDNA, with the exception of the ScAle×SeNC $\rho^{ScAle}$ hybrid, which had a substantial growth defect at 37° C. (FIGS. 7A-7C). The growth of the ScAle×SeNC $\rho^{ScAle}$ at other temperatures was otherwise consistent with *S. cerevisiae* mtDNA supporting greater growth at high temperatures (FIG. 7B). On glycerol at 37° C., despite still displaying a clear growth defect, the ScAle× SeNC $\rho^{ScAle}$ hybrid still had greater growth than the ScAle× SeNC $\rho^{SeNC}$ hybrid (FIG. 7C). These results strongly support the contribution of mtDNA to temperature tolerance in S. cerevisiae×S. eubayanus hybrids, despite strain-specific differences.

Figure 2A:
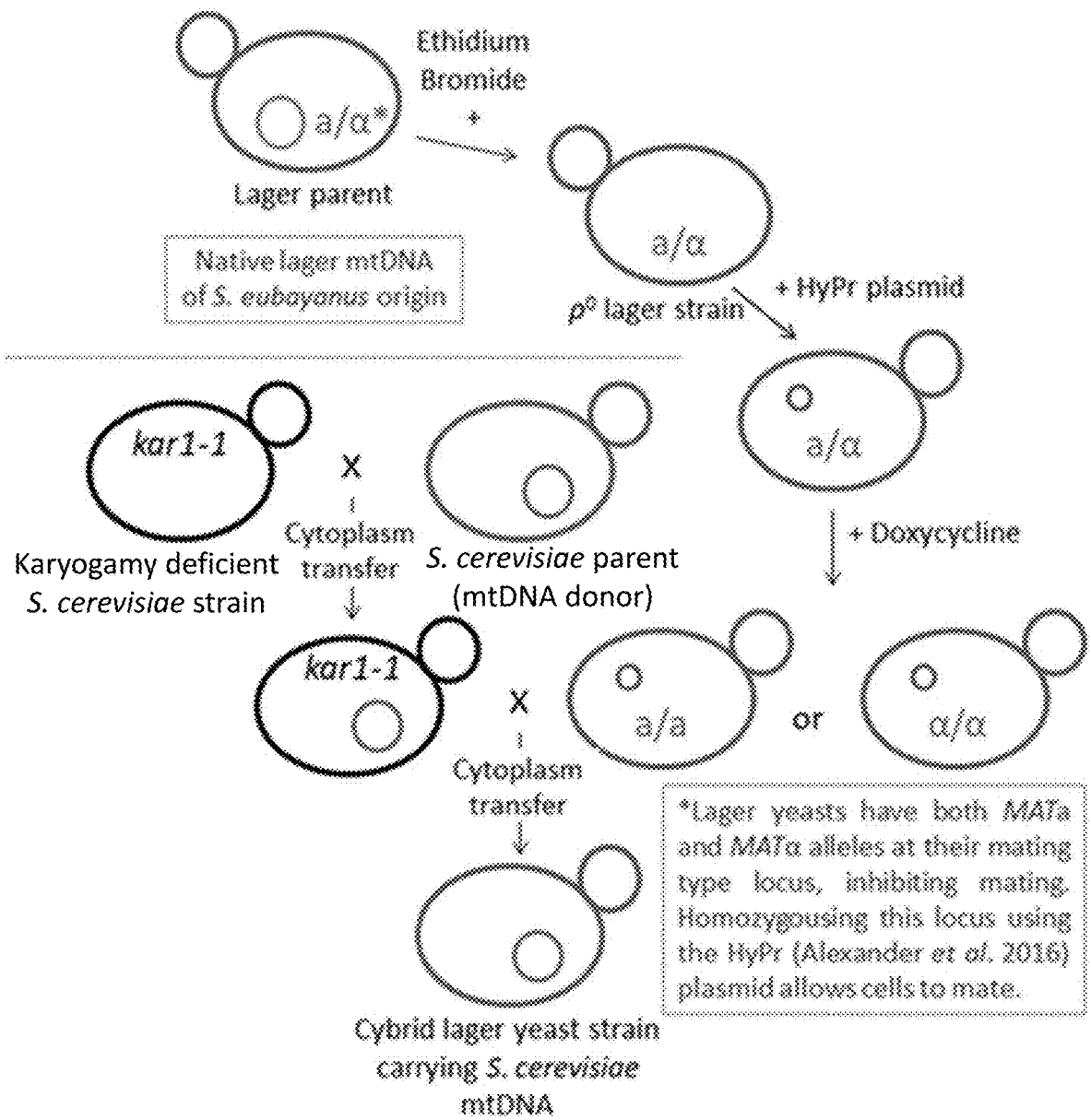
FIGS. 2A-2C. Construction and relative growth of lager cybrids.
Figure 2B:
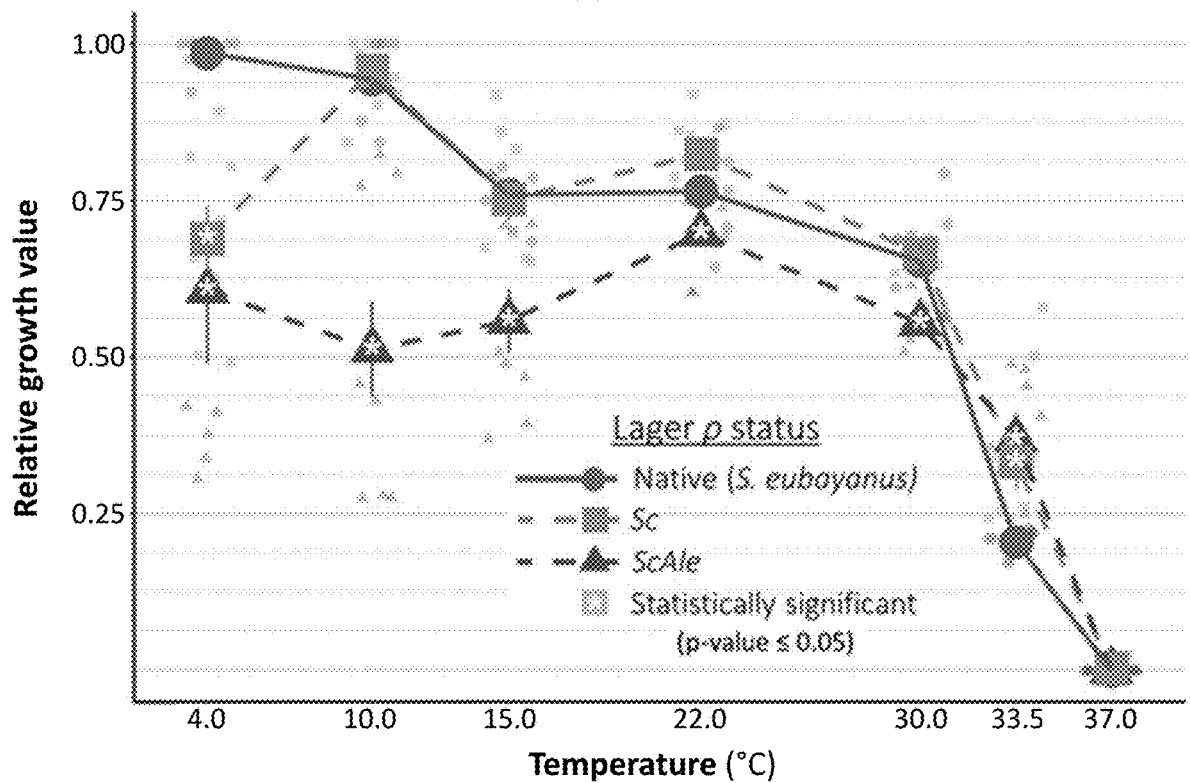
Figure 2C:
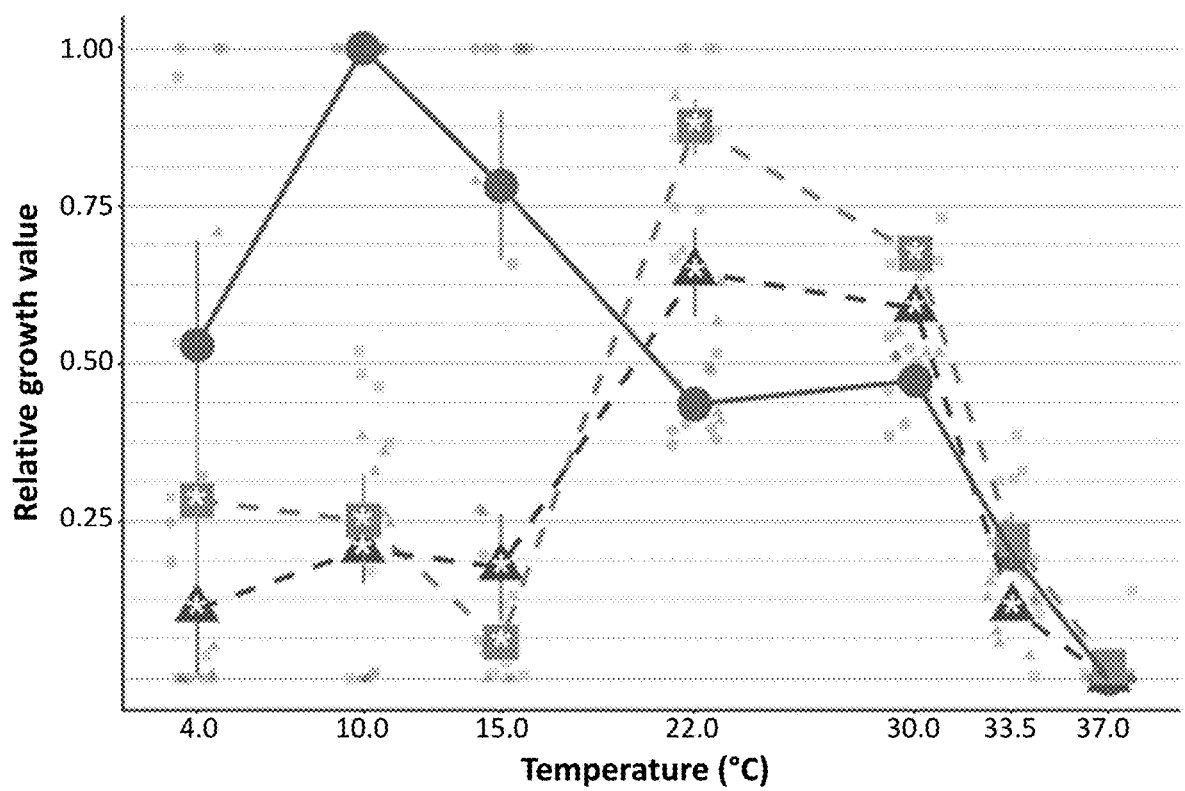
Figure 8A:
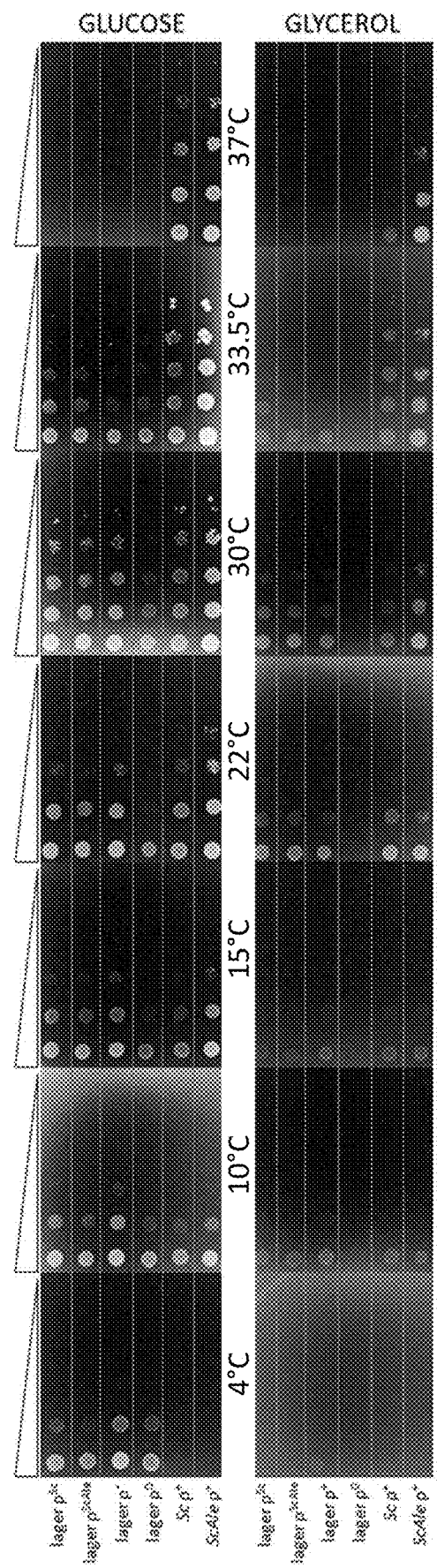
FIGS. 8A-8C. Lager cybrid growth assay. Growth assay for lager cybrids and parental strains.
Figure 8B:
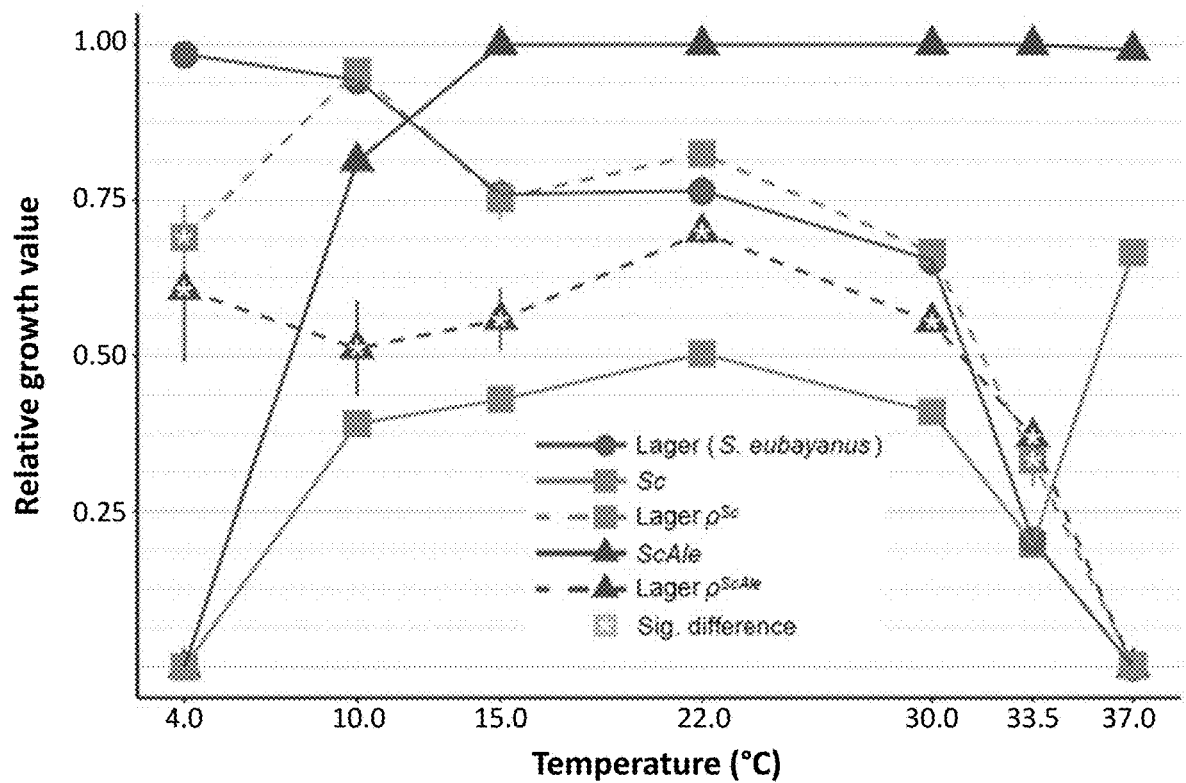
Figure 8C:
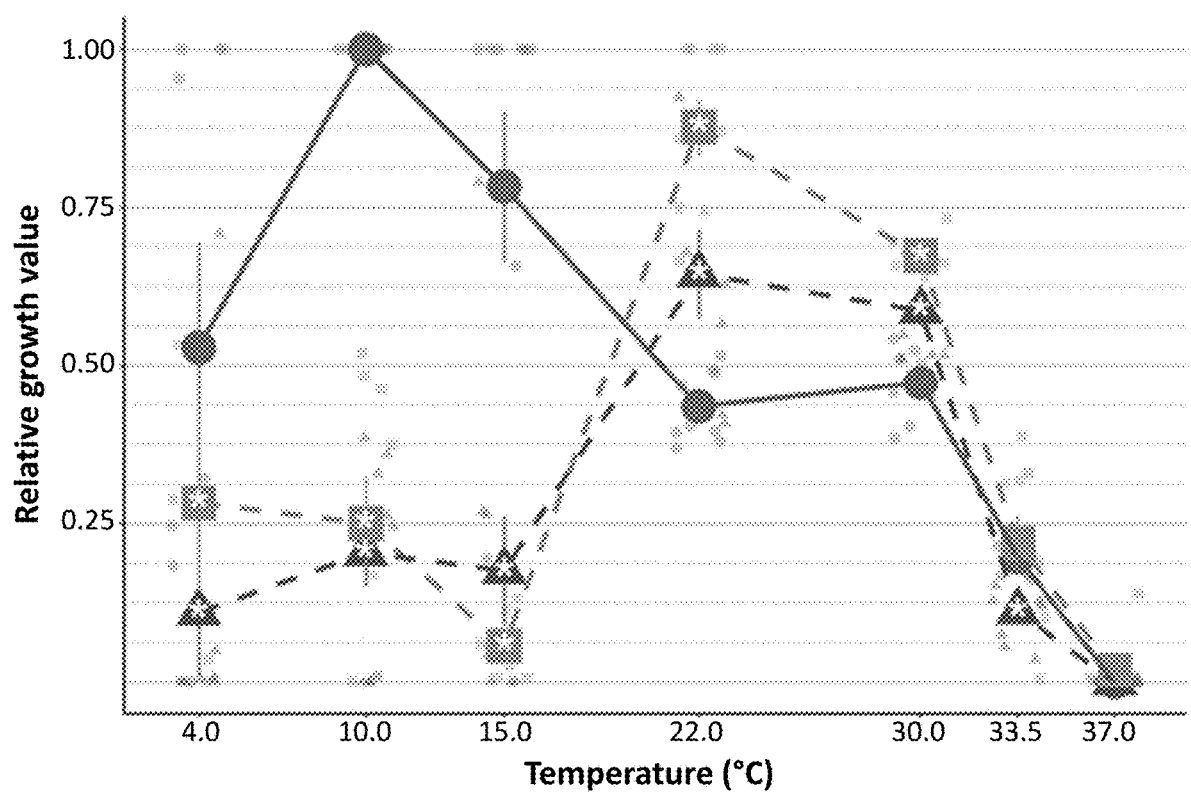

S. cerevisiae Mitochondrial DNA Improves Thermotolerance of an Industrial Lager Strain Unlike the synthetic hybrids assayed above, the S. cerevisiae and S. eubayanus nuclear genomes of industrial lager-brewing yeast hybrids have been evolving in to lagering conditions for numerous generations (Meussdoerffer 2009; Gibson and Liti 2015). As a result, the effect of mtDNA on temperature tolerance may not be the same in these industrial hybrids as it was for newly generated hybrids. To test if mtDNA still play a role in temperature tolerance in lager-brewing yeast, the native lager mtDNA of S. eubayanus origin (Nakao et al. 2009; Peris et al. 2014; Baker et al. 2015; Okuno et al. 2016; Peris et al. 2017) was replaced with S. cerevisiae mtDNA from Sc and ScAle yeasts (FIG. 2A). Consistent with the results for our synthetic hybrids, lager yeasts carrying S. cerevisiae mtDNA had greater growth at higher temperatures and increased sensitivity to colder temperatures, with the effect greatly exaggerated on glycerol (FIGS. 2B and 2C). Differences between $\rho^{Sc}$ and $\rho^{ScAle}$ lager cybrids were also clear, especially on glucose. On glucose, there was no difference in growth between lager yeast carrying its native (S. eubayanus) mtDNA and those carrying Sc mtDNA, except at temperature extremes (FIG. 2B). In contrast, lager $\rho^{ScAle}$ strains grew significantly less than the lager strain with its native mtDNA at most temperatures (FIG. 2B), despite the fact that the ScAle $\rho^+$ strain displayed relatively robust growth across most temperatures in comparison to the industrial lager yeast with its native mtDNA (FIG. 8B).

Discussion

Mitotype Influences Temperature Tolerance in Synthetic Hybrids

Overall, hybrids had an increased range of temperatures they could tolerate compared to their parent strains, regardless of which mtDNA they carried. This heterosis was most evident at temperature extremes. On glucose at 37° C., hybrids grew most like their S. cerevisiae parent, while under 15° C., they grew like their S. eubayanus parent. These results support a strong role for the nuclear genome in temperature tolerance and indicate a certain amount of codominance between alleles supporting thermotolerance and cryotolerance. While this overall robustness to temperature was observed regardless of which mtDNA a hybrid carried, there were clear and consistent differences in relative growth between hybrids of different mitotypes. At higher temperatures, the S. cerevisiae mitotypes permitted increased growth relative to the S. eubayanus mitotypes, while the same was true for S. eubayanus mitotypes at lower temperatures, correlating with the relative cryotolerance and thermotolerance of their respective species of origin. Since the nuclear component is identical between hybrids of the same cross, these differences must be due to differences encoded in their mtDNA. While trends in temperature preference were apparent on both respiratory and fermentable carbon sources, the effect was exaggerated on respiratory media where mitochondrial respiration is required for growth. These results were consistent across multiple strain backgrounds, indicating the generality of mtDNA effects on temperature preferences between these species.

Putative Strain-Specific Cytonuclear Incompatibilities Between S. cerevisiae and S. eubayanus Out of six SeNC $\rho^0$ strains tested, we were only able to generate a small number of hybrids with S. cerevisiae strains that carried S. cerevisiae mtDNA, and then only with a single SeNC $\rho^0$ strain (yHEB1638). Compared to Se $\rho^+$ and $\rho^0$ strains and the SeNC $\rho^+$ parent, where every mating attempt with S. cerevisiae strains produced hybrids, successful mating with yHEB1638 was sporadic, with only one out of ten mating attempts resulting in respiratorily competent hybrids. Difficulty forming hybrids was not the only unusual characteristic of the S. cerevisiae×SeNC hybrids with S. cerevisiae mtDNA. While the Sc×SeNC $\rho^{Sc}$ hybrid had high relative growth at 37° C., like other hybrids carrying S. cerevisiae mitochondria, relative growth for the ScAle× SeNC $\rho^{ScAle}$ hybrid plummeted at 37° C. Interestingly, even with this severe temperature-related growth defect, the ScAle mitotype still supported greater growth at 37° C. on glycerol than the SeNC mitotype. Because we were only able to form S. cerevisiae mtDNA carrying hybrids with one SeNC $\rho^0$ strain, it is unclear if this temperature-dependent growth defect is specific to the yHEB1638 background or general to all ScAle×SeNC $\rho^{ScAle}$ crosses. Even if the defect is specific to yHEB1638 and not SeNC in general, it is interesting that it was only detrimental in the ScAle background, as the Sc×SeNC $\rho^{Sc}$ hybrid did not have the same sensitivity to 37° C., despite sharing the same SeNC $\rho^0$ parent. Other studies have also found mitotype-related defects in temperature both within and between species in Saccharomyces in the study of cybrids (Paliwal et al. 2014; Špirek et al. 2014), though not interspecies hybrids as we have here. The potential for dominant cytonuclear incompatibilities could explain why, in hybrids of Saccharomyces, it has been observed that there is a tendency for there to be greater loss of nuclear genetic material from the parental genome that did not contribute the mtDNA (Marinoni et al. 1999; Peris, Lopes, et al. 2012; Peris et al. 2018). Intriguingly, another study also recently uncovered a strain-specific incompatibility between S. cerevisiae and S. eubayanus (Mertens et al. 2015). Taken together, these results imply that strain-specific incompatibilities exist between S. eubayanus and S. cerevisiae that prevent them from mating and/or forming viable offspring, which might be condition-specific in some cases.

Influence and Origin of Mitotype in Industrial Lager Yeasts

The impact of mtDNA on lager strain temperature tolerance was broadly similar to what was observed for synthetic hybrids, with some differences. In synthetic crosses of S. eubayanus and S. cerevisiae, hybrids generally experienced robust growth across all temperatures, regardless of which mtDNA they carried, though mtDNA was more important at temperature extremes, especially on glycerol (FIGS. 1C-1D). This observation supports a strong role of the nuclear genome in supporting general temperature tolerance. In contrast, the industrial lager-brewing hybrid W34/70 was unable to grow at 37° C. and steadily declined in relative growth as temperature increased. Swapping the native S. eubayanus mtDNA for S. cerevisiae mtDNA, increased tolerance to high temperatures on glycerol and, to a lesser extent, on glucose, but the relative growths of the cybrids still declined precipitously as the temperature increased, and they were unable to grow at 37° C. Based on these results, it is likely that, after many generation of selection for cold fermentation, the nuclear genes necessary to support growth at higher temperatures are no longer functional, present, and/or adequately expressed in the industrial hybrid. As a result, any contribution to thermotolerance from the mtDNA is relatively minor on fermentable carbon and insufficient to rescue growth at temperature extremes on either carbon source.

These results are particularly interesting because W34/70 is part of the Frohberg or Group II (Dunn and Sherlock 2008; Nakao et al. 2009) lineage of industrial lager yeasts. Compared to the Saaz or Group I lineage of industrial lager yeasts, the Frohberg lineage has a relatively larger *S. cerevisiae* contribution to its genome (Dunn and Sherlock 2008). The higher *S. cerevisiae* contribution has been associated with relatively greater thermotolerance among Frohberg lineage strains (Dunn and Sherlock 2008; Gibson et al. 2013; Walther et al. 2014). This correlation suggests that, even in a relatively thermotolerant industrial lager strain, the capacity of the *S. cerevisiae* nuclear genome to provide thermotolerance has been substantially reduced compared to the ancestral hybrid. It is nonetheless noteworthy that, even in a genetic background where the nuclear component of thermotolerance has been greatly diminished, mtDNA still plays a clear role in temperature tolerance.

It is tempting to speculate about what factors might have favored the retention of *S. eubayanus* mtDNA over *S. cerevisiae* mtDNA in present-day industrial lager-brewing hybrids. Given the difference in growth between our synthetic hybrids and the industrial lager hybrid and cybrids, it is likely that substantial changes occurred with regard to temperature tolerance over the course of adaption to lagering conditions. It is also evident that much of this change is attributable to changes within the nuclear genome. Even so, the mtDNA inherited still has a significant impact on temperature tolerance in all strains tested, with the *S. eubayanus* mtDNA favoring growth at lower temperatures. Increased cold tolerance could have given hybrids carrying the *S. eubayanus* mtDNA a selective advantage at the lower temperatures and high population densities at which lagers are brewed.

It is interesting to consider that interspecies incompatibilities, along with the ability to grow at low temperatures, might also have been a factor driving the retention of *S. eubayanus* mtDNA in industrial lagers. Of our synthetic hybrids, the ScAle×SeNC hybrids are the most genetically similar to the strains that gave rise to industrial lager hybrids. Like other hybrids tested, at low temperatures those that carried *S. eubayanus* type mtDNA had a growth advantage over hybrids that carried *S. cerevisiae* type mtDNA. Unlike other hybrids, the ScAle×SeNC hybrids with ScAle mtDNA had a severe growth defect at 37° C., the highest temperature assayed. As discussed above, we cannot be certain if this is a strain-specific defect or one general to all ScAle×SeNC $\rho^{ScAle}$ strains. However, if a high-temperature growth defect is common to hybrids between *S. cerevisiae* ale strains and Holarctic lineage *S. eubayanus* strains that inherit the ScAle mitotype, those hybrids that inherited the *S. eubayanus* mitotype could have had another significant advantage above and beyond superior growth at lower temperatures.

One of the initial stages of beer manufacturing is the production of wort by boiling malted grain to extract the sugar component (Krottenthaler et al. 2009). Today, industrial brewers use modern cooling systems to cool the wort after boiling (Schu 2009), but historically, wort was cooled in open troughs, allowing air to pass freely over the hot liquid (Unger 2004: 167). This process exposed the wort to microbes that could colonize and ferment the wort into beer; a similar process is still used in the manufacture of lambics (Burberg and Zarnkow 2009) and American coolship ales (Bokulich and Bamforth 2013). In this scenario, the hybrids with the *S. eubayanus* mtDNA would, not only have had an advantage at the lower temperatures, but would have had an immediate advantage in being able to colonize the wort while it was still too hot for hybrids with ScAle mtDNA. The ability to colonize the wort early and continue rapid growth as the temperature cooled could have given hybrids with *S. eubayanus* mtDNA an insurmountable advantage, not only over their pure *S. cerevisiae* and *S. eubayanus* parents, but also over other hybrids carrying *S. cerevisiae* mtDNA.

CONCLUSIONS

We have shown that mtDNA can have a significant impact on the thermotolerance of hybrids between *S. cerevisiae* and *S. eubayanus*. The identification of a role for mtDNA in temperature adaptation in *Saccharomyces* yeasts offers a new genetically and experimentally tractable tool outside of metazoan systems with which to investigate the mitochondrial climatic adaptation hypothesis (Camus et al. 2017). A particularly exciting possibility from recent work in *S. cerevisiae* is the potential to map differences in thermotolerance, not only to nuclear loci, but to mitochondrially-encoded sequences as well by taking advantage of natural heteroplasmy and mtDNA recombination (Wolters et al. 2018).

While the finding that mtDNA influenced temperature preference in *S. cerevisiae*×*S. eubayanus* hybrids was general across the different strains tested, clear background-dependent difference were also observed. Given the interest in creating new lager hybrids for industrial use (Hebly et al. 2015; Krogerus et al. 2015; Mertens et al. 2015; Krogerus et al. 2016; Krogerus, Seppänen-Laakso, et al. 2017; Nikulin et al. 2018), it is clear that strain background, not only of the *S. cerevisiae* parent, but also the *S. eubayanus* parent, and the inheritance of mtDNA should all be important considerations in strain construction. In addition to establishing a role for mtDNA in cryotolerance in lager yeast, we found that potential strain-specific incompatibilities suggest that *S. cerevisiae*×*S. eubayanus* hybrids could be a productive system for the study of genetic incompatibilities between species, particularly with regard to within species variation in such incompatibilities.

Methods

Yeast Strains and Strain Construction

Not all strains within a species are equally thermotolerant or cryotolerant, and different strains of *S. cerevisiae* can have 4° C. or more difference between their optimum growth temperatures (Salvadó et al. 2011). Since mitotype has been found to be important, at least at temperature extremes (Paliwal et al. 2014; Špirek et al. 2014; Leducq et al. 2017; Wolters et al. 2018), when determining thermotolerance in different strains of *S. cerevisiae*, we decided to include strains from different populations in our study. In addition to a laboratory strain of *S. cerevisiae* and a monosporic derivative of the type strain of *S. eubayanus*, an ale strain of *S. cerevisiae* and a strain of *S. eubayanus* isolated from North Carolina were also included (Hittinger and Carroll 2007; Libkind et al. 2011; Peris & Langdon et al. 2016). These two additional strains were chosen for their relative similarity to the parents of lager-brewing yeast hybrids.

Specifically, FM1283 (Sc) is descended from BY4724, which is itself a derivative of S288C (Brachmann et al. 1998; Hittinger and Carroll 2007). WLP530B (ScAle), is a commercial ale strain; its' pure *S. cerevisiae* background was confirmed by whole genome sequencing and assembly of reads to a concatenated pan-*Saccharomyces* reference genome, by use of the program sppIDer (https://www.biorxiv.org/content/early/2018/05/30/333815). FM1318 (Se) is a monosporic derivative of the taxonomic type strain of *S. eubayanus*, CBS 12357$^T$ (Libkind et al. 2011). The strain yHRVM108 (SeNC) was isolated from North Carolina and identified as being a close relative of the *S. eubayanus* parent of lager-brewing yeast hybrids (Penis and Langdon et at. 2016). W34/70 (Weihenstephan 34/70 or yHAB47) is an industrial strain belonging to the Frohberg lineage of lager-brewing yeast hybrids (Peris and Langdon et al. 2016). All strains used in this study are listed in (Table 1).

TABLE 1

Strains and plasmids used in this Example

| Strain | Synonym | Species | Background | ρ status | MAT | Markers | Description | Source |
|---|---|---|---|---|---|---|---|---|
| FM1283 | yHWA117 | *S. cerevisiae* | BY4724 (S288C) | native mtDNA | a | ura3-Δ lys2-Δ P$_{TDH3}$-yEBFP-T$_{CYC1}$ | Laboratory strain | Hittinger & Carroll (*Nature*, 2007) |
| yHRVM481 | — | *S. cerevisiae* | FM1283 | null | a | ura3-Δ lys2-Δ P$_{TDH3}$-yEBFP-T$_{CYC1}$ | ρ$^0$ laboratory strain | This study |
| yHRVM483 | — | *S. cerevisiae* | FM1283 | null | a | ura3-Δ lys2-Δ P$_{TDH3}$-yEBFP-T$_{CYC1}$ | ρ$^0$ laboratory strain | This study |
| yHRVM485 | — | *S. cerevisiae* | FM1283 | null | a | ura3-Δ lys2-Δ P$_{TDH3}$-yEBFP-T$_{CYC1}$ | ρ$^0$ laboratory strain | This study |
| WLP530B | yHAB48 | *S. cerevisiae* | — | native mtDNA | a/α | — | Brewing isolate (Belgian Ale) | White Labs |
| yHWA245 | — | *S. cerevisiae* | RM11-1a | native mtDNA | a | ade2-Δ::HERP1 leu2-Δ ura3-Δ hoΔ::KanMX | Laboratory strain used to amplify the KanMX cassette with overhangs to the HO locus for allele replacement in WLP530B | Alexander el al. (*Genetics*, 2014) |
| yHEB1528 | — | *S. cerevisiae* | WLP530B | native mtDNA | a | hoΔ::KanMX | Stable haploid of brewing isolate | This study |
| yHEB1632 | — | *S. cerevisiae*-ale | WLP530B | null | a | hoΔ::KanMX | ρ$^0$ stable haploid of brewing isolate | This study |
| yHEB1621 | — | *S. cerevisiae*-ale | WLP530B | null | a | hoΔ::KanMX | ρ$^0$ stable haploid of brewing isolate | This study |
| yHEB1623 | — | *S. cerevisiae*-ale | WLP530B | null | a | hoΔ::KanMX | ρ$^0$ stable haploid of brewing isolate | This study |
| FM1318 | yHEB10 | *S. eubayanus* | — | native mtDNA | a/α | — | Monosporic derivative of the type strain | Libkind & Hittinger et al. (*PNAS*, 2011) |
| yHEB162 | — | *S. eubayanus* | FM1318 | native mtDNA | α | hoΔ::NatMX | Stable haploid of FM1318 | This study |
| yHEB1611 | — | *S. eubayanus* | yHEB162 | null | α | hoΔ::NatMX | ρ$^0$ stable haploid of FM1318 | This study |
| yHEB1613 | — | *S. eubayanus* | yHEB162 | null | α | hoΔ::NatMX | ρ$^0$ stable haploid of FM1318 | This study |

TABLE 1-continued

Strains and plasmids used in this Example

| Strain | Synonym | Species | Background | ρ status | MAT | Markers | Description | Source |
|---|---|---|---|---|---|---|---|---|
| yHEB1614 | — | S. eubayanus | yHEB162 | null | α | hoΔ::NatMX | ρ⁰ stable haploid of FM1318 | This study |
| yHRVM108 | yHEB449 | S. eubayanus | — | native mtDNA | a/α | — | Holarctic population isolate | Peris & Langdon et al. (*PLOS Genetics*, 2016) |
| yHEB1606 | — | S. eubayanus | yHRVM108 | native mtDNA | α | hoΔ::NatMX | Stable haploid of yHRVM108 | This study |
| yHEB1633 | — | S. eubayanus | yHEB1606 | null | | hoΔ::NatMX | ρ⁰ stable haploid of yHRVM108; potentially *S. cerevisiae* ρ incompatible | This study |
| yHEB1634 | — | S. eubayanus | yHEB1606 | null | | hoΔ::NatMX | ρ⁰ stable haploid of yHRVM108; potentially *S. cerevisiae* ρ incompatible | This study |
| yHEB1635 | — | S. eubayanus | yHEB1606 | null | | hoΔ::NatMX | ρ⁰ stable haploid of yHRVM108; potentially *S. cerevisiae* ρ incompatible | This study |
| yHEB1636 | — | S. eubayanus | yHEB1606 | null | | hoΔ::NatMX | ρ⁰ stable haploid of yHRVM108; potentially *S. cerevisiae* ρ incompatible | This study |
| yHEB1637 | — | S. eubayanus | yHEB1606 | null | | hoΔ::NatMX | ρ⁰ stable haploid of yHRVM108; potentially *S. cerevisiae* ρ incompatible | This study |
| yHEB1638 | — | S. eubayanus | yHEB1606 | null | α | hoΔ::NatMX | ρ⁰ stable haploid of yHRVM108; *S. cerevisiae* ρ compatible | This study |
| MCC123 | yHEB879 | S. cerevisiae | — | null | a | ade2-1, ura3-52, kar1-1 | ρ⁰ karyogamy deficient | Thorsness & Fox (*Genetics*, 1993) |
| MCC109 | yHEB880 | S. cerevisiae | — | null | α | ade2-1, ura3-52, kar1-1 | ρ⁰ karyogamy deficient | Costanzo & Fox (*Mol. Cell Biol.*, 1993) |
| yHEB1752 | — | S. cerevisiae × S. eubayanus | FM1283 × yHEB1611 | S. cerevisiae mtDNA | a/α | ura3-Δ lys2-Δ $P_{TDH3}$-yEBFP-$T_{CYC1}$ hoΔ::NatMX | synthetic hybrid | This study |
| yHEB1749 | — | S. cerevisiae × S. eubayanus | FM1283 × yHEB1613 | S. cerevisiae mtDNA | a/α | ura3-Δ lys2-Δ $P_{TDH3}$-yEBFP-$T_{CYC1}$ hoΔ::NatMX | synthetic hybrid | This study |
| yHEB1746 | — | S. cerevisiae × S. eubayanus | FM1283 × yHEB1614 | S. cerevisiae mtDNA | a/α | ura3-Δ lys2-Δ $P_{TDH3}$-yEBFP-$T_{CYC1}$ hoΔ::NatMX | synthetic hybrid | This study |
| yHEB1127 | — | S. cerevisiae × S. eubayanus | yHRVM481 × yHEB162 | S. eubayanus mtDNA | a/α | ura3-Δ lys2-Δ $P_{TDH3}$- | synthetic hybrid | This study |

TABLE 1-continued

Strains and plasmids used in this Example

| Strain | Synonym | Species | Background | ρ status | MAT | Markers | Description | Source |
|---|---|---|---|---|---|---|---|---|
| yHEB1737 | — | S. cerevisiae × S. eubayanus | yHRVM483 × yHEB162 | S. eubayanus mtDNA | a/α | yEBFP-$T_{CYC1}$ hoΔ::NatMX ura3-Δ lys2-Δ $P_{TDH3}$-yEBFP-$T_{CYC1}$ | synthetic hybrid | This study |
| yHEB1740 | — | S. cerevisiae × S. eubayanus | yHRVM485 × yHEB162 | S. eubayanus mtDNA | a/α | ura3-Δ lys2-Δ $P_{TDH3}$-yEBFP-$T_{CYC1}$ hoΔ::NatMX | synthetic hybrid | This study |
| yHEB1768 | — | S. cerevisiae × S. eubayanus | yHEB1528 × yHEB1611 | S. cerevisiae-ale mtDNA | a/α | hoΔ::KanMX/hoΔ::NatMX | synthetic hybrid | This study |
| yHEB1766 | — | S. cerevisiae × S. eubayanus | yHEB1528 × yHEB1613 | S. cerevisiae-ale mtDNA | a/α | hoΔ::KanMX/hoΔ::NatMX | synthetic hybrid | This study |
| yHEB1764 | — | S. cerevisiae × S. eubayanus | yHEB1528 × yHEB1614 | S. cerevisiae-ale mtDNA | a/α | hoΔ::KanMX/hoΔ::NatMX | synthetic hybrid | This study |
| yHEB1761 | — | S. cerevisiae × S. eubayanus | yHEB1632 × yHEB162 | S. eubayanus mtDNA | a/α | hoΔ::KanMX/hoΔ::NatMX | synthetic hybrid | This study |
| yHEB1758 | — | S. cerevisiae × S. eubayanus | yHEB1621 × yHEB162 | S. eubayanus mtDNA | a/α | hoΔ::KanMX/hoΔ::NatMX | synthetic hybrid | This study |
| yHEB1755 | — | S. cerevisiae × S. eubayanus | yHEB1623 × yHEB162 | S. eubayanus mtDNA | a/α | hoΔ::KanMX/hoΔ::NatMX | synthetic hybrid | This study |
| W34/70 | yHAB47 | S. cerevisiae (2n) × S. eubayanus (2n) | Weihenstephan 34/70 | native mtDNA | a/α | — | industrial lager-brewing strain; Frohberg (Group II) lineage | Peris & Langdon et al. (PLOS Genetics, 2016) |
| yHEB1626 | — | S. cerevisiae (2n) × S. eubayanus (2n) | yHAB47 | null | a/α | — | $ρ^0$ industrial lager-brewing strain | This study |
| yHEB1627 | — | S. cerevisiae (2n) × S. eubayanus (2n) | yHAB47 | null | a/α | — | $ρ^0$ industrial lager-brewing strain | This study |
| yHEB1628 | — | S. cerevisiae (2n) × S. eubayanus (2n) | yHAB47 | null | a/α | — | $ρ^0$ industrial lager-brewing strain | This study |
| pHCT2 | pHEB12 | plasmid | — | — | — | NatMX | HyPr plasmid; for doxycycline-inducible mating type switching in Saccharomyces; GenBank KT725395 | Alexander et al. 2016 (Fungal Genet. Biol) |
| yHEB1793 | — | S. cerevisiae (2n) × S. eubayanus (2n) | yHEB1626 | null | a/α | [pHCT2 (HyPr)] | mating competent $ρ^0$ lager strain | This study |
| yHEB1797 | — | S. cerevisiae (2n) × S. eubayanus (2n) | yHEB1627 | null | a/α | [pHCT2 (HyPr)] | mating competent $ρ^0$ lager strain | This study |
| yHEB1798 | — | S. cerevisiae (2n) × S. eubayanus (2n) | yHEB1628 | null | a/α | [pHCT2 (HyPr)] | mating competent $ρ^0$ lager strain | This study |
| yHEB1800 | — | S. cerevisiae (2n) × S. eubayanus (2n) | yHEB1628 | null | a/α | [pHCT2 (HyPr)] | mating competent $ρ^0$ lager strain | This study |

TABLE 1-continued

Strains and plasmids used in this Example

| Strain | Synonym | Species | Background | ρ status | MAT | Markers | Description | Source |
|---|---|---|---|---|---|---|---|---|
| yHEB1835 | — | S. cerevisiae (2n) × S. eubayanus (2n) | yHEB1793 | S. cerevisiae-ale mtDNA | a/α | [pHCT2 (HyPr)] | lager cybrid | This study |
| yHEB1827 | — | S. cerevisiae (2n) × S. eubayanus (2n) | yHEB1797 | S. cerevisiae-ale mtDNA | a/α | [pHCT2 (HyPr)] | lager cybrid | This study |
| yHEB1828 | — | S. cerevisiae (2n) × S. eubayanus (2n) | yHEB1798 | S. cerevisiae-ale mtDNA | a/α | [pHCT2 (HyPr)] | lager cybrid | This study |
| yHEB1839 | — | S. cerevisiae (2n) × S. eubayanus (2n) | yHEB1793 | S. cerevisiae-mtDNA | a/α | [pHCT2 (HyPr)] | lager cybrid | This study |
| yHEB1841 | — | S. cerevisiae (2n) × S. eubayanus (2n) | yHEB1797 | S. cerevisiae-mtDNA | a/α | [pHCT2 (HyPr)] | lager cybrid | This study |
| yHEB1843 | — | S. cerevisiae (2n) × S. eubayanus (2n) | yHEB1800 | S. cerevisiae-mtDNA | a/α | [pHCT2 (HyPr)] | lager cybrid | This study |

To facilitate strain crossing, stable haploid ScAle, Se, and SeNC strains were generated by replacing one allele of the HO locus with a selectable marker by standard lithium acetate transformation (Gietz and Woods 2002; Alexander et al. 2014), with modifications made for transforming S. eubayanus (see below). Successful replacement of the HO locus was confirmed by PCR with primers specific to the HO locus (Table 2). The resultant strains were sporulated and individual tetrads dissected using a Singer Sporeplay. ScAle was sporulated in liquid sporulation medium (1% potassium acetate, 0.005% zinc acetate) and grown at room temperature (~22° C.) before dissecting after 4-5 days. To sporulate Se and SeNC, 200 µL of saturated culture were plated onto a YPD (1% yeast extract, 2% peptone, 2% glucose) plate and grown at room temperature for 3-5 days before dissecting tetrads. Strains lacking the HO coding sequence were selected for by growth on YPD+antibiotic, and the mating type was determined by mating with tester strains.

TABLE 2

Oligonucleotides used in this Example

| Name | Sequence (SEQ ID NO:) | Description |
|---|---|---|
| oHECP B15 | AATACATACAACTTAC TTTTTCAAAATTAATT TACATACTAGATCTGT TTAGCTTGCCTT (SEQ ID NO: 1) | amplifies MX-driven drug markers with overhangs to the S. eubayanus HO locus for allele replacement by homologous recombination. |
| oHECP B16 | TCTATATAGACAACAA CCACTTCCACTAGCCT TTAAGCGAGCTCGTTT TCGACACTGGAT (SEQ ID NO: 2) | amplifies MX-driven drug markers with overhangs to the S. eubayanus HO locus for allele replacement by homologous recombination. |
| oHWA 565 | CTATGGTTTACGAAAT GATCCACG (SEQ ID NO: 3) | primer specific to 450 bp upstream of S. cerevisiae HO locus; used to amplify region around HO locus with selection marker for allele replacement by homologous recombination, to confirm allele replacement, and to confirm the absence of ρ carrier DNA in lager cybrids. |
| oHWA 566 | CACTGACCCAGTCTTG TCTTC (SEQ ID NO: 4) | primer specific to 540 bp downstream of S. cerevisiae HO locus; used to amplify region around HO locus with selection marker for allele replacement by homologous recombination, to confirm allele replacement, and to confirm the absence of ρ carrier DNA in lager cybrids. |
| oHWA 568 | TTTGCAAATCGAAGAC CCAT (SEQ ID NO: 5) | primer internal to oHWA565 and OHWA566; used for sequencing to confirm the absence of ρ carrier DNA in lager cybrids. |

TABLE 2-continued

Oligonucleotides used in this Example

| Name | Sequence (SEQ ID NO:) | Description |
| --- | --- | --- |
| oHMB3 | GTTTCTGGCCGAGCTACAAG (SEQ ID NO: 6) | primer specific to 260 bp upstream of *S. eubayanus* HO locus; used to confirm allele replacement. |
| oHMB4 | CAAGGCCATGTCTTCTCGTT (SEQ ID NO: 7) | primer specific to 410 bp upstream of *S. eubayanus* HO locus; used to confirm allele replacement. |
| oHECPB148 | TTTGAATATCAATGAAAATGCC (SEQ ID NO: 8) | primer specific to the KAR1 locus of *S. cerevisiae*; used to amplify the KAR1 locus to confirm absence of ρ carrier DNA in lager cybrids. |
| oHECPB149 | TTAAAACCTATAATACACATATATATTGC (SEQ ID NO: 9) | primer specific to the KAR1 locus of *S. cerevisiae*; used to amplify and sequence the KAR1 locus to confirm absence of ρ carrier DNA in lager cybrids. |
| oHDP25 | TGCGCCAAGTGTCTGAAGAACAACTGGGA (SEQ ID NO: 10) | primer general to the GAL4 locus of *Saccharomyces*; used to amplify and sequence the GAL4 locus to confirm absence of ρ carrier DNA in lager cybrids (Peris et al. 2012). |
| oHDP26 | GCGATTTCAATCTGGTTATTATACAACATCAT (SEQ ID NO: 11) | primer general to the GAL4 locus of *Saccharomyces*; used to amplify the GAL4 locus to confirm absence of ρ carrier DNA in lager cybrids (Peris et al. 2012). |
| ITS1 | TCCGTAGGTGAACCTGCGG (SEQ ID NO: 12) | standard primer to amplify out the 5.8S rDNA (ITS) sequence from fungi; used to amplify ITS region to confirm successful creation of synthetic hybrids (McCullough et al. 1998). |
| ITS4 | TCCTCCGCTTATTGATATGC (SEQ ID NO: 13) | standard primer to amplify out the 5.8S rDNA (ITS) sequence from fungi; used to amplify and sequence ITS region to confirm successful creation of synthetic hybrids (McCullough et al. 1998). |

*Saccharomyces* Lithium Acetate Transformation Protocol (Gietz and Woods 2002) Adapted for *S. eubayanus*
Materials:
  1 M lithium acetate
  100 mM lithium acetate
  50% (w/v) PEG-4000
  Boiled single-stranded salmon sperm DNA (ssssDNA) (10 mg/mL)
  100% Ethanol
Procedure:
  1. Grow yeast overnight in 3 mL of YPD or other culturing medium.
  2. The next day, inoculate 50 mL of fresh YPD with enough overnight culture to bring the OD to 0.25 and shake at 250 rpm at room temperature.
    Some strains of *S. eubayanus* can tolerate growth at 30° C. and will grow faster at this temperature, but other strains are sensitive and will grow much more slowly.
  3. After four hours, take an $OD_{600}$ reading. If between 0.75 and 1.0 OD, continue to step 4; otherwise, allow to continue shaking.
    For slow growing strains, it may take several more hours to reach the appropriate OD.
  4. Wash yeast cells in $H_2O$.
  5. Resuspend yeast cells in 950 µL 100 mM lithium acetate.
  6. Aliquot 100 µL of cell suspension into Eppendorf tubes.
  7. Spin at maximum speed in microcentrifuge for 1 min, then remove supernatant.
  8. Add in this order:
    240 µL 50% PEG-4000,
    36 µL 1 M lithium acetate,
    43 µL of DNA solution to be transformed,
    5 µL boiled ssssDNA.
  9. Gently resuspend pellet in transformation mixture.
  10. Heat shock for 55 minutes at 34° C.
    37° C. works almost as well.
  11. Add 36 µL 100% Ethanol.
  12. Heat shock for another 5 minutes.
  13. After heat shock, briefly spin down and remove supernatant.
  14. Immediately resuspend in 600 µL of YPD.
Recovery Method 1
  1) Incubate at room temperature for 3 hours on wheel or shaker.
  2) Plate 200 µL of transformation suspension to each of three selective media plates.
  3) Incubate at room temperature.
    The strain can also be grown at 30° C. if the strain is not heat sensitive.
Recovery Method 2
You MUST use this method for counter-selection (e.g. selecting for the loss of URA3 by 5-FOA resistance) to allow for protein turnover.
  1) Plate immediately to YPD and allow to grow overnight.
  2) The next day, replica-plate to selective media.
    Note: The spatial separation provided by this method guarantees that transformants are independent.
If successful, colonies will generally appear after two or three days.
  Depending on the sensitivity of a strain to a given selection regime, it could take a week or more for colonies to appear, with new colonies appearing up to two weeks after transformation.

Gietz D. R., Woods R. A., 2002 Transformation of yeast by lithium acetate/single-stranded carrier DNA/polyethylene glycol method. Methods Enzymol. 350: 87-96.

Synthetic Hybrids

Figure 3:
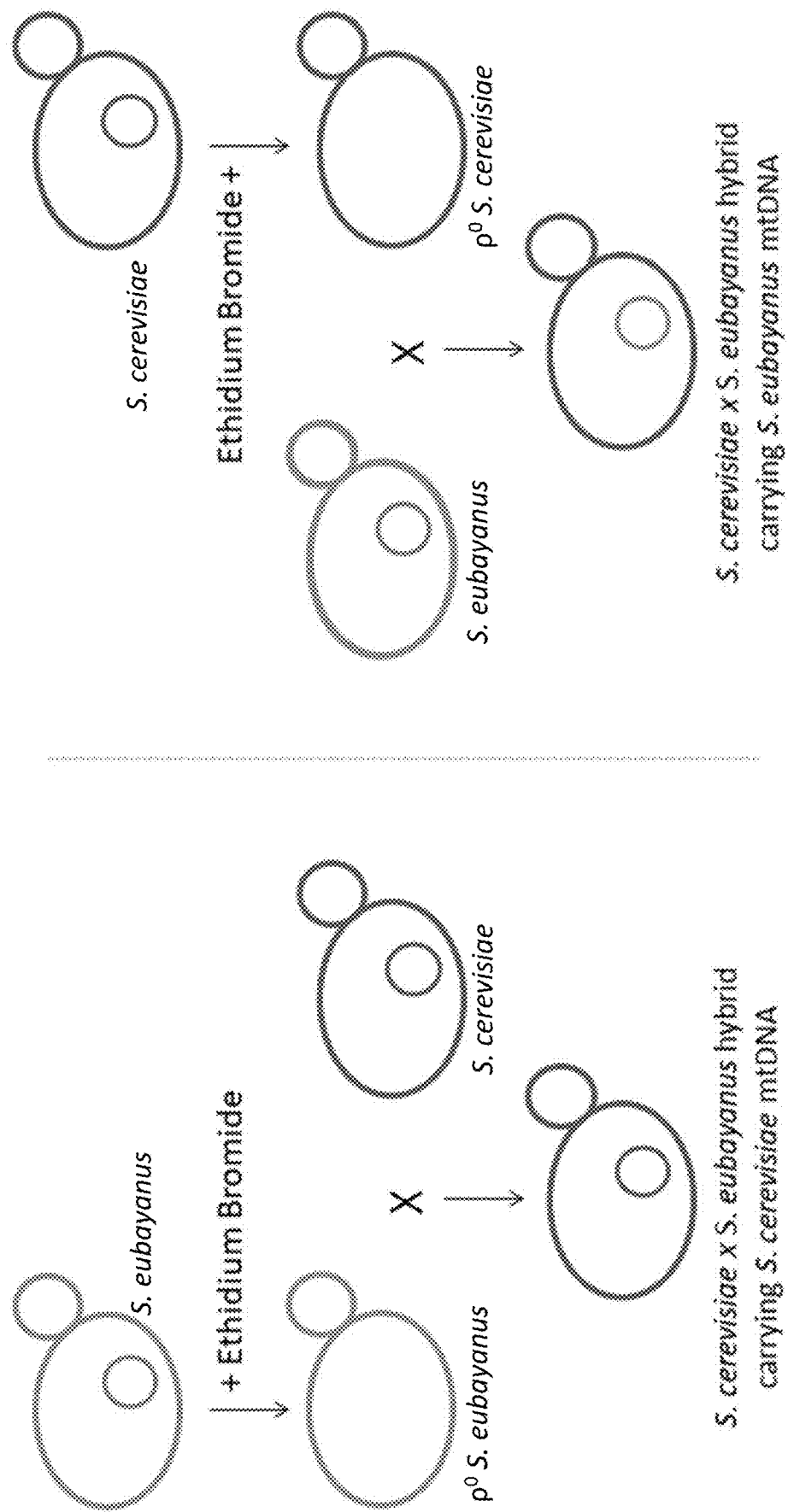
FIG. 3. Hybrid mating scheme. Outline of procedure to control the inheritance of mtDNA in crosses of S. cerevisiae and S. eubayanus. Yeast cells represent the nuclear genome, and inner circles represent mtDNA.
Figure 5A:
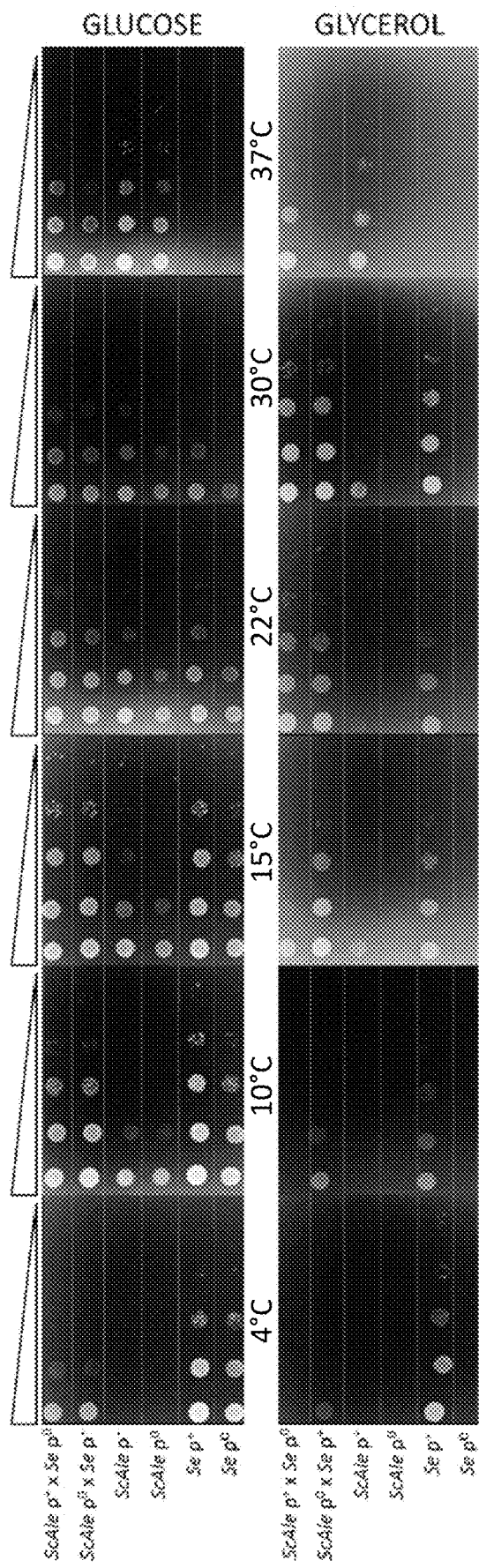
FIGS. 5A-5C. ScAle×Se growth assay. Growth assay for S. cerevisiae-ale×S. eubayanus (type strain) hybrids and parental strains.
Figure 5B:
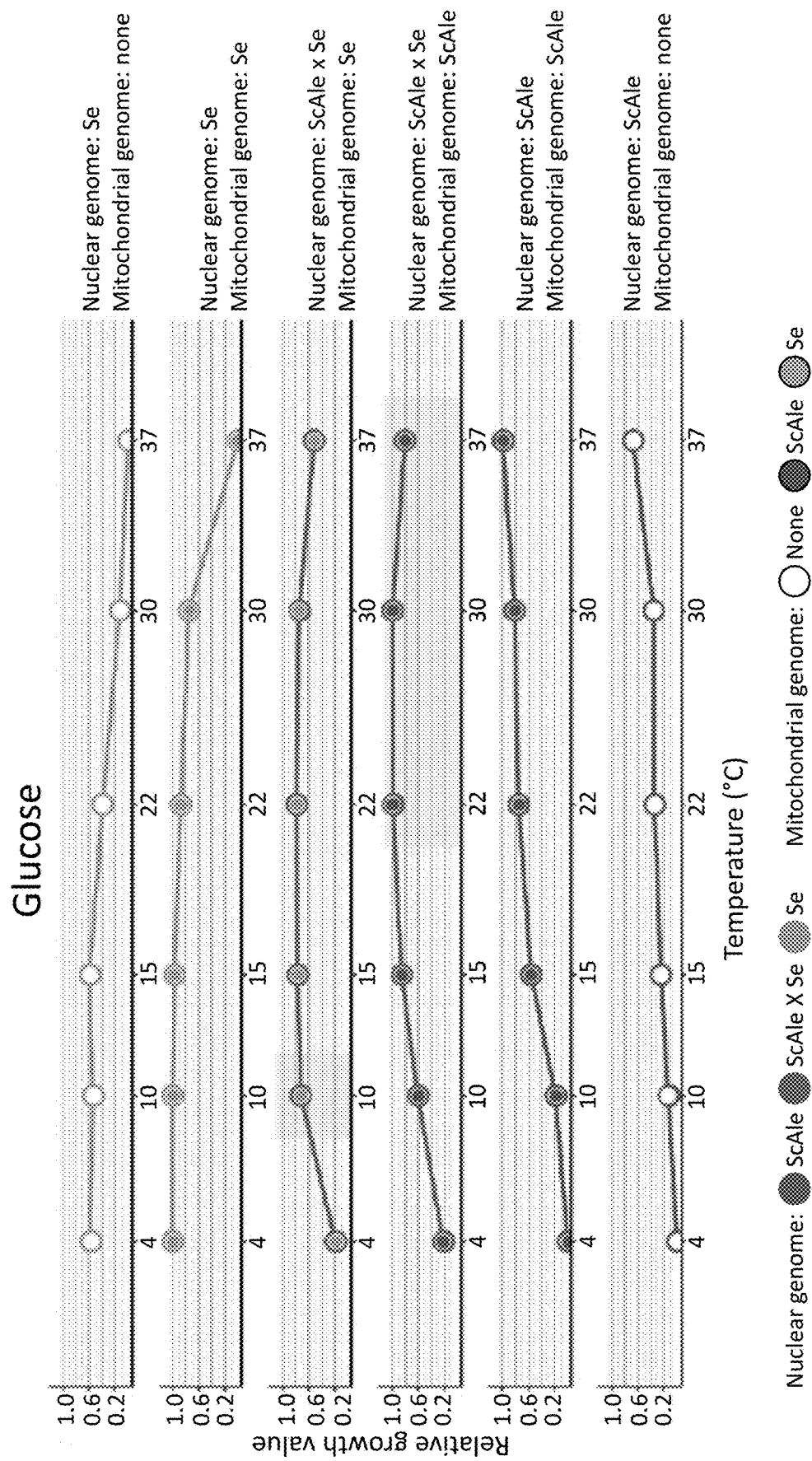
Figure 5C:
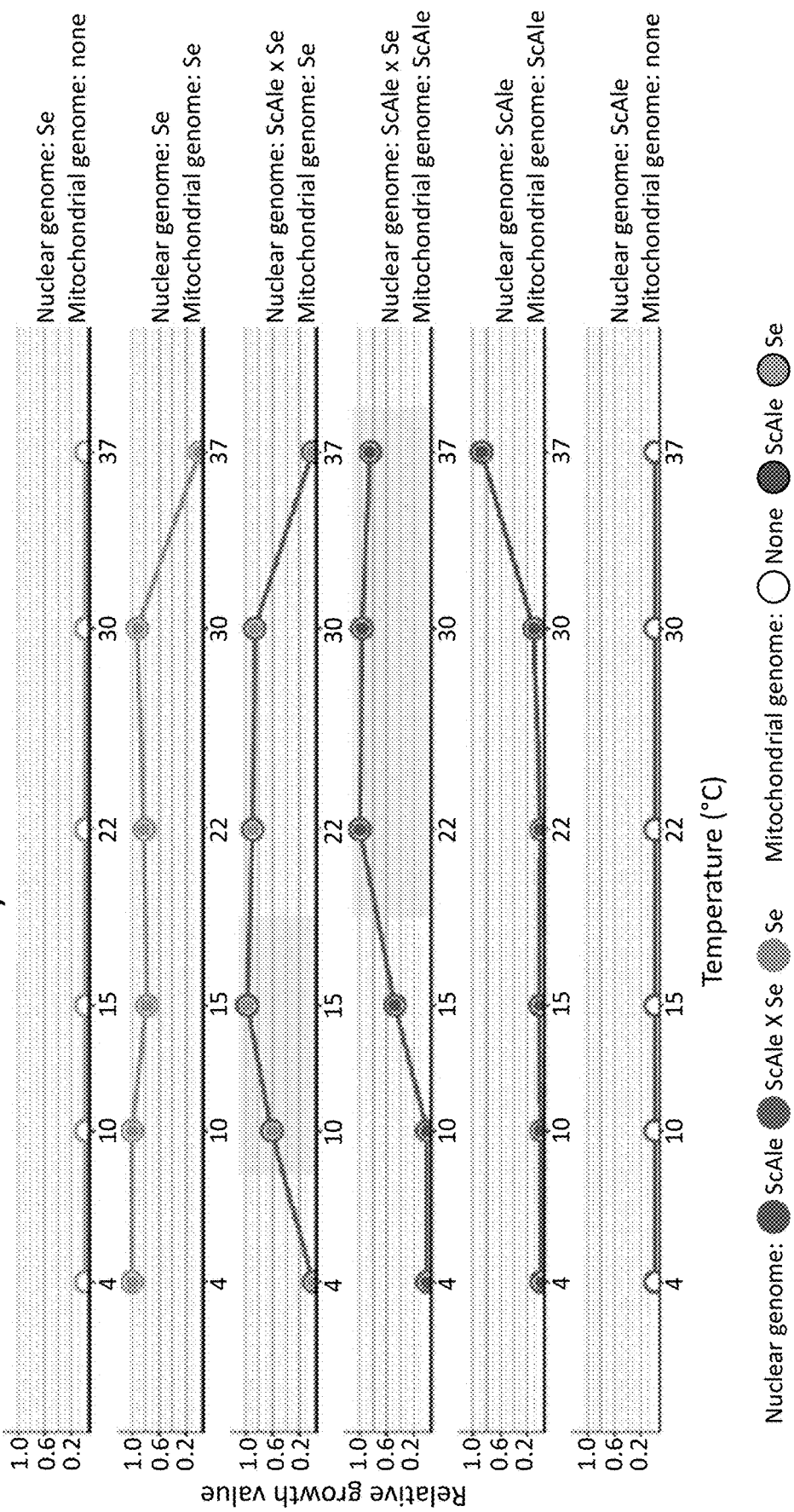
Figure 6A:
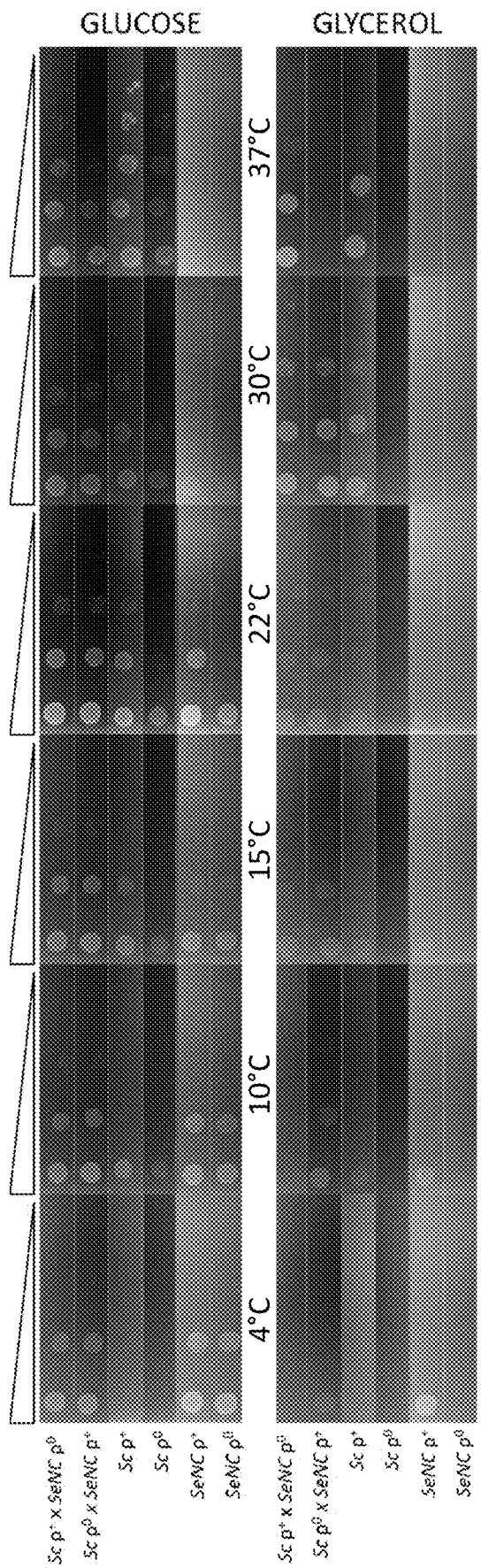
FIGS. 6A-6C. Sc×SeNC growth assay. Growth assay for S. cerevisiae (laboratory strain)×S. eubayanus—North Carolina hybrids and parental strains.
Figure 6B:
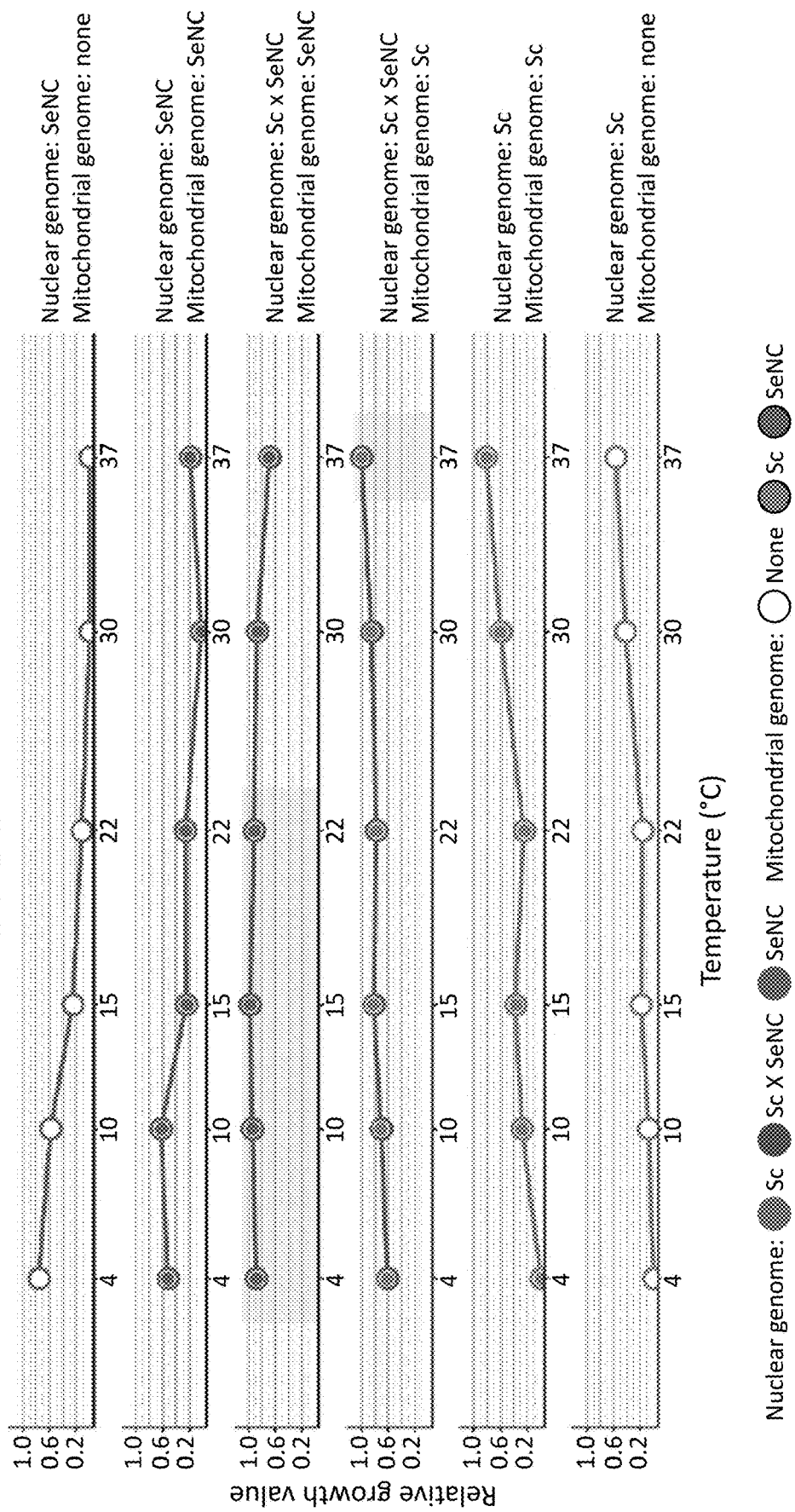
Figure 6C:
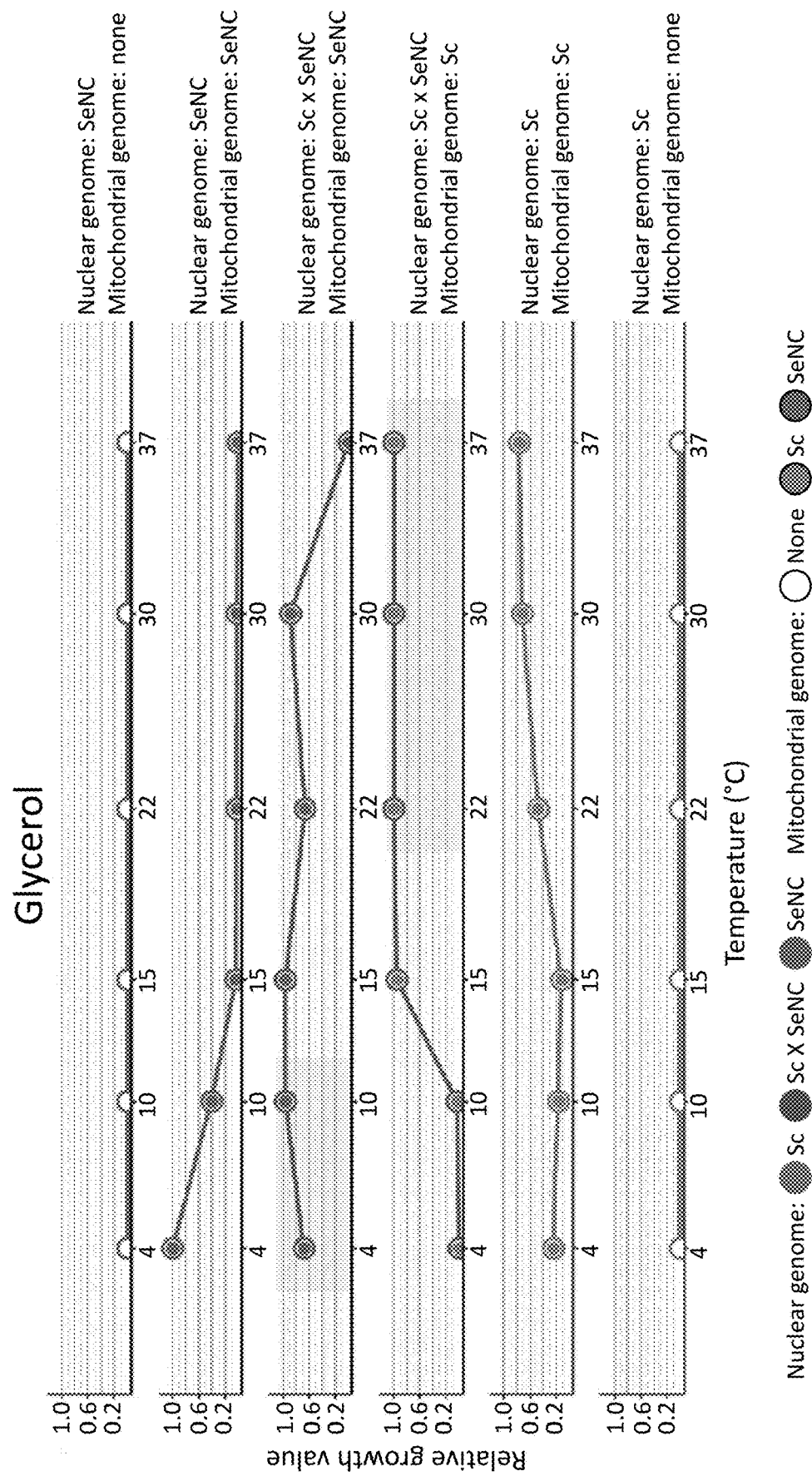

To test the effect of mitotype on temperature tolerance in *S. cerevisiae*×*S. eubayanus* hybrids, we made sets of hybrids containing mtDNA from one parent or the other. When two $\rho^+$ yeast cells mate, the mtDNA of both parents is present in the zygote, but a single mtDNA haplotype is rapidly fixed after only a few cell divisions (Berger and Yaffe 2000). Which mtDNA haplotype is fixed often happens in a non-random manner (Zweifel and Fangman 1991; Marinoni et al. 1999; Hsu and Chou 2017), and recombinant mtDNAs are also possible, even common (Berger and Yaffe 2000; Wolters et al. 2018). To control the inheritance of mtDNA in synthetic hybrids, we generated $\rho^0$ (mtDNA completely absent) strains to mate with $\rho^+$ strains, so that mtDNA from only the $\rho^+$ parent would be present in hybrids (FIG. 3). $\rho^0$ strains were generated by treating $\rho^+$ parent strains with ethidium bromide (Fox et al. 1991). Respiration-deficient strains were screened for by the absence of growth on glycerol, and the complete removal of mtDNA was confirmed by DAPI staining (Eckert-Boulet et al. 2011). Because of the mutagenic nature of ethidium bromide, to control for the effect of any spurious mutations, we generated $\rho^0$ strains of each parent strain in triplicate.

Hybrids were made by mating a $\rho^0$ strain of one species with a $\rho^+$ strain of the opposite mating type of the other species. Mating was performed by mixing the parent strains together on a YPD plate and letting them mate overnight. Allowing mating to occur for one or two more days and/or at 30° C. sometimes improved mating efficiency. Hybrids were selected by growth on glycerol and resistance to the appropriate antibiotics. When appropriate drug selection markers were not present in the parental genomes, zygotes were picked manually and tested for growth on glycerol to confirm retention of functional mitochondria. The hybrid nature of all strains was confirmed by ITS sequencing (Table 2) (McCullough et al. 1998; Sylvester et al. 2015). To ensure the maintenance of functional mitochondria, hybrid strains were grown only on media with glycerol as the sole carbon source, except for during experiments.

In general, the different *S. cerevisiae* and *S. eubayanus* backgrounds and mitotypes readily formed hybrids, although mtDNA could be lost if hybrids were not grown on non-fermentable media. The exception was for crosses attempted between *S. eubayanus*-North Carolina (SeNC) $\rho^0$ strains and *S. cerevisiae* $\rho^+$ strains (both the lab and ale strains). Hybrids between SeNC $\rho^0$ and *S. cerevisae* $\rho^+$ strains were attempted multiple times (>50 attempts total) with six independently generated SeNC $\rho^0$ strains. Out of these attempts, only 4 successful hybrids were formed, one between yHEB1528 (ScAle $\rho^+$) and yHEB1638 (SeNC $\rho^0$) and three between yHWA117 (Sc $\rho^+$) and yHEB1638 (SeNC $\rho^0$). There was no similar difficulty producing the same hybrids with *S. eubayanus* mitochondrial genomes.

It is not clear if the ability to form respiratorily competent hybrids is unique to yHEB1638, as even hybrids with this strain took multiple attempts to achieve. Because the ethidium bromide used to generate $\rho^0$ strains is broadly mutagenic, it is likely that yHEB1638 has a number of mutations differentiating it from the other SeNC $\rho^0$ strains we generated. It is possible that one of these changes allowed yHEB1638 to maintain functional mtDNA in hybrids with *S. cerevisiae* carrying *S. cerevisiae* mtDNA, whereas other SeNC $\rho^0$ strains could not. We include the results of growth assays with the hybrids made using yHEB1638 to determine if they follow the same general trends as other hybrid strains, with the caveat that the results from these experiments cannot be verified by hybrids made from independently generated SeNC $\rho^0$ strains.

Mitochondrial Transfers

To produce strains with a lager yeast nuclear background and *S. cerevisiae* mtDNA (cybrids), karyogamy-deficient (kar1-1) $\rho^0$ strains (Conde and Fink 1976; Costanzo and Fox 1993; Thorsness and Fox 1993) were used to transfer mitochondria from a donor *S. cerevisiae* strain to a $\rho^0$ lager strain (FIG. 2A), which were constructed as described above. Briefly, the lack of karyogamy in crosses with kar1-1 mutants allows the mixing of cytoplasm between mated cells, while preventing fusion between the nuclear genomes, ultimately leading to progeny with mixed cytoplasm, but only one nuclear background. In this way, donor mitochondria from *S. cerevisiae* strains were transferred into the kar1-1 $\rho^0$ strains by mating yeast as above and selecting for functional mtDNA (by growth on glycerol, a non-fermentable carbon source) and the kar1-1 background, while selecting against the donor strain background (FIG. 2A). Since the *S. cerevisiae*-ale strain, WLP530B (ScAle)), and its derivatives are prototrophic, and the kar1-1 strains (MCC109 and MCC123) are auxotrophic for ura3, we were able to select for the kar1-1 background and simultaneously select against the ScAle background by selecting for resistance to 5-fluoro-orotic acid (FOA). To select for kar1-1 background strains carrying mtDNA from the *S. cerevisiae* laboratory strain, FM1283 (Sc), strains were grown on minimal media supplemented with adenine. Because the kar1-1 strains are ade2-1 auxotrophs while Sc is auxotrophic for lys2, this selected for the kar1-1 genetic background and against the Sc genetic background. The medium was also supplemented with uracil for which both the kar1-1 strains and Sc are auxotrophic.

Because lager yeasts contain both MATa and MATα at their mating type locus, mating does not usually occur. To mate polyploid lagers to the kar1-1 $\rho^+$ strains for mitochondria transfer, the MAT locus had to first be homozygosed. The MAT locus of lager $\rho^0$ strains was homozygosed using a HyPr (Hybrid Production) plasmid (pHCT2) to induce mating type switching (Alexander et al. 2016). Cybrids, strains with a single nuclear background and mitochondria from a donor strain, were selected for by selecting against the kar1-1 background. To confirm that only lager genetic material was present in the resulting cybrids, three loci throughout the lager genome were sequenced to confirm that they contained only lager alleles (Table 2). As with hybrids, cybrids were also cultured on glycerol, except for during experiments, to ensure maintenance of mtDNA.

Growth Assays

Each hybrid and cybrid was constructed three times with an independently generated $\rho^0$ parent. Each of these independent hybrids was tested three times at each temperature. In total, combining biological and technical replicates, each hybrid cross was tested a total of nine times at each temperature, with some exceptions. Since there was only one SeNC $\rho^0$ strain with which we were able to successfully form hybrids containing *S. cerevisiae* mtDNA, only one biological replicate for each *S. cerevisiae* strain was formed with SeNC, which each had three technical replicates at each temperature. Consequently, these hybrids (Sc×SeNC $\rho^{ScAle}$ and ScAle×SeNC $\rho^{ScAle}$) only had three replicates total at each temperature. In addition, because of contamination or poor photo quality a small number of replicates (n=5) had to be discarded. These were: two for Sc×SeNC experiments on glycerol, one at 22° C. and one at 37° C.; and three for lager cybrid experiments at 4° C., one replicate growing on glucose and two growing on glycerol.

Yeast strains were grown in liquid synthetic complete (SC) medium (0.17% yeast nitrogen base, 0.5% ammonium sulfate, 0.2% complete drop out mix). Strains containing their native mtDNA and $\rho^0$ strains were grown with 2% glucose, while hybrids and cybrids were grown with 2% glycerol and 2% ethanol to force the maintenance of mtDNA. After reaching saturation, cells were washed in either water or defloculation buffer (20 mM citrate, 5 mM EDTA) and resuspended in either SC (without carbon) or defloculation buffer to an $OD_{600}$ of 1+/−0.05. Due to the extremely flocculent nature of ScAle, cultures had to be washed and resuspended in defloculation buffer. For consistency, all strains used in experiments with ScAle were treated identically with buffer. Yeast strains were plated in a dilution series of $OD_{600}$=1.0, $10^{-1}$, $10^{-2}$, $10^{-3}$, and $10^{-4}$. Dilutions were plated onto SC plates containing either 2% glucose or 2% glycerol as the sole carbon source. Plates were grown at 4, 10, 15, 22, 30, and 37° C. Lager cybrids were also grown at 33.5° C. Plates were grown until at least one strain on a plate showed growth at all five dilutions or after they had been allowed to grow for more than two months, whichever came first.

Analysis of Growth Assays

To determine how well different strains grew relative to each other, the combined intensity (a proxy for growth) of the first and second dilutions ($OD_{600}$=1 and $10^{-1}$) were measured using custom CellProfiler pipelines (Lamprecht, Sabatini, & Carpenter, 2007; www.cellprofiler.org), and the values were combined. To be able to compare growth between plates, which may have differences in absolute intensity, growth on each plate was normalized by dividing by the strain with the highest measured combined intensity on each plate. This procedure created a relative growth score for each strain that was used to compare growth across different replicates. Statistically significant differences in growth were tested for using the Wilcoxon rank-sum test, as implemented in R version 3.4.3 (R Development Core Team 2017), and corrected for multiple tests using the Benjamini-Hochberg procedure (Benjamini and Hochberg 1995), as implemented in R version 3.4.3. P-values ≤0.05 were considered significant.

REFERENCES

Alexander W G, Doering D T, Hittinger C T. 2014. High-efficiency genome editing and allele replacement in prototrophic and wild strains of *Saccharomyces*. Genetics 198:859-866.

Alexander W G, Peris D, Pfannenstiel B T, Opulente D A, Kuang M, Hittinger C T. 2016. Efficient engineering of marker-free synthetic allotetraploids of *Saccharomyces*. Fungal Genet. Biol. 89:10-17.

Baker E, Wang B, Bellora N, Peris D, Hulfachor A B, Koshalek J A, Adams M, Libkind D, Hittinger C T. 2015. The Genome Sequence of *Saccharomyces eubayanus* and the Domestication of Lager-Brewing Yeasts. Mol. Biol. Evol. 32:2818-2831.

Baris T Z, Blier P U, Pichaud N, Crawford D L, Oleksiak M F. 2016. Gene by environmental interactions affecting oxidative phosphorylation and thermal sensitivity. Am. J. Physiol. Integr. Comp. Physiol. 311:R157-R165.

Benjamini Y, Hochberg Y. 1995. Controlling the False Discovery Rate: A Practical and Powerful Approach to Multiple Testing. J. R. Stat. Soc. Ser. B 57:289-300.

Berger K H, Yaffe M P. 2000. Mitochondrial DNA inheritance in *Saccharomyces cerevisiae*. Trends Microbiol. 8:508-513.

Bing J, Han P-J, Liu W-Q, Wang Q-M, Bai F-Y. 2014. Evidence for a Far East Asian origin of lager beer yeast. Curr. Biol. 24:R380-1.

Bokulich N A, Bamforth C W. 2013. The microbiology of malting and brewing. Microbiol. Mol. Biol. Rev. 77:157-172.

Brachmann C B, Davies A, Cost G J, Caputo E, Li J, Hieter P, Boeke J D. 1998. Designer deletion strains derived from *Saccharomyces cerevisiae* S288C: a useful set of strains and plasmids for PCR-mediated gene disruption and other applications. Yeast 14:115-132.

Burberg F, Zarnkow M. 2009. Special Production Methods. In: Esslinger H M, editor. Handbook of brewing processes, technology, markets. Weinheim (Germany). p. 250.

Camus M F, Wolff J N, Sgrb C M, Dowling D K. 2017. Experimental Support That Natural Selection Has Shaped the Latitudinal Distribution of Mitochondrial Haplotypes in Australian *Drosophila melanogaster*. Mol. Biol. Evol. 34:2600-2612.

Cheviron Z A, Brumfield R T. 2009. MIGRATION-SELECTION BALANCE AND LOCAL ADAPTATION OF MITOCHONDRIAL HAPLOTYPES IN RUFOUS-COLLARED SPARROWS (*ZONOTRICHIA CAPENSIS*) ALONG AN ELEVATIONAL GRADIENT. Evolution (N. Y). 63:1593-1605.

Conde J, Fink G R. 1976. A mutant of *Saccharomyces cerevisiae* defective for nuclear fusion. Proc. Natl. Acad. Sci. U.S.A. 73:3651-3655.

Consuegra S, John E, Verspoor E, de Leaniz C G. 2015. Patterns of natural selection acting on the mitochondrial genome of a locally adapted fish species. Genet. Sel. Evol. 47:58.

Costanzo M C, Fox T D. 1993. Suppression of a defect in the 5' untranslated leader of mitochondrial COX3 mRNA by a mutation affecting an mRNA-specific translational activator protein. Mol. Cell. Biol. 13:4806-4813.

Dashko S, Zhou N, Compagno C, Piskur J. 2014. Why, when, and how did yeast evolve alcoholic fermentation? FEMS Yeast Res. 14:826-832.

Dingley S D, Polyak E, Ostrovsky J, Srinivasan S, Lee I, Rosenfeld A B, Tsukikawa M, Xiao R, Selak M A, Coon J J, et al. 2014. Mitochondrial DNA variant in COX1 subunit significantly alters energy metabolism of geographically divergent wild isolates in *Caenorhabditis elegans*. J. Mol. Biol. 426:2199-2216.

DuBay S G, Witt C C. 2014. Differential high-altitude adaptation and restricted gene flow across a mid-elevation hybrid zone in Andean tit-tyrant flycatchers. Mol. Ecol. 23:3551-3565.

Dujon B. 2006. Yeasts illustrate the molecular mechanisms of eukaryotic genome evolution. Trends Genet. 22:375-387.

Dunn B, Sherlock G. 2008. Reconstruction of the genome origins and evolution of the hybrid lager yeast *Saccharomyces pastorianus*. Genome Res. 18:1610-1623.

Eckert-Boulet N, Rothstein R, Lisby M. 2011. Cell biology of homologous recombination in yeast. Methods Mol. Biol. 745:523-536.

Fontanillas P, Dépraz A, Giorgi M S, Perrin N. 2005. Nonshivering thermogenesis capacity associated to mitochondrial DNA haplotypes and gender in the greater white-toothed shrew, *Crocidura russula*. Mol. Ecol. 14:661-670.

Foote A D, Morin P A, Durban J W, Pitman R L, Wade P, Willerslev E, Gilbert M T P, da Fonseca R R. 2011. Positive selection on the killer whale mitogenome. Biol. Lett. 7:116-118.

Fox T D, Folley L S, Mulero J J, McMullin T W, Thorsness P E, Hedin L O, Costanzo M C. 1991. Analysis and manipulation of yeast mitochondrial genes. Methods Enzymol. 194:149-165.

Garvin M R, Bielawski J P, Gharrett A J. 2011. Positive Darwinian Selection in the Piston That Powers Proton Pumps in Complex I of the Mitochondria of Pacific Salmon. PLoS One 6:e24127.

Gibson B, Liti G. 2015. *Saccharomyces pastorianus*: genomic insights inspiring innovation for industry. Yeast 32:17-27.

Gibson B R, Storgirds E, Krogerus K, Vidgren V. 2013. Comparative physiology and fermentation performance of Saaz and Frohberg lager yeast strains and the parental species *Saccharomyces eubayanus*. Yeast 30:255-266.

Gietz D R, Woods R A. 2002. Transformation of yeast by lithium acetate/single-stranded carrier DNA/polyethylene glycol method. Methods Enzymol. 350:87-96.

Gonçalves M, Pontes A, Almeida P, Barbosa R, Serra M, Libkind D, Hutzler M, Gonçalves P, Sampaio J P. 2016. Distinct Domestication Trajectories in Top-Fermenting Beer Yeasts and Wine Yeasts. Curr. Biol. 26:2750-2761.

Gonçalves P, Valbrio E, Correia C, de Almeida JMGCF, Sampaio J P. 2011. Evidence for divergent evolution of growth temperature preference in sympatric *Saccharomyces* species. PLoS One 6:e20739.

Hebly M, Brickwedde A, Bolat I, Driessen M R M, de Hulster E A F, van den Broek M, Pronk J T, Geertman J-M, Daran J-M, Daran-Lapujade P. 2015. *S. cerevisiae*× *S. eubayanus* interspecific hybrid, the best of both worlds and beyond. FEMS Yeast Res. 15:fov005.

Hittinger C T. 2013. *Saccharomyces* diversity and evolution: a budding model genus. Trends Genet. 29:309-317.

Hittinger C T, Carroll S B. 2007. Gene duplication and the adaptive evolution of a classic genetic switch. Nature 449:677-681.

Hittinger C T, Steele J L, Ryder D S. 2018. Diverse yeasts for diverse fermented beverages and foods. Curr. Opin. Biotechnol. 49:199-206.

Hsu Y-Y, Chou J-Y. 2017. Environmental Factors Can Influence Mitochondrial Inheritance in the *Saccharomyces* Yeast Hybrids. PLoS One 12:e0169953.

Kellis M, Patterson N, Endrizzi M, Birren B, Lander E S. 2003. Sequencing and comparison of yeast species to identify genes and regulatory elements. Nature 423:241-254.

Krogerus K, Arvas M, De Chiara M, Magalhies F, Mattinen L, Oja M, Vidgren V, Yue J-X, Liti G, Gibson B. 2016. Ploidy influences the functional attributes of de novo lager yeast hybrids. Appl. Microbiol. Biotechnol. 100:7203-7222.

Krogerus K, Magalhies F, Vidgren V, Gibson B. 2015. New lager yeast strains generated by interspecific hybridization. J. Ind. Microbiol. Biotechnol. 42:769-778.

Krogerus K, Magalhies F, Vidgren V, Gibson B. 2017. Novel brewing yeast hybrids: creation and application. Appl. Microbiol. Biotechnol. 101:65-78.

Krogerus K, Seppanen-Laakso T, Castillo S, Gibson B. 2017. Inheritance of brewing-relevant phenotypes in constructed *Saccharomyces cerevisiae*×*Saccharomyces eubayanus* hybrids. Microb. Cell Fact. 16:66.

Krottenthaler M, Back W, Zarnkow M. 2009. Wort Production. In: Esslinger H M, editor. Handbook of brewing processes, technology, markets. Weinheim (Germany). p. 165-205.

Lamprecht M R, Sabatini D M, Carpenter A E. 2007. CellProfiler: free, versatile software for automated biological image analysis. Biotechniques 42:71-75.

Leducq J-B, Henault M, Charron G, Nielly-Thibault L, Terrat Y, Fiumera H L, Shapiro B J, Landry C R. 2017. Mitochondrial Recombination and Introgression during Speciation by Hybridization. Mol. Biol. Evol. 34:1947-1959.

Li X C, Fay J C. 2017. Cis-Regulatory Divergence in Gene Expression between Two Thermally Divergent Yeast Species. Genome Biol. Evol. 9:1120-1129.

Libkind D, Hittinger C T, Valbrio E, Gonçalves C, Dover J, Johnston M, Gonçalves P, Sampaio J P. 2011. Microbe domestication and the identification of the wild genetic stock of lager-brewing yeast. Proc. Natl. Acad. Sci. U.S.A. 108:14539-14544.

Liti G, Barton D B H, Louis E J. 2006. Sequence diversity, reproductive isolation and species concepts in *Saccharomyces*. Genetics 174:839-850.

Marinoni G, Manuel M, Petersen R F, Hvidtfeldt J, Sulo P, Piskur J. 1999. Horizontal Transfer of Genetic Material among *Saccharomyces* Yeasts Horizontal Transfer of Genetic Material among *Saccharomyces* Yeasts. 181:6488-6496.

McCullough M J, Clemons K V, McCusker J H, Stevens D A. 1998. Intergenic transcribed spacer PCR ribotyping for differentiation of *Saccharomyces* species and interspecific hybrids. J. Clin. Microbiol. 36:1035-1038.

Melo-Ferreira J, Vilela J, Fonseca M M, da Fonseca R R, Boursot P, Alves P C. 2014. The Elusive Nature of Adaptive Mitochondrial DNA Evolution of an Arctic Lineage Prone to Frequent Introgression. Genome Biol. Evol. 6:886-896.

Merico A, Sulo P, Piskur J, Compagno C. 2007. Fermentative lifestyle in yeasts belonging to the *Saccharomyces* complex. FEBS J. 274:976-989.

Mertens S, Steensels J, Saels V, De Rouck G, Aerts G, Verstrepen K J. 2015. A large set of newly created interspecific *Saccharomyces* hybrids increases aromatic diversity in lager beers. Appl. Environ. Microbiol. 81:8202-8214.

Meussdoerffer F G. 2009. A Comprehensive History of Beer Brewing. In: Esslinger H M, editor. Handbook of brewing processes, technology, markets. Weinheim (Germany): Wiley-VCH. p. 28, 31-32.

Mishmar D, Ruiz-Pesini E, Golik P, Macaulay V, Clark A G, Hosseini S, Brandon M, Easley K, Chen E, Brown M D, et al. 2003. Natural selection shaped regional mtDNA variation in humans. Proc. Natl. Acad. Sci. U.S.A. 100:171-176.

Nakao Y, Kanamori T, Itoh T, Kodama Y, Rainieri S, Nakamura N, Shimonaga T, Hattori M, Ashikari T. 2009. Genome sequence of the lager brewing yeast, an interspecies hybrid. DNA Res. 16:115-129.

Naseeb S, James S A, Alsammar H, Michaels C J, Gini B, Nueno-Palop C, Bond C J, McGhie H, Roberts I N, Delneri D. 2017. *Saccharomyces* jurei sp. nov., isolation and genetic identification of a novel yeast species from *Quercus robur*. Int. J. Syst. Evol. Microbiol. 67:2046-2052.

Nguyen H V and Boekhout T. 2017. Characterization of *Saccharomyces uvarum* (Beijerinck, 1898) and related hybrids: assessment of molecular markers that predict the parent and hybrid genomes and a proposal to name yeast hybrids. FEMS Yeast Res. 17(2).

Nikulin J, Krogerus K, Gibson B. 2018. Alternative *Saccharomyces* interspecies hybrid combinations and their potential for low-temperature wort fermentation. Yeast 35:113-127.

Okuno M, Kajitani R, Ryusui R, Morimoto H, Kodama Y, Itoh T. 2016. Next-generation sequencing analysis of lager brewing yeast strains reveals the evolutionary history of interspecies hybridization. DNA Res. 23:67-80.

Paget C M, Schwartz J-M, Delneri D. 2014. Environmental systems biology of cold-tolerant phenotype in *Saccharomyces* species adapted to grow at different temperatures. Mol. Ecol. 23:5241-5257.

Paliwal S, Fiumera A C, Fiumera H L. 2014. Mitochondrial-nuclear epistasis contributes to phenotypic variation and coadaptation in natural isolates of *Saccharomyces cerevisiae*. Genetics 198:1251-1265.

Peris D, Arias A, Orlid S, Belloch C, Pérez-Través L, Querol A, Barrio E. 2017. Mitochondrial introgression suggests extensive ancestral hybridization events among *Saccharomyces* species. Mol. Phylogenet. Evol. 108:49-60.

Peris D, Belloch C, Lopandić K, Álvarez-Perez J M, Querol A, Barrio E. 2012. The molecular characterization of new types of *Saccharomyces cerevisiae*×*S. kudriavzevii* hybrid yeasts unveils a high genetic diversity. Yeast 29:81-91.

Peris D, Langdon Q K, Moriarty R V., Sylvester K, Bontrager M, Charron G, Leducq J-B, Landry C R, Libkind D, Hittinger C T. 2016. Complex Ancestries of Lager-Brewing Hybrids Were Shaped by Standing Variation in the Wild Yeast *Saccharomyces eubayanus*. PLOS Genet. 12:e1006155.

Peris D, Lopes C A, Belloch C, Querol A, Barrio E. 2012. Comparative genomics among *Saccharomyces cerevisiae*×*Saccharomyces* kudriavzevii natural hybrid strains isolated from wine and beer reveals different origins. BMC Genomics 13:407.

Peris D, Pérez-Torrado R, Hittinger C T, Barrio E, Querol A. 2018. On the origins and industrial applications of *Saccharomyces cerevisiae*×*Saccharomyces* kudriavzevii hybrids. Yeast 35:51-69.

Peris D, Sylvester K, Libkind D, Gonçalves P, Sampaio J P, Alexander W G, Hittinger C T. 2014. Population structure and reticulate evolution of *Saccharomyces eubayanus* and its lager-brewing hybrids. Mol. Ecol. 23:2031-2045.

Pichaud N, Ballard J W O, Tanguay R M, Blier P U. 2013. Mitochondrial haplotype divergences affect specific temperature sensitivity of mitochondrial respiration. J. Bioenerg. Biomembr. 45:25-35.

Quintela M, Johansson M P, Kristjinsson B K, Barreiro R, Laurila A. 2014. AFLPs and Mitochondrial Haplotypes Reveal Local Adaptation to Extreme Thermal Environments in a Freshwater Gastropod. PLoS One 9:e101821.

R Development Core Team R. 2017. R: A Language and Environment for Statistical Computing.

Salvadó Z, Arroyo-López FN, Guillamón J M, Salazar G, Querol A, Barrio E. 2011. Temperature adaptation markedly determines evolution within the genus *Saccharomyces*. Appl. Environ. Microbiol. 77:2292-2302.

Schu G. 2009. Energy. In: Esslinger H M, editor. Handbook of brewing processes, technology, markets. Weinheim (Germany). p. 648-650.

Silva G, Lima F P, Martel P, Castilho R. 2014. Thermal adaptation and clinal mitochondrial DNA variation of European anchovy. Proceedings. Biol. Sci. 281: 20141093-20141093.

Špirek M, Poláková S, Jatzová K, Sulo P. 2014. Post-zygotic sterility and cytonuclear compatibility limits in *S. cerevisiae* xenomitochondrial cybrids. Front. Genet. 5:454.

Sylvester K, Wang Q-M, James B, Mendez R, Hulfachor A B, Hittinger C T. 2015. Temperature and host preferences drive the diversification of *Saccharomyces* and other yeasts: a survey and the discovery of eight new yeast species. FEMS Yeast Res. 15:fov002.

Tenge C. 2009. Yeast. In: Esslinger H M, editor. Handbook of brewing processes, technology, markets. Weinheim (Germany): Wiley-VCH. p. 120, 123.

Thorsness P E, Fox T D. 1993. Nuclear mutations in *Saccharomyces cerevisiae* that affect the escape of DNA from mitochondria to the nucleus. Genetics 134:21-28.

Unger R W. 2004. Beer in the Middle Ages and the Renaissance. Philadelphia, Pennsylvania: University of Pennsylvania Press Walther A, Hesselbart A, Wendland J. 2014. Genome Sequence of *Saccharomyces carlsbergensis*, the World's First Pure Culture Lager Yeast. G3 4:783-793.

Willett C S. 2011. The nature of interactions that contribute to postzygotic reproductive isolation in hybrid copepods. Genetica 139:575-588.

Wolff J N, Pichaud N, Camus M F, Côté G, Blier P U, Dowling D K. 2016. Evolutionary implications of mitochondrial genetic variation: mitochondrial genetic effects on OXPHOS respiration and mitochondrial quantity change with age and sex in fruit flies. J. Evol. Biol. 29:736-747.

Wolters J F, Charron G, Gaspary A, Landry C R, Fiumera A C, Fiumera H L. 2018. Mitochondrial Recombination Reveals Mito-Mito Epistasis in Yeast. Genetics 209:307-319.

Yamagishi H, Ohnuki S, Nogami S, Ogata T, Ohya Y. 2010. Role of bottom-fermenting brewer's yeast KEX2 in high temperature resistance and poor proliferation at low temperatures. J. Gen. Appl. Microbiol. 56:297-312.

Zweifel S G, Fangman W L. 1991. A nuclear mutation reversing a biased transmission of yeast mitochondrial DNA. Genetics 128:241-249.

We claim:

1. A method of making a hybrid yeast strain having a selected mitotype comprising:
    treating a first yeast strain with a mitochondria elimination agent to produce a first mitochondria-null yeast strain, and
    mating the first mitochondria-null yeast strain with a second yeast strain comprising mitochondria to produce the yeast strain having the mitotype of the second yeast strain,
    wherein the mitotype of the second yeast strain confers increased cold tolerance relative to the first yeast strain.

2. The method of claim 1, wherein the mitochondria elimination agent is ethidium bromide.

3. The method of claim 1, wherein the first yeast strain and the second yeast strain are different yeast species.

4. The method of claim 1, wherein the first yeast strain and the second yeast strain are haploid.

5. The method of claim 1, wherein the first yeast strain and the second yeast strain are from the genus *Saccharomyces*.

6. The method of claim 5, wherein the first yeast strain and/or the second yeast strain are selected from the group consisting of *Saccharomyces cerevisiae, Saccharomyces paradoxus, Saccharomyces mikatae, Saccharomyces arboricola, Saccharomyces jurei, Saccharomyces kudriavzevii, Saccharomyces uvarum*, and *Saccharomyces eubayanus*.

7. The method of claim 5, wherein the first yeast strain is *Saccharomyces cerevisiae* and the second yeast strain is *Saccharomyces eubayanus*.

* * * * *

UNITED STATES PATENT AND TRADEMARK OFFICE
CERTIFICATE OF CORRECTION

PATENT NO. : 12,012,603 B2
APPLICATION NO. : 16/533928
DATED : June 18, 2024
INVENTOR(S) : Chris Todd Hittinger et al.

It is certified that error appears in the above-identified patent and that said Letters Patent is hereby corrected as shown below:

In the Specification

Column 3, Line 25, "a" should be --α--.

Signed and Sealed this
Thirteenth Day of August, 2024

Katherine Kelly Vidal
*Director of the United States Patent and Trademark Office*

SEQUENCE LISTING

<160> NUMBER OF SEQ ID NOS: 15

<210> SEQ ID NO 1
<211> LENGTH: 60
<212> TYPE: DNA
<213> ORGANISM: Artificial Sequence
<220> FEATURE:
<223> OTHER INFORMATION: oHECPB15 primer

<400> SEQUENCE: 1
aatacataca acttactttt tcaaaattaa tttacatact agatctgttt agcttgcctt    60

<210> SEQ ID NO 2
<211> LENGTH: 60
<212> TYPE: DNA
<213> ORGANISM: Artificial Sequence
<220> FEATURE:
<223> OTHER INFORMATION: oHECPB16 primer

<400> SEQUENCE: 2
tctatataga caacaaccac ttccactagc ctttaagcga gctcgttttc gacactggat    60

<210> SEQ ID NO 3
<211> LENGTH: 24
<212> TYPE: DNA
<213> ORGANISM: Artificial Sequence
<220> FEATURE:
<223> OTHER INFORMATION: oHWA565 primer

<400> SEQUENCE: 3
ctatggttta cgaaatgatc cacg    24

<210> SEQ ID NO 4
<211> LENGTH: 21
<212> TYPE: DNA
<213> ORGANISM: Artificial Sequence
<220> FEATURE:
<223> OTHER INFORMATION: oHWA566 primer

<400> SEQUENCE: 4
cactgaccca gtcttgtctt c    21

<210> SEQ ID NO 5
<211> LENGTH: 20
<212> TYPE: DNA
<213> ORGANISM: Artificial Sequence
<220> FEATURE:
<223> OTHER INFORMATION: oHWA568 primer

<400> SEQUENCE: 5
tttgcaaatc gaagacccat    20

<210> SEQ ID NO 6
<211> LENGTH: 20
<212> TYPE: DNA
<213> ORGANISM: Artificial Sequence
<220> FEATURE:
<223> OTHER INFORMATION: oHMB3 primer

<400> SEQUENCE: 6
gtttctggcc gagctacaag    20

<210> SEQ ID NO 7
<211> LENGTH: 20
<212> TYPE: DNA
<213> ORGANISM: Artificial Sequence
<220> FEATURE:
<223> OTHER INFORMATION: oHMB4 primer

<400> SEQUENCE: 7
caaggccatg tcttctcgtt    20

<210> SEQ ID NO 8
<211> LENGTH: 22
<212> TYPE: DNA
<213> ORGANISM: Artificial Sequence
<220> FEATURE:
<223> OTHER INFORMATION: oHECPB148 primer

<400> SEQUENCE: 8
tttgaatatc aatgaaaatg cc                                        22

<210> SEQ ID NO 9
<211> LENGTH: 29
<212> TYPE: DNA
<213> ORGANISM: Artificial Sequence
<220> FEATURE:
<223> OTHER INFORMATION: oHECPB149 primer

<400> SEQUENCE: 9
ttaaaaccta taatacacat atatattgc                                 29

<210> SEQ ID NO 10
<211> LENGTH: 29
<212> TYPE: DNA
<213> ORGANISM: Artificial Sequence
<220> FEATURE:
<223> OTHER INFORMATION: oHDP25 primer

<400> SEQUENCE: 10
tgcgccaagt gtctgaagaa caactggga                                 29

<210> SEQ ID NO 11
<211> LENGTH: 32
<212> TYPE: DNA
<213> ORGANISM: Artificial Sequence
<220> FEATURE:
<223> OTHER INFORMATION: oHDP26 primer

<400> SEQUENCE: 11
gcgatttcaa tctggttatt atacaacatc at                             32

<210> SEQ ID NO 12
<211> LENGTH: 19
<212> TYPE: DNA
<213> ORGANISM: Artificial Sequence
<220> FEATURE:
<223> OTHER INFORMATION: ITS1 primer

<400> SEQUENCE: 12
tccgtaggtg aacctgcgg                                            19

<210> SEQ ID NO 13
<211> LENGTH: 20
<212> TYPE: DNA
<213> ORGANISM: Artificial Sequence
<220> FEATURE:
<223> OTHER INFORMATION: ITS4 primer

<400> SEQUENCE: 13
tcctccgctt attgatatgc                                           20

<210> SEQ ID NO 14
<211> LENGTH: 586
<212> TYPE: PRT
<213> ORGANISM: Saccharomyces cerevisiae
<220> FEATURE:
<221> NAME/KEY: MISC_FEATURE
<222> LOCATION: (1)..(586)
<223> OTHER INFORMATION: HO protein

<400> SEQUENCE: 14

```
Met Leu Ser Glu Asn Thr Thr Ile Leu Met Ala Asn Gly Glu Ile Lys
 1               5                  10                  15

Asp Ile Ala Asn Val Thr Ala Asn Ser Tyr Val Met Cys Ala Asp Gly
             20                  25                  30

Ser Ala Ala Arg Val Ile Asn Val Thr Gln Gly Tyr Gln Lys Ile Tyr
             35                  40                  45

Asn Ile Gln Gln Lys Thr Lys His Arg Ala Phe Glu Gly Glu Pro Gly
         50                  55                  60

Arg Leu Asp Pro Arg Arg Thr Val Tyr Gln Arg Leu Ala Leu Gln
 65                  70                  75                  80

Cys Thr Ala Gly His Lys Leu Ser Val Arg Val Pro Thr Lys Pro Leu
                 85                  90                  95

Leu Glu Lys Ser Gly Arg Asn Ala Thr Lys Tyr Lys Val Arg Trp Arg
             100                 105                 110

Asn Leu Gln Gln Cys Gln Thr Leu Asp Gly Arg Ile Ile Ile Ile Pro
             115                 120                 125

Lys Asn His His Lys Thr Phe Pro Met Thr Val Glu Gly Glu Phe Ala
         130                 135                 140

Ala Lys Arg Phe Ile Glu Glu Met Glu Arg Ser Lys Gly Glu Tyr Phe
145                 150                 155                 160

Asn Phe Asp Ile Glu Val Arg Asp Leu Asp Tyr Leu Asp Ala Gln Leu
                 165                 170                 175

Arg Ile Ser Ser Cys Ile Arg Phe Gly Pro Val Leu Ala Gly Asn Gly
             180                 185                 190

Val Leu Ser Lys Phe Leu Thr Gly Arg Ser Asp Leu Val Thr Pro Ala
             195                 200                 205

Val Lys Ser Met Ala Trp Met Leu Gly Leu Trp Leu Gly Asp Ser Thr
             210                 215                 220

Thr Lys Glu Pro Glu Ile Ser Val Asp Ser Leu Asp Pro Lys Leu Met
225                 230                 235                 240

Glu Ser Leu Arg Glu Asn Ala Lys Ile Trp Gly Leu Tyr Leu Thr Val
                 245                 250                 255

Cys Asp Asp His Val Pro Leu Arg Ala Lys His Val Arg Leu His Tyr
             260                 265                 270

Gly Asp Gly Pro Asp Glu Asn Arg Lys Thr Arg Asn Leu Arg Lys Asn
             275                 280                 285

Asn Pro Phe Trp Lys Ala Val Thr Ile Leu Lys Phe Lys Arg Asp Leu
         290                 295                 300

Asp Gly Glu Lys Gln Ile Pro Glu Phe Met Tyr Gly Glu His Ile Glu
305                 310                 315                 320

Val Arg Glu Ala Phe Leu Ala Gly Leu Ile Asp Ser Asp Gly Tyr Val
                 325                 330                 335

Val Lys Lys Gly Glu Gly Pro Glu Ser Tyr Lys Ile Ala Ile Gln Thr
             340                 345                 350

Val Tyr Ser Ser Ile Met Asp Gly Ile Val His Ile Ser Arg Ser Leu
             355                 360                 365

Gly Met Ser Ala Thr Val Thr Thr Arg Ser Ala Arg Glu Glu Ile Ile
             370                 375                 380

Glu Gly Arg Lys Val Gln Cys Gln Phe Thr Tyr Asp Cys Asn Val Ala
385                 390                 395                 400

Gly Gly Thr Thr Ser Gln Asn Val Leu Ser Tyr Cys Arg Ser Gly His
                 405                 410                 415

Lys Thr Arg Glu Val Pro Pro Ile Ile Lys Arg Glu Pro Val Tyr Phe
```

```
                420             425             430
Ser Phe Thr Asp Asp Phe Gln Gly Glu Ser Thr Val Tyr Gly Leu Thr
            435                 440                 445

Ile Glu Gly His Lys Asn Phe Leu Leu Gly Asn Lys Ile Glu Val Lys
        450                 455                 460

Ser Cys Arg Gly Cys Cys Val Gly Glu Gln Leu Lys Ile Ser Gln Lys
465                 470                 475                 480

Lys Asn Leu Lys His Cys Val Ala Cys Pro Arg Lys Gly Ile Lys Tyr
                485                 490                 495

Phe Tyr Lys Asp Trp Ser Gly Lys Asn Arg Val Cys Ala Arg Cys Tyr
            500                 505                 510

Gly Arg Tyr Lys Phe Ser Gly His His Cys Ile Asn Cys Lys Tyr Val
        515                 520                 525

Pro Glu Ala Arg Glu Val Lys Lys Ala Lys Asp Lys Gly Glu Lys Leu
            530                 535                 540

Gly Ile Thr Pro Glu Gly Leu Pro Val Lys Gly Pro Glu Cys Ile Lys
545                 550                 555                 560

Cys Gly Gly Ile Leu Gln Phe Asp Ala Val Arg Gly Pro His Lys Ser
                565                 570                 575

Cys Gly Asn Asn Ala Gly Ala Arg Ile Cys
            580                 585

<210> SEQ ID NO 15
<211> LENGTH: 1758
<212> TYPE: DNA
<213> ORGANISM: Saccharomyces cerevisiae
<220> FEATURE:
<221> NAME/KEY: misc_feature
<222> LOCATION: (1)..(1758)
<223> OTHER INFORMATION: HO polynucleotide

<400> SEQUENCE: 15
atgctttctg aaaacacgac tattctgatg gctaacggtg aaattaaaga catcgcaaac      60
gtcacggcta actcttacgt tatgtgcgca gatggctccg ctgcccgcgt cataaatgtc     120
acacagggct atcagaaaat ctataatata cagcaaaaaa ccaaacacag agcttttgaa     180
ggtgaacctg gtaggttaga tcccaggcgt agaacagttt atcagcgtct tgcattacaa     240
tgtactgcag gtcataaatt gtcagtcagg gtccctacca aaccactgtt ggaaaaaagt     300
ggtagaaatg ccaccaaata taagtgaga tggagaaatc tgcagcaatg tcagacgctt      360
gatggtagga taataataat tccaaaaaac catcataaga cattcccaat gacagttgaa     420
ggtgagtttg ccgcaaaacg cttcatagaa gaaatggagc gctctaaagg agaatatttc     480
aactttgaca ttgaagttag agatttggat tatcttgatg ctcaattgag aatttctagc     540
tgcataagat ttggtccagt actcgcagga aatggtgttt atctaaatt tctcactgga      600 cgtagtgacc ttgtaactcc tgctgtaaaa agtatggctt ggatgcttgg tctgtggtta     660
ggtgacagta caacaaaaga gccagaaatc tcagtagata gcttggatcc taagctaatg     720
gagagtttaa gagaaaatgc gaaaatctgg ggtctctacc ttacggtttg tgacgatcac     780
gttccgctac gtgccaaaca tgtaaggctt cattatggag atggtccaga tgaaaacagg     840
aagacaagga atttgaggaa aaataatcca ttctggaaag ctgtcacaat tttaaagttt     900
aaaagggatc ttgatggaga gaagcaaatc cctgaattta tgtacggcga gcatatagaa     960
gttcgtgaag cattcttagc cggcttgatc gactcagatg gtacgttgt gaaaaagggc    1020 gaaggccctg aatcttataa aatagcaatt caaactgttt attcatccat tatggacgga    1080
```

```
attgtccata tttcaagatc tcttggtatg tcagctactg tgacgaccag gtcagctagg    1140
gaggaaatca ttgaaggaag aaaagtccaa tgtcaattta catacgactg taatgttgct    1200 ggggaacaa cttcacagaa tgttttgtca tattgtcgaa gtggtcacaa aacaagagaa    1260
gttccgccaa ttataaaaag ggaacccgta tatttcagct tcacggatga tttccagggt    1320
gagagtactg tatatgggct tacgatagaa ggccataaaa atttcttgct tggcaacaaa    1380
atagaagtga aatcatgtcg aggctgctgt gtgggagaac agcttaaaat atcacaaaaa    1440
aagaatctaa aacactgtgt tgcttgtccc agaaagggaa tcaagtattt ttataaagat    1500
tggagtggta aaaatcgagt atgtgctaga tgctatggaa gatacaaatt cagcggtcat    1560
cactgtataa attgcaagta tgtaccagaa gcacgtgaag tgaaaaaggc aaaagacaaa    1620
ggcgaaaaat tgggcattac gcccgaaggt ttgccagtta aaggaccaga gtgtataaaa    1680
tgtggcggaa tcttacagtt tgatgctgtc cgcgggcctc ataagagttg tggtaacaac    1740
gcaggtgcgc gcatctgc                                                  1758
```